United States Patent
Peters

(10) Patent No.: US 12,171,751 B2
(45) Date of Patent: *Dec. 24, 2024

(54) METHODS OF TREATING INTRAOCULAR PRESSURE WITH ACTIVATORS OF TIE-2

(71) Applicant: EyePoint Pharmaceuticals, Inc., Watertown, MA (US)

(72) Inventor: Kevin Peters, Cincinnati, OH (US)

(73) Assignee: EyePoint Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/304,511

(22) Filed: Apr. 21, 2023

(65) Prior Publication Data

US 2023/0398100 A1   Dec. 14, 2023

Related U.S. Application Data

(63) Continuation of application No. 17/150,430, filed on Jan. 15, 2021, now Pat. No. 11,666,558, which is a continuation of application No. 15/273,068, filed on Sep. 22, 2016, now Pat. No. 10,952,992.

(60) Provisional application No. 62/222,481, filed on Sep. 23, 2015.

(51) Int. Cl.
| | | |
|---|---|---|
| A61K 31/426 | (2006.01) | |
| A61K 31/427 | (2006.01) | |
| A61K 31/428 | (2006.01) | |
| A61K 31/433 | (2006.01) | |
| A61K 31/496 | (2006.01) | |
| A61K 31/497 | (2006.01) | |
| A61K 31/513 | (2006.01) | |
| A61P 27/02 | (2006.01) | |
| A61P 27/06 | (2006.01) | |

(52) U.S. Cl.
CPC .......... *A61K 31/426* (2013.01); *A61K 31/427* (2013.01); *A61K 31/428* (2013.01); *A61K 31/433* (2013.01); *A61K 31/496* (2013.01); *A61K 31/497* (2013.01); *A61K 31/513* (2013.01); *A61P 27/02* (2018.01); *A61P 27/06* (2018.01)

(58) Field of Classification Search
CPC ..... A61K 31/426; A61K 31/427; A61P 27/02; A61P 27/06
See application file for complete search history.

(56) References Cited

U.S. PATENT DOCUMENTS

| | | |
|---|---|---|
| 645,503 A | 3/1900 | Crowley |
| 953,924 A | 4/1910 | Schweimler |
| 5,919,813 A | 7/1999 | De, Jr. et al. |
| 5,980,929 A | 11/1999 | De, Jr. et al. |
| 6,455,035 B1 | 9/2002 | Suri et al. |
| 7,052,695 B2 | 5/2006 | Kalish |
| 7,226,755 B1 | 6/2007 | Peters et al. |
| 7,309,483 B2 | 12/2007 | Wiegand et al. |
| 7,354,579 B2 | 4/2008 | Holash et al. |
| 7,507,568 B2 | 3/2009 | Evdokimov et al. |
| 7,589,212 B2 | 9/2009 | Gray et al. |
| 7,622,593 B2 | 11/2009 | Gray et al. |
| 7,632,862 B2 | 12/2009 | Peters et al. |
| 7,740,846 B2 | 6/2010 | Gerber et al. |
| 7,769,575 B2 | 8/2010 | Evdokimov et al. |
| 7,795,444 B2 | 9/2010 | Gray et al. |
| 7,973,142 B2 | 7/2011 | Rotello et al. |
| 8,106,078 B2 | 1/2012 | Gray et al. |
| 8,188,125 B2 | 5/2012 | Gray et al. |
| 8,258,311 B2 | 9/2012 | Gray et al. |
| 8,329,916 B2 | 12/2012 | Amarasinghe et al. |
| 8,338,615 B2 | 12/2012 | Gray et al. |
| 8,524,235 B2 | 9/2013 | Rotello et al. |
| 8,569,348 B2 | 10/2013 | Shalwitz et al. |
| 8,846,685 B2 | 9/2014 | Gray et al. |
| 8,883,832 B2 | 11/2014 | Shalwitz et al. |
| 8,895,563 B2 | 11/2014 | Gray et al. |
| 8,946,232 B2 | 2/2015 | Gray et al. |
| 8,968,766 B2 | 3/2015 | Hughes et al. |
| 8,999,325 B2 | 4/2015 | Peters et al. |
| 8,999,953 B2 | 4/2015 | Loftsson et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 9,248,172 B2 | 2/2016 | Srivastava et al. |
| 9,284,285 B2 | 3/2016 | Gray et al. |

(Continued)

FOREIGN PATENT DOCUMENTS

| | | |
|---|---|---|
| EP | 1165115 B1 | 5/2003 |
| EP | 2004697 A2 | 12/2008 |

(Continued)

OTHER PUBLICATIONS

Amarasinghe, et al., Design and synthesis of potent, non-peptidic inhibitors of HPTPP, Bioorganic & Medcinal Chemistry Letters, 16(16):4252-56 Elsevier Ltd., United Kingdom (Aug. 2006).
Baumer, et al. Vascular endothelial cell-specific phosphotyrosine phosphatase (VE-PTP) activity is required for blood vessel development. Blood. Jun. 15, 2006;107(12):4754-62. Epub Mar. 2, 2006 Elsevier B.V., United States.
"High Eye Pressure and Glaucom, Available at web.archive.org/web/20140822034439, http://www.glaucoma.org/gleams/high-eyepressure-andglaucoma. php, Accessed on Sep. 28, 2017".
International search report and written opinion dated Dec. 12, 2016 for PCT Application No. US-201653107.

(Continued)

*Primary Examiner* — James D. Anderson
(74) *Attorney, Agent, or Firm* — Sterne, Kessler, Goldstein & Fox P.L.L.C.

(57) ABSTRACT

Disclosed herein are compounds effective for activation of Tie-2 and inhibition of HPTP-beta. The compounds can provide effective therapy for eye conditions associated with angiogenesis, for example, intraocular pressure, ocular hypertension, and glaucoma.

20 Claims, 22 Drawing Sheets

(56) References Cited

U.S. PATENT DOCUMENTS

| | | |
|---|---|---|
| 9,403,789 B2 | 8/2016 | Eissenstat et al. |
| 9,440,963 B2 | 9/2016 | Peters et al. |
| 9,539,245 B2 | 1/2017 | Peters |
| RE46,592 E | 10/2017 | Gray et al. |
| 9,795,594 B2 | 10/2017 | Gray et al. |
| 9,926,367 B2 | 3/2018 | Rotello et al. |
| 9,949,956 B2 | 4/2018 | Shalwitz et al. |
| 10,150,811 B2 | 12/2018 | Peters et al. |
| 10,220,048 B2 | 3/2019 | Peters et al. |
| 10,329,357 B2 | 6/2019 | Peters et al. |
| 10,463,650 B2 | 11/2019 | Gray et al. |
| 10,952,992 B2 * | 3/2021 | Peters .................. A61K 31/497 |
| 11,253,502 B2 | 2/2022 | Peters |
| 11,666,558 B2 * | 6/2023 | Peters .................. A61K 31/496 |
| | | 514/254.02 |
| 2003/0040463 A1 | 2/2003 | Wiegand et al. |
| 2007/0072920 A1 | 3/2007 | Hellberg et al. |
| 2008/0268051 A1 | 10/2008 | Hughes et al. |
| 2010/0016336 A1 | 1/2010 | Gray et al. |
| 2010/0056610 A1 | 3/2010 | Peters et al. |
| 2010/0160356 A1 | 6/2010 | Heinrich et al. |
| 2010/0226992 A1 | 9/2010 | Kabra |
| 2011/0268694 A1 | 11/2011 | Shalwitz et al. |
| 2012/0129847 A1 | 5/2012 | Peters et al. |
| 2013/0023542 A1 | 1/2013 | Gray et al. |
| 2013/0095065 A1 | 4/2013 | Peters et al. |
| 2013/0137741 A1 | 5/2013 | Kabra et al. |
| 2013/0190324 A1 | 7/2013 | Kompella et al. |
| 2013/0331386 A1 | 12/2013 | Shalwitz et al. |
| 2014/0010805 A1 | 1/2014 | Hart et al. |
| 2014/0044707 A1 | 2/2014 | Rotello et al. |
| 2014/0066458 A1 | 3/2014 | Shalwitz et al. |
| 2014/0073566 A1 | 3/2014 | Koh et al. |
| 2014/0288134 A1 | 9/2014 | Peters et al. |
| 2015/0030603 A1 | 1/2015 | Kim et al. |
| 2015/0050277 A1 | 2/2015 | Peters et al. |
| 2015/0065781 A1 | 3/2015 | Bais et al. |
| 2015/0071941 A1 | 3/2015 | Sodhi et al. |
| 2015/0125455 A1 | 5/2015 | Green et al. |
| 2015/0125542 A1 | 5/2015 | Ohto et al. |
| 2015/0175676 A1 | 6/2015 | Fandl et al. |
| 2015/0190432 A1 | 7/2015 | Doiron et al. |
| 2015/0232575 A1 | 8/2015 | Peters et al. |
| 2015/0258120 A1 | 9/2015 | Zarnitsyn et al. |
| 2015/0259335 A1 | 9/2015 | Janusz et al. |
| 2015/0290235 A1 | 10/2015 | Gros et al. |
| 2015/0297740 A1 | 10/2015 | Rau et al. |
| 2016/0000871 A1 | 1/2016 | Quaggin |
| 2016/0015810 A1 | 1/2016 | Deschatelets et al. |
| 2016/0030393 A1 | 2/2016 | Breslin et al. |
| 2016/0045566 A1 | 2/2016 | Purcell et al. |
| 2016/0058828 A1 | 3/2016 | Dumont et al. |
| 2016/0082129 A1 | 3/2016 | Peters |
| 2016/0130321 A1 | 5/2016 | Burian |
| 2016/0130337 A1 | 5/2016 | Gekkieva et al. |
| 2016/0137717 A1 | 5/2016 | Burian |
| 2016/0144025 A1 | 5/2016 | Vitti et al. |
| 2016/0151410 A1 | 6/2016 | Ma et al. |
| 2016/0151448 A1 | 6/2016 | Van et al. |
| 2016/0159893 A1 | 6/2016 | Burian et al. |
| 2016/0168240 A1 | 6/2016 | Burian et al. |
| 2016/0220540 A1 | 8/2016 | Peters et al. |
| 2016/0220541 A1 | 8/2016 | Peters et al. |
| 2016/0251421 A1 | 9/2016 | Brown et al. |
| 2016/0252526 A1 | 9/2016 | Bergmann et al. |
| 2017/0145416 A1 | 5/2017 | Epstein et al. |
| 2017/0260265 A1 | 9/2017 | Duerr et al. |
| 2018/0016245 A1 | 1/2018 | Shalwitz et al. |
| 2018/0022741 A1 | 1/2018 | Peters et al. |
| 2018/0037579 A1 | 2/2018 | Peters et al. |
| 2018/0092883 A1 | 4/2018 | Peters et al. |
| 2019/0023773 A1 | 1/2019 | Rotello et al. |
| 2019/0076405 A1 | 3/2019 | Shalwitz et al. |
| 2019/0256889 A1 | 8/2019 | Quaggin |

FOREIGN PATENT DOCUMENTS

| | | | |
|---|---|---|---|
| EP | 2371865 A2 | 10/2011 | |
| EP | 2385763 A1 | 11/2011 | |
| EP | 2451279 A1 | 5/2012 | |
| EP | 2142189 B1 | 2/2013 | |
| EP | 2592072 A2 | 5/2013 | |
| EP | 2592073 A2 | 5/2013 | |
| EP | 2624916 A2 | 8/2013 | |
| EP | 2766043 A1 | 8/2014 | |
| EP | 2766044 A1 | 8/2014 | |
| EP | 2041129 B1 | 9/2014 | |
| EP | 2041102 B1 | 11/2014 | |
| EP | 2803663 A1 | 11/2014 | |
| EP | 2038265 B1 | 3/2015 | |
| EP | 2967066 A1 | 1/2016 | |
| EP | 3168234 A1 | 5/2017 | |
| JP | 2015199733 A | 11/2015 | |
| WO | WO-9818914 A1 | 5/1998 | |
| WO | WO-0057901 A1 | 10/2000 | |
| WO | WO-0065085 A1 | 11/2000 | |
| WO | WO-03084565 A2 | 10/2003 | |
| WO | WO-2007033216 A2 | 3/2007 | |
| WO | WO-2007116360 A2 | 10/2007 | |
| WO | WO-2008002569 A2 | 1/2008 | |
| WO | WO-2008002570 B1 | 4/2008 | |
| WO | WO-2008002571 B1 | 4/2008 | |
| WO | WO-2010081172 A1 | 7/2010 | |
| WO | WO-2010097800 A1 | 9/2010 | |
| WO | WO-2011005330 A1 | 1/2011 | |
| WO | WO-2012047966 A2 | 4/2012 | |
| WO | WO-2013056233 A1 | 4/2013 | |
| WO | WO-2013056240 A1 | 4/2013 | |
| WO | WO-2014145068 A1 * | 9/2014 | ............ A61K 31/04 |
| WO | WO-2015138882 A1 | 9/2015 | |
| WO | WO-2015152416 A1 | 10/2015 | |
| WO | WO-2016022813 A1 | 2/2016 | |
| WO | WO-2016049183 A1 | 3/2016 | |
| WO | WO-2017053566 A1 | 3/2017 | |

OTHER PUBLICATIONS

Jeansson, et al., Angiopoietin-1 is essential in mouse vasculature during development and In response to injury, The Journal of Clinical Investigation, 121(6):2278-89, The American Society for Clinical Investigation, United States (Jun. 2011).

Kernt, et al., Intravitreal bevacizumab (Avastin) treatment is safe in terms of intraocular and blood pressure, Acta Ophthalmologica 85(1):1-4, Wiley-Blackwell Publishing Ltd., United Kingdom (Feb. 2007).

Kurna, Sevda Aydin et al., The Effects of Topical Antiglaucoma Drugs and Monotheraphy on the Ocular Surface: A Prospective Study, Journal of Opthalmology, vol. 2014, Jan. 1, 2014, pp. 1-8, XP055654445, US ISSN:2090-004XX, DOI:10.1155/2014/460483.

Lip, et al. Plasma vascular endothelial growth factor, angiopoietin-2, and soluble angiopoietin receptor tie-2 in diabetic retinopathy: effects of laser photocoagulation and angiotensin receptor blockade. Br J Ophthalmol. Dec. 2004;88(12):1543-6, BMJ Publishing Group, United Kingdom.

Nawroth, et al. VE-PTP and VE-cadherin ectodomains interact to facilitate regulation of phosphorylation and cell contacts. Embo J. Sep. 16, 2002;21(18):4885-95 Springer Nature, Germany.

Office action dated Apr. 8, 2020 for U.S. Appl. No. 15/273,068.

Office action dated Feb. 20, 2018 for U.S. Appl. No. 15/273,068.

Office action dated Aug. 7, 2017 for U.S. Appl. No. 15/273,068.

Shen, et al. Targeting VE-PTP activates TIE2 and stabilizes the ocular vasculature. J Clin Invest. Oct. 2014; 124(10):4564-76, The American Society for Clinical Investigation, United States.

Thomson, Benjamin R. et al., Defects in Angiopoietin-Tie2 signaling lead to dose- dependent glaucoma in mice Program No. 6084, ARVO 2016 Annual Meeting Abstracts, May 5, 2016, pp. 1-4, XP055569557, Retrieved from the Internet.

Thomson, et al., A lymphatic defect causes ocular hypertension and glaucoma in mice, The Journal of Clinical Investigation, Oct. 2014, 124(10):4320-4, The American Society for Clinical Investigation, United States.

(56) References Cited

OTHER PUBLICATIONS

"Types of Glaucoma, Available at web.archive.org/web/20140822230205, www.glaucoma.org/glaucoma/types-of-glaucoma.php, Accessed on Sep. 28, 2017".
Vestweber, et al., Molecular Mechanisms That Control Endothelial Cell Contacts, J. Pathol 190(3):281-91, John Wiley and Sons Ltd., United Kingdom (Feb. 2000).
XP-0027789738,Database WPI Week 201571 Thomson Scientific, London, GB, An 2015-61106C & WO 2015/152415A1 (Shiseido Co. Ltd.) Oct. 8, 2015.
Yacyshyn, et al. Tyrosine phosphatase beta regulates angiopoietin-Tie2 signaling in human endothelial cells. Angiogenesis. 2009;12(1):25-33. doi: 10.1007/s10456-008-9126-0. Epub Jan. 1, 2009, Springer Netherlands, Netherlands.
Kernt, M., et al., "Intravitreal bevacizumab (Avastin) treatment is safe in terms of intraocular and blood pressure," Acta Opthalmologica 85(1):119-120, Wiley, United States (2007).
Stamer, W.D., et al., "By targeting Tie2/VE-PTP in Schlemm's canal, AKB-9778 lowers intraocular pressure via increasing outflow facility in mice," Investigative Ophthalmology & Visual Science 60:2186, pp. 1-2, Association for Research in Vision and Ophthalmology, United States (2019).

\* cited by examiner

METHODS OF TREATING INTRAOCULAR PRESSURE WITH ACTIVATORS OF TIE-2

CROSS REFERENCE

This Application is a continuation of U.S. application Ser. No. 17/150,430, filed Jan. 15, 2021, which is a continuation of U.S. application Ser. No. 15/273,068 filed Sep. 22, 2016, which claims the benefit of U.S. Provisional Application No. 62/222,481 filed Sep. 23, 2015, each of which is incorporated herein by reference in its entirety.

BACKGROUND OF THE INVENTION

Intraocular pressure is a significant pathology associated with glaucomas, such as primary open angle glaucoma. The intraocular pressure is generated through damage to the trabecular meshwork of the eye, which results in optic nerve damage and loss of vision. Ocular hypertension occurs when the pressure in the eye surpasses the normal range with no detectable changes in vision or damage to the structure of your eyes. People with ocular hypertension have an increased risk of glaucoma.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a method for reducing intraocular pressure in a subject in need thereof, the method comprising administering to the subject a therapeutically-effective amount of a Tie-2 activator, wherein the administration reduces the intraocular pressure by about 0.1 mmHg to about 9 mmHg compared to absence of administration.

In some embodiments, the invention provides a method for treating glaucoma in a subject in need thereof, the method comprising administering to the subject a therapeutically-effective amount of a Tie-2 activator, wherein the administration reduces intraocular pressure by about 0.1 mmHg to about 9 mmHg compared to absence of administration.

DETAILED DESCRIPTION OF THE INVENTION

Figure 1:
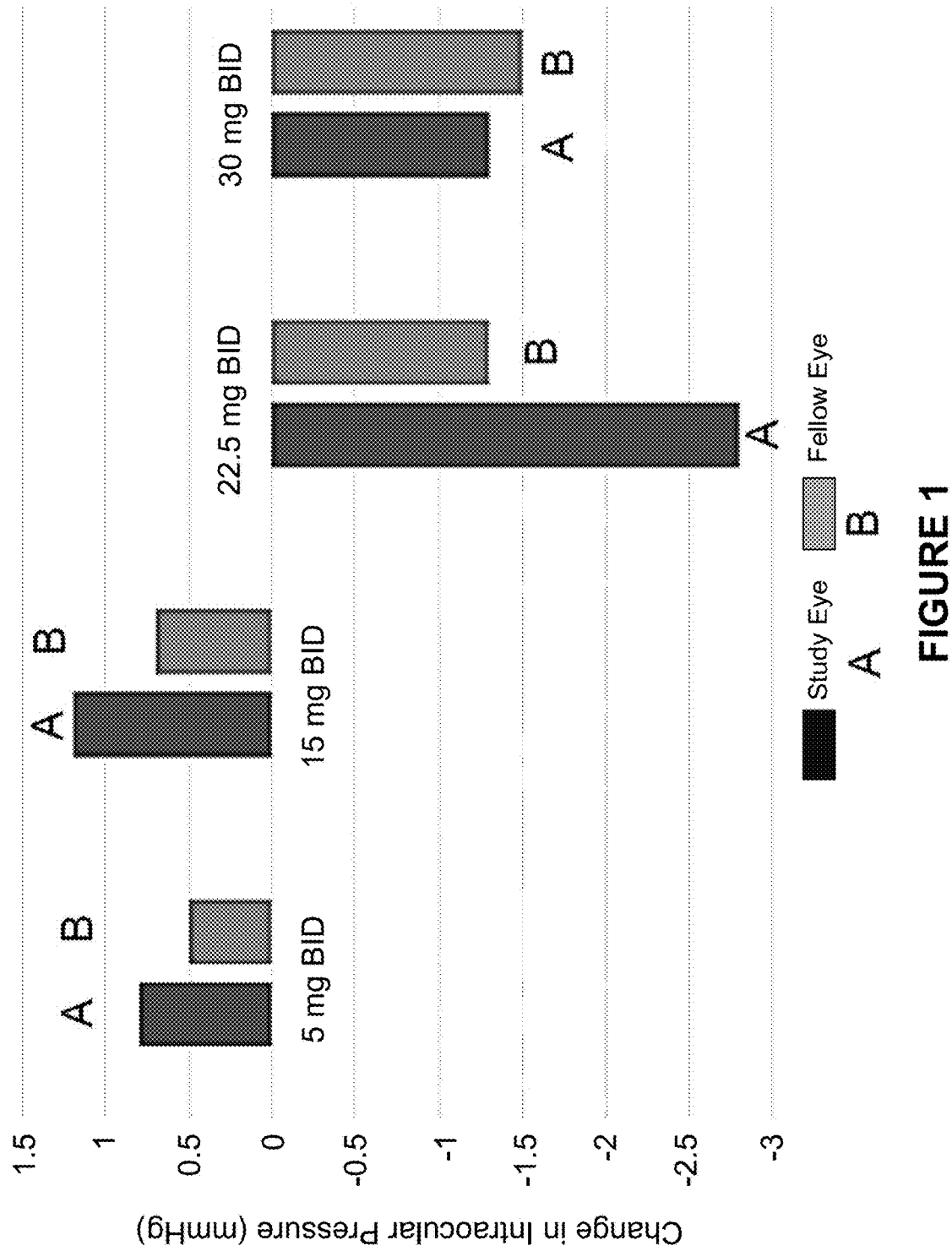
FIG. 1 illustrates changes in intraocular pressure from baseline. A: study eye; B: fellow eye.

Described herein are therapies using a Tie-2 activator for treatment of elevated intraocular pressure and ocular hypertension. A Tie-2 activator of the disclosure can activate Tie-2 signaling by promoting protein phosphorylation, such as phosphorylation of the Tie-2 protein. The intraocular pressure can be associated with glaucoma.

Tie-2 (tyrosine kinase with immunoglobulin and epidermal growth factor homology domains 2) is a membrane receptor tyrosine kinase expressed primarily in vascular endothelial cells and a subset of hematopoietic stem cells (HSCs) and macrophages. The principle regulators of Tie-2 phosphorylation are angiopoietin 1 (Ang-1) and angiopoietin 2 (Ang-2). Ang-1 is an agonist of Tie-2, and binding of Ang-1 to Tie-2 promotes receptor phosphorylation. Ang-2 is a Tie-2 ligand that acts in a context-dependent antagonistic or agonistic manner. Binding of Ang-1 to Tie-2 increases the level of endogenous Tie-2 receptor phosphorylation and initiates downstream AKT signaling. This binding initiates a signaling cascade that can induce distinctive vascular remodeling through highly organized angiogenesis and tightening of the endothelial cell junctions (endothelium cell proximity). Within the vascular endothelium, Ang-1-Tie-2 signaling promotes endothelial cell proximity. In the HSC microenvironment, Ang-1-Tie-2 signaling contributes in a paracrine manner to the long-term repopulation of HSCs.

Under physiological conditions, the duration of Tie-2 phosphorylation is regulated by the human protein tyrosine phosphatase beta (often abbreviated as HPTPβ or HPTP beta), which removes the phosphate from the Tie-2 receptor. By inhibiting HPTPβ, the level of Tie-2 phosphorylation substantially increases, restoring proper cell proximity. HPTPβ plays a functional role in endothelial cell proliferation, viability, differentiation, vasculogenesis, and angiogenesis. HPTPβ and vascular endothelial protein tyrosine phosphatase (VE-PTP; the mouse orthologue of HPTPβ) are expressed in vascular endothelial cells throughout development. A small molecule of the disclosure can activate Tie-2 downstream signaling by inhibiting HPTPβ/VE-PTP.

A therapy of the disclosure can be used to treat elevated intraocular pressure (IOP). Intraocular pressure arises from increased fluid pressure inside the eye. Pressure within the eye is maintained by the balance between the fluid entering the eye through the ciliary body and the fluid exiting the eye through the trabecular meshwork. The normal range of introcular pressure is between about 10 mmHg to about 21 mmHg. Elevated intraocular pressure in the absence of glaucoma is referred to as ocular hypertension (OHT), which can damage to the trabecular meshwork that is associated with glaucoma. High pressure in the eye can cause damage to the optic nerve and impair central and peripheral vision.

Failure to diagnose or treat symptoms of IOP, OHT, or glaucoma can lead to permanent vision loss. The glaucoma can be, for example, primary glaucoma, pseudoexfoliative glaucoma, pigmentary glaucoma, primary juvenile glaucoma, open angle glaucoma, wide-angle glaucoma, close-angle glaucoma, congenital glaucoma, acquired glaucoma, secondary glaucoma, inflammatory glaucoma, phacogenic glaucoma, or neovascular glaucoma. In some cases, a Tie-2 activator of the disclosure can stabilize vasculature associated with the trabecular meshwork, reducing intraocular pressure and treating ocular hypertension.

Tie-2 Activators.

Compounds disclosed herein can be effective as Tie-2 activators. The compounds can promote that activity, for example, by binding to or inhibiting HPTPβ. Such compounds can bind to HPTPβ, for example, by mimicking the binding mechanism of a native substrate, such as a phosphorylated compound. A compound can be a phosphate mimetic or bioisostere, for example, a sulfamic acid. The compound could also be derived from an amino acid building block or comprise an amino acid backbone for efficiency and economy of synthesis.

In some embodiments, a compound of the invention is a compound of the formula:

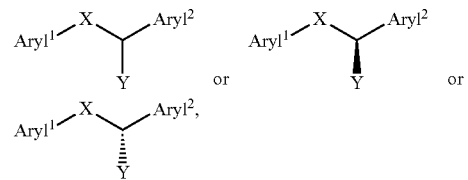

wherein:
Aryl$^1$ is an aryl group which is substituted or unsubstituted; Aryl$^2$ is an aryl group which is substituted or unsubstituted; X is alkylene, alkenylene, alkynylene, an ether linkage, an amine linkage, an amide linkage, an ester linkage, a thioether linkage, a carbamate linkage, a carbonate linkage, a sulfone linkage, any of which is substituted or unsubstituted, or a chemical bond; and Y is H, aryl, heteroaryl, NH(aryl), NH(heteroaryl), NHSO$_2$R$^g$, or NHCOR$^g$, any of which is substituted or unsubstituted, or

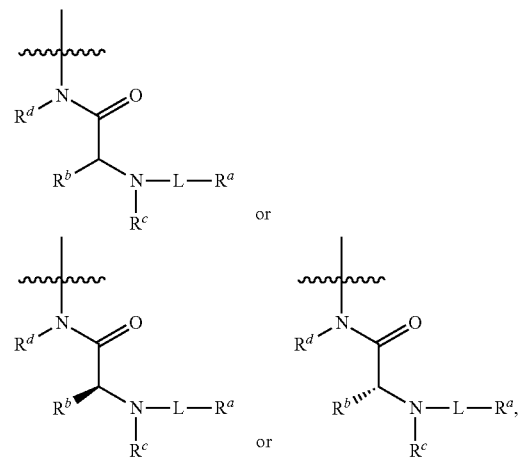

wherein:
L is alkylene, alkenylene, or alkynylene, any of which is substituted or unsubstituted, or together with the nitrogen atom to which L is bound forms an amide linkage, a carbamate linkage, or a sulfonamide linkage, or a chemical bond, or together with any of R$^a$, R$^b$, R$^c$, and R$^d$ forms a ring that is substituted or unsubstituted; R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^b$, R$^c$, and R$^d$ forms a ring that is substituted or unsubstituted; R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^a$, R$^c$, and R$^d$ forms a ring that is substituted or unsubstituted; R$^c$ is H or alkyl which is substituted or unsubstituted, or together with any of L, R$^a$, R$^b$, and R$^d$ forms a ring that is substituted or unsubstituted; R$^d$ is H or alkyl which is substituted or unsubstituted, or together with any of L, $R^a$, $R^b$, and $R^c$ forms a ring that is substituted or unsubstituted; and $R^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

In some embodiments, aryl$^1$ is substituted or unsubstituted phenyl, aryl$^2$ is substituted or unsubstituted heteroaryl, and X is alkylene. In some embodiments, aryl$^1$ is substituted phenyl, aryl$^2$ is substituted heteroaryl, and X is methylene.

In some embodiments, a compound is of the formula:

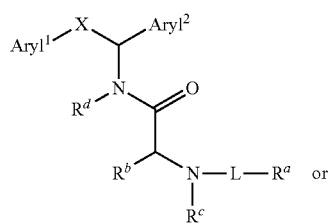

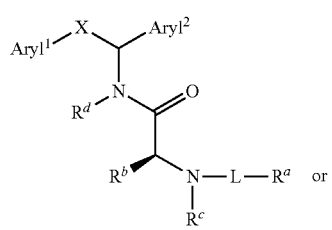

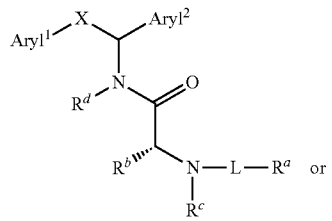

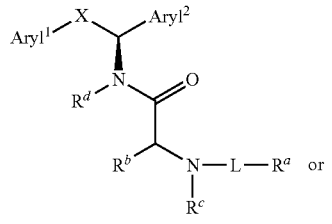

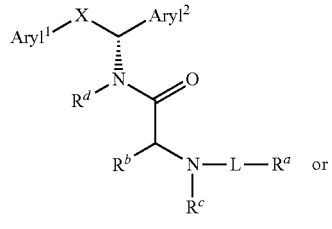

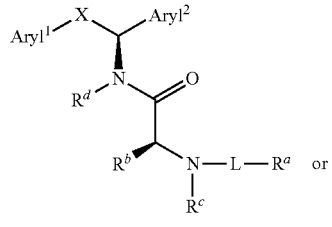

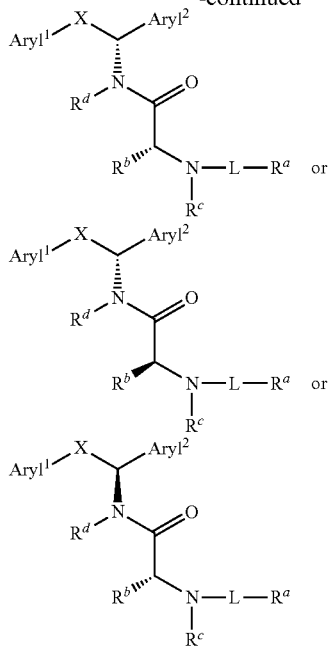

wherein aryl$^1$ is para-substituted phenyl, aryl$^2$ is substituted heteroaryl; X is methylene; L is alkylene, alkenylene, or alkynylene, any of which is substituted or unsubstituted, or together with the nitrogen atom to which L is bound forms an amide linkage, a carbamate linkage, or a sulfonamide linkage, or a chemical bond; $R^a$ is H, alkyl, alkenyl, alkynyl, aryl, arylalkyl, heterocyclyl, heterocyclylalkyl, heteroaryl, or heteroarylalkyl, any of which is substituted or unsubstituted; $R^b$ is H, alkyl, alkenyl, alkynyl, aryl, arylalkyl, heterocyclyl, heterocyclylalkyl, heteroaryl, or heteroarylalkyl, any of which is substituted or unsubstituted; $R^c$ is H or alkyl which is substituted or unsubstituted; and $R^d$ is H or alkyl which is substituted or unsubstituted.

In some embodiments, aryl$^1$ is para-substituted phenyl; aryl$^2$ is a substituted thiazole moiety; X is methylene; L together with the nitrogen atom to which L is bound forms a carbamate linkage; $R^a$ is alkyl, which is substituted or unsubstituted; $R^b$ is arylalkyl, which is substituted or unsubstituted; $R^c$ is H; and $R^d$ is H.

In some embodiments, Aryl$^2$ is:

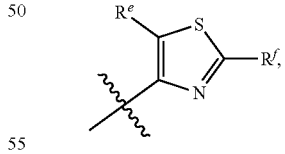

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

In some embodiments, $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, or an alkoxy group, any of which is substituted or unsubstituted and $R^f$ is alkyl, aryl, heterocyclyl, or heteroaryl, any of which is substituted or unsubstituted. In some embodiments, aryl$^1$ is 4-phenylsulfamic acid; $R^a$ is alkyl, which is substituted or unsubstituted; $R^b$ is arylalkyl, which is substituted or unsubstituted; $R^e$ is H; and $R^f$ is heteroaryl. In some embodiments, aryl$^1$ is 4-phenylsulfamic acid; $R^a$ is alkyl; which is substituted or unsubstituted; $R^b$ is arylalkyl, which is substituted or unsubstituted; $R^e$ is H; and $R^f$ is alkyl.

In some embodiments, Aryl$^2$ is:

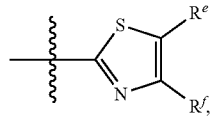

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted, $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, or an alkoxy group, any of which is substituted or unsubstituted; and $R^f$ is alkyl, aryl, heterocyclyl, or heteroaryl, any of which is substituted or unsubstituted. In some embodiments, aryl$^1$ is 4-phenylsulfamic acid; $R^a$ is alkyl, which is substituted or unsubstituted; $R^b$ is arylalkyl, which is substituted or unsubstituted; $R^e$ is H; and $R^f$ is heteroaryl.

In some embodiments, a substituted phenyl group is:

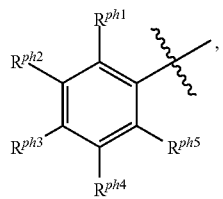

wherein:

each of $R^{ph1}$, $R^{ph2}$, $R^{ph3}$, $R^{ph4}$, and $R^{ph5}$ is independently H, OH, F, Cl, Br, I, CN, sulfamic acid, tosylate, mesylate, triflate, besylate, alkyl, alkenyl, alkynyl, an alkoxy group, a sulfhydryl group, a nitro group, a nitroso group, an azido group, a sulfoxide group, a sulfone group, a sulfonamide group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl.

Illustrative compounds include the following:

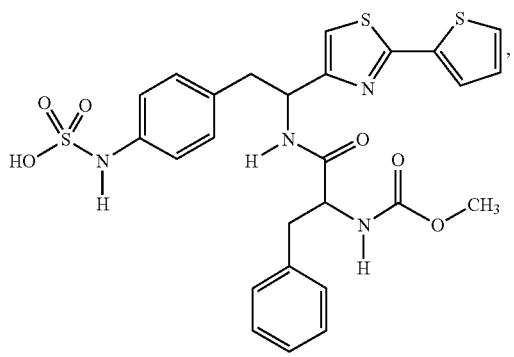

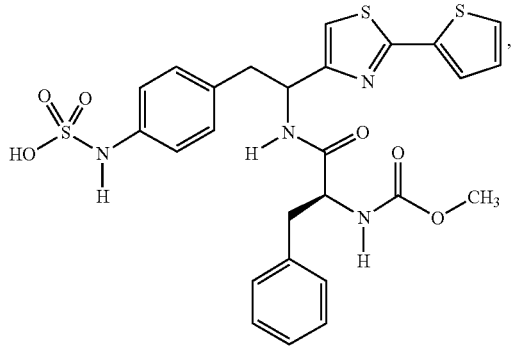

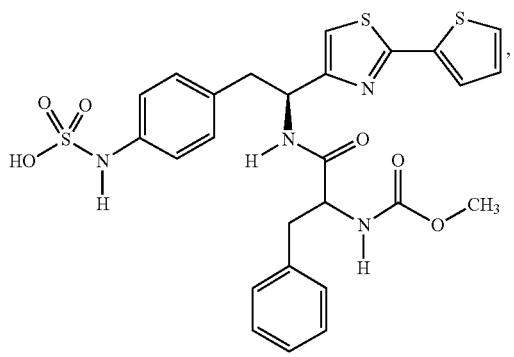

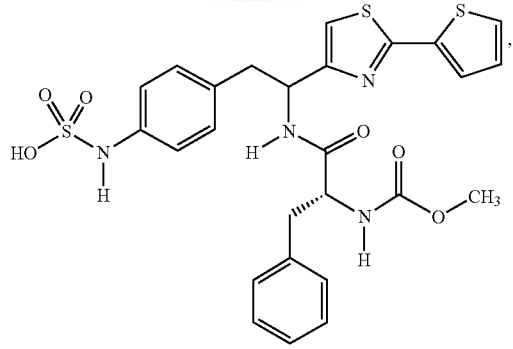
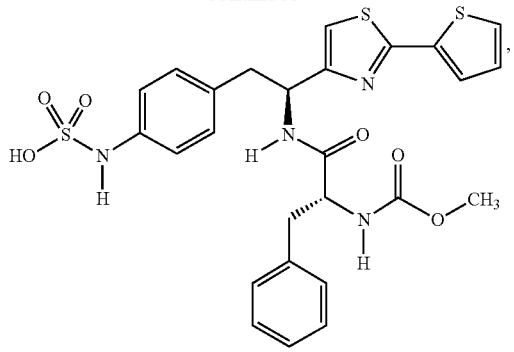
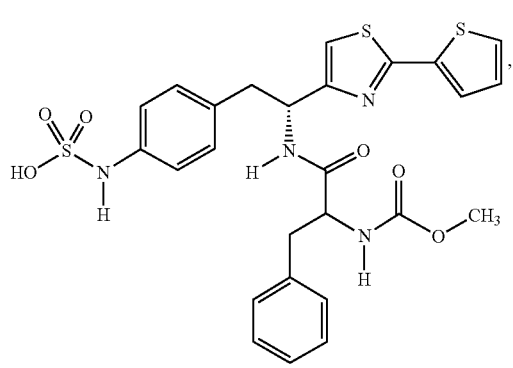
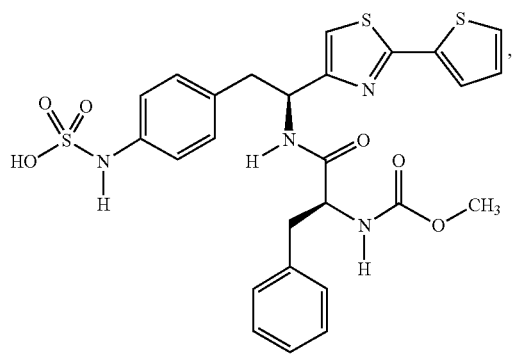
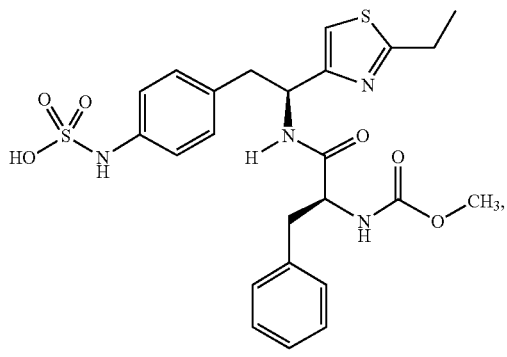
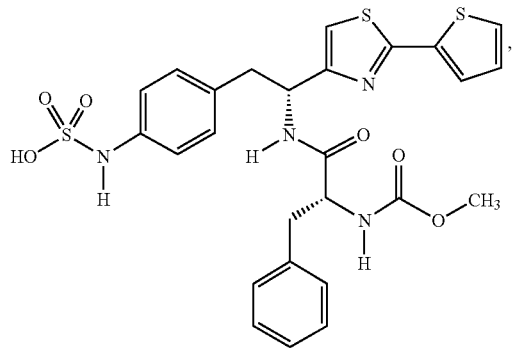
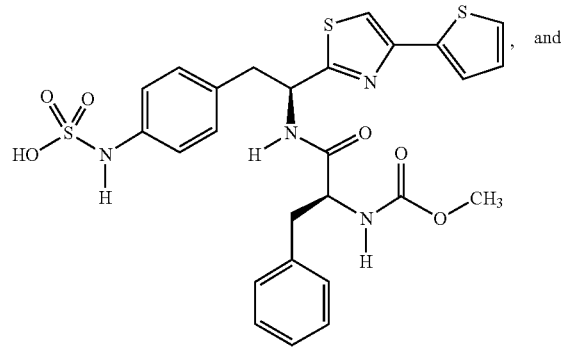

-continued

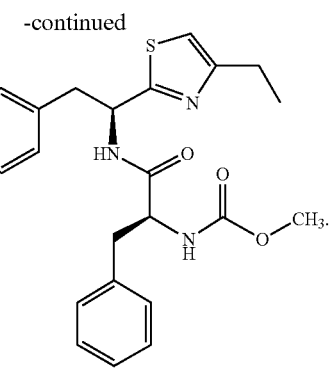

Optional Substituents for Chemical Groups.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, and ester groups.

Non-limiting examples of alkyl and alkylene groups include straight, branched, and cyclic alkyl and alkylene groups. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkynyl or alkynylene group can be internal or terminal. An alkynyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

Pharmaceutically-Acceptable Salts.

The invention provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, piprazole, imidazole, or pyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a piprazole salt, an imidazole salt, or a pyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccharic acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccharate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

A compound herein can be a salt of an acidic group, for example:

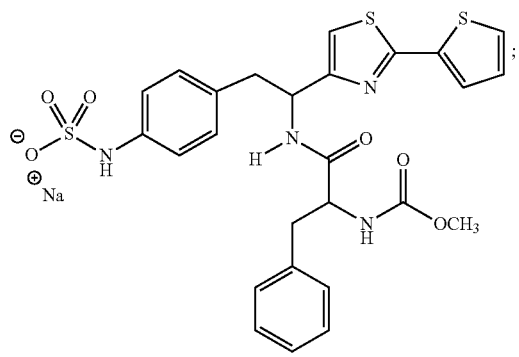

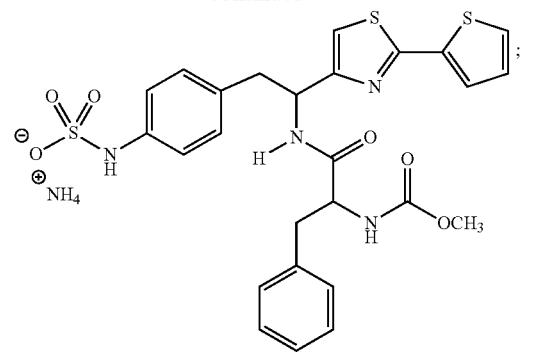

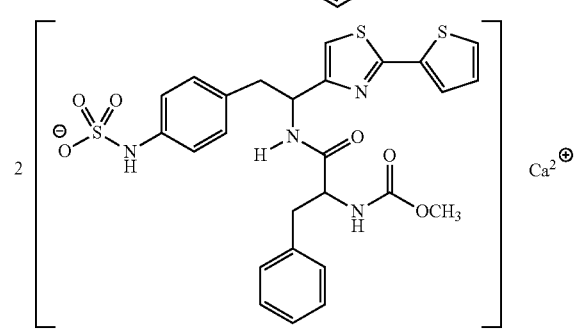

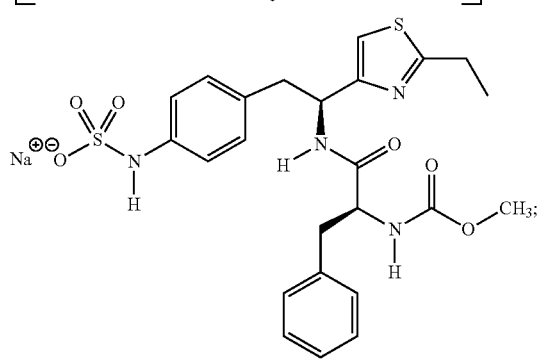

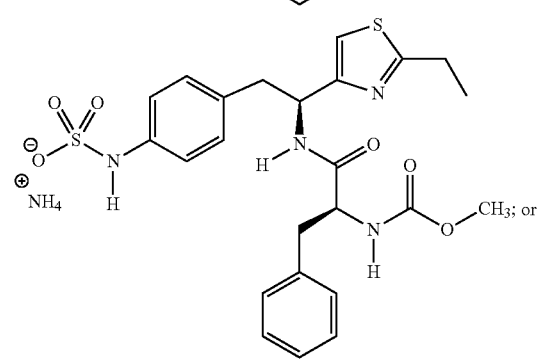

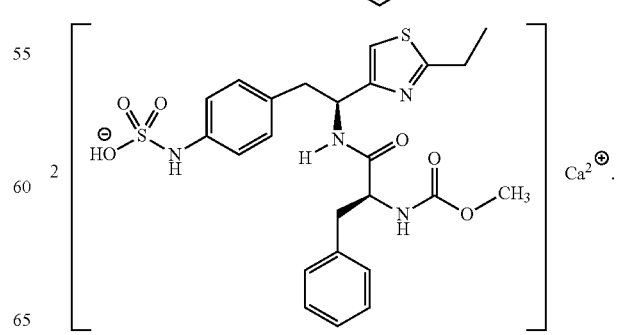

A compound herein can be a salt of a basic group formed from a strong acid, for example:

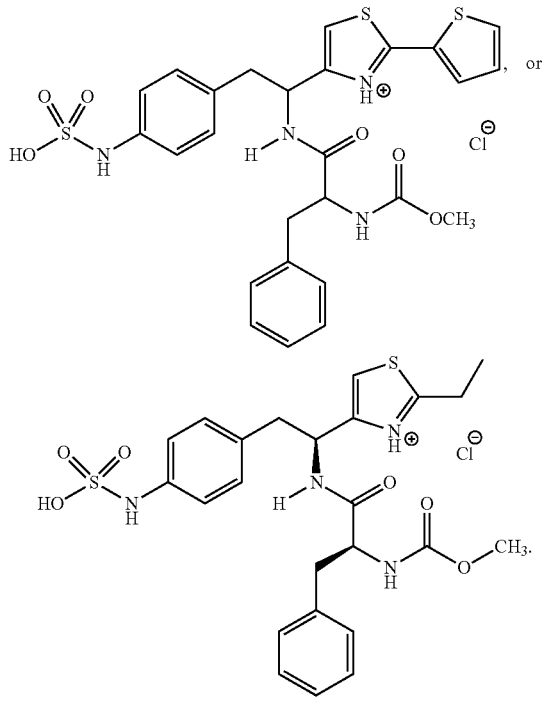

A compound herein can also exist in a zwitterionic form, for example:

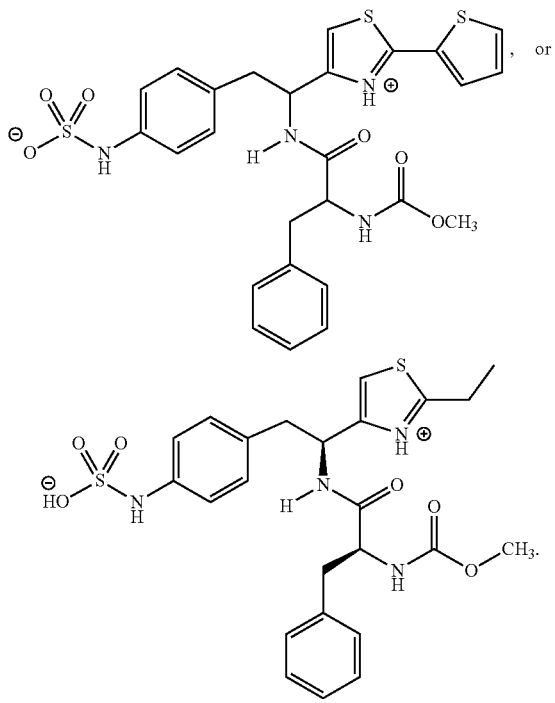

Formulations.

A pharmaceutical composition of the disclosure can provide a therapeutically-effective amount of an activator of Tie-2.

The disclosed formulations can comprise one or more pharmaceutically-acceptable agents, which alone or in combination solubilize a compound herein or a pharmaceutically-acceptable salt thereof.

In some embodiments, a compound or pharmaceutically-acceptable salt thereof is present in a formulation in an amount of from about 0.1 mg/mL to about 100 mg/mL, from about 0.1 mg/mL to about 1 mg/mL, from about 0.1 mg/mL to about 5 mg/mL, from about 5 mg/mL to about 10 mg/mL, from about 10 mg/mL to about 15 mg/mL, from about 15 mg/mL to about 20 mg/mL, from about 20 mg/mL to about 25 mg/mL, from about 25 mg/mL to about 30 mg/mL, from about 30 mg/mL to about 35 mg/mL, from about 35 mg/mL to about 40 mg/mL, from about 40 mg/mL to about 45 mg/mL, about 45 mg/mL to about 50 mg/mL, from about 50 mg/mL to about 55 mg/mL, from about 55 mg/mL to about 60 mg/mL, from about 60 mg/mL to about 65 mg/mL, from about 65 mg/mL to about 70 mg/mL, from about 70 mg/mL to about 75 mg/mL, about 75 mg/mL to about 80 mg/mL, from about 80 mg/mL to about 85 mg/mL, from about 85 mg/mL to about 90 mg/mL, from about 90 mg/mL to about 95 mg/mL, or from about 95 mg/mL to about 100 mg/mL.

In some embodiments, a compound or pharmaceutically-acceptable salt thereof is present in a formulation in an amount of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL about 92 mg/mL, about 93 mg/mL, about 94 mg/mL, about 95 mg/mL, about 96 mg/mL, about 97 mg/mL, about 98 mg/mL, about 99 mg/mL, or about 100 mg/mL.

A formulation that is disclosed herein can be made more soluble by the addition of an additive or agent. The improvement of solubility of the formulation can increase by about 5%, about 10%, about 15%, about 20%, about 25%, about 30%, about 35%, about 40%, about 45%, about 50%, about 55%, about 60%, about 65%, about 70%, about 75% about 80%, about 85%, about 90%, about 95%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 450%, or about 500%.

A formulation disclosed herein can be stable for about 1 day, about 2 days, about 3 days, about 4 days, about 5 days, about 6 days, about 7 days, about 8 days, about 9 days, about 10 days, about 2 weeks, about 4 weeks, about 6 weeks, about 8 weeks, about 10 weeks, about 12 weeks, about 3 months, about 4 months, about 5 months, about 6 months, about 7 months, about 8 months, about 9 months, about 10 months, about 11 months, or about one year. A formulation disclosed herein can be stable, for example, at about 0° C., about 5° C., about 10° C., about 15° C., about 20° C., about 25° C., about 30° C., about 35° C., about 40° C., about 45° C., about 50° C., about 60° C., about 70° C., or about 80° C.

Alcohols.

A non-limiting example of a solubilizing agent includes an organic solvent. Non-limiting examples of organic solvents include alcohols, for example, $C_1$-$C_4$ linear alkyl, $C_3$-$C_4$ branched alkyl, ethanol, ethylene glycol, glycerin, 2-hydroxypropanol, propylene glycol, maltitol, sorbitol, xylitol; substituted or unsubstituted aryl, and benzyl alcohol.

Cyclodextrins.

Non-limiting examples of cyclodextrins include β-cyclodextrin, methyl β-cyclodextrin, 2-hydroxypropyl-β-cyclodextrin, sulfobutyl ether-β-cyclodextrin sodium salt, hydroxyethyl-β-cyclodextrin (HE-β-CD), heptakis (2,6-di-O-methyl)-β-cyclodextrin (DMβCD), and 2-hydroxypropyl-β-cyclodextrin. A cyclodextrin can possess a large cyclic structure with a channel passing through the center of the structure. The interior of the cyclodextrin can be hydrophobic, and interact favorably with hydrophobic molecules. The exterior of the cyclodextrin can be highly hydrophilic owing to the several hydroxyl groups exposed to bulk solvent. Capture of a hydrophobic molecule, such as a compound disclosed herein, in the channel of the cyclodextrin can result in the formation of a complex stabilized by non-covalent hydrophobic interactions. The complex can be soluble in water, and carry the captured hydrophobic molecule into the bulk solvent.

The disclosed solubilizing systems comprise 2-hydroxypropyl-beta-cyclodextrin (HPβCD). 2-Hydroxypropyl-β-cyclodextrin [CAS No. 128446-35-5] is commercially available as Cavitron™. 2-Hydroxypropyl-β-cyclodextrin, also described known as hydroxypropyl-β-cyclodextrin, 2-hydroxypropyl-beta-cyclodextrin, hydroxypropyl-beta-cyclodextrin or HPβCD, can be represented by either of the following formulae:

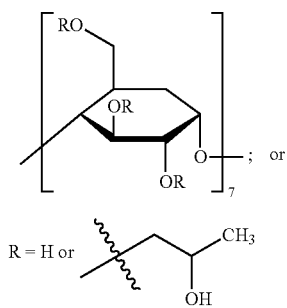

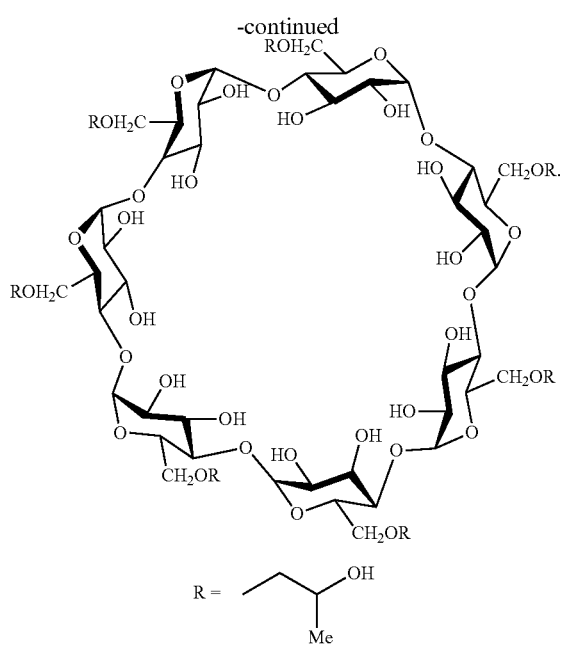

The average molecular weight of Cavitron™, is approximately 1396 Da, wherein the average degree of substitution is from about 0.5 to about 1.3 units of 2-hydroxypropyl per ring glucose unit.

In one embodiment, a formulation disclosed herein can comprise a ratio of about 20 parts of a compound herein or a pharmaceutically-acceptable salt thereof to about 1 part solubilizing system (about 20:about 1), to about 1 part of the compound herein or a pharmaceutically-acceptable salt thereof to about 20 parts solubilizing system (about 1:about 20). For example, a formulation containing about 100 mg of a compound herein or a pharmaceutically-acceptable salt thereof can contain from about 5 mg to about 2000 mg of a solubilizing agent, such as a cyclodextrin. In another embodiment, the ratio can be based on number, or moles, or compound compared to number, or moles, of the solubilizing system.

The following are non-limiting examples of ratios of a compound herein and a solubilizing agent, such as a cyclodextrin. The following examples alternatively describe the ratio of a solubilizing agent, such as a cyclodextrin, and a compound herein. The ratio can be: about 20:about 1; about 19.9:about 1; about 19.8:about 1; about 19.7:about 1; about 19.6:about 1; about 19.5:about 1; about 19.4:about 1; about 19.3:about 1; about 19.2:about 1; about 19.1:about 1; about 19:about 1; about 18.9:about 1; about 18.8:about 1; about 18.7:about 1; about 18.6:about 1; about 18.5:about 1; about 18.4:about 1; about 18.3:about 1; about 18.2:about 1; about 18.1:about 1; about 18:about 1; about 17.9:about 1; about 17.8:about 1; about 17.7:about 1; about 17.6:about 1; about 17.5:about 1; about 17.4:about 1; about 17.3:about 1; about 17.2:about 1; about 17.1:about 1; about 17:about 1; about 16.9:about 1; about 16.8:about 1; about 16.7:about 1; about 16.6:about 1; about 16.5:about 1; about 16.4:about 1; about 16.3:about 1; about 16.2:about 1; about 16.1:about 1; about 16:about 1; about 15.9:about 1; about 15.8:about 1; about 15.7:about 1; about 15.6:about 1; about 15.5:about 1; about 15.4:about 1; about 15.3:about 1; about 15.2:about 1; about 15.1:about 1; about 15:about 1; about 14.9:about 1; about 14.8:about 1; about 14.7:about 1; about 14.6:about 1; about 14.5:about 1; about 14.4:about 1; about 14.3:about 1; about 14.2:about 1; about 14.1:about 1; about 14:about 1; about 13.9:about 1; about 13.8:about 1; about 13.7:about 1; about 13.6:about 1; about 13.5:about 1; about 13.4:about 1; about 13.3:about 1; about 13.2:about 1; about 13.1:about 1; about 13:about 1; about 12.9:about 1; about 12.8:about 1; about 12.7:about 1; about 12.6:about 1; about 12.5:about 1; about 12.4:about 1; about 12.3:about 1; about 12.2:about 1; about 12.1:about 1; about 12:about 1; about 11.9:about 1; about 11.8:about 1; about 11.7:about 1; about 11.6:about 1; about 11.5:about 1; about 11.4:about 1; about 11.3:about 1; about 11.2:about 1; about 11.1:about 1; about 11:about 1; about 10.9:about 1; about 10.8:about 1; about 10.7:about 1; about 10.6:about 1; about 10.5:about 1; about 10.4:about 1; about 10.3:about 1; about 10.2:about 1; about 10.1:about 1; about 10:about 1; about 9.9:about 1; about 9.8:about 1; about 9.7:about 1; about 9.6:about 1; about 9.5 about 1; about 9.4 about 1; about 9.3:about 1; about 9.2:about 1; about 9.1: about 1; about 9:about 1; about 8.9:about 1; about 8.8:about 1; about 8.7:about 1; about 8.6:about 1; about 8.5:about 1; about 8.4:about 1; about 8.3:about 1; about 8.2:about 1; about 8.1:about 1; about 8:about 1; about 7.9:about 1; about 7.8:about 1; about 7.7:about 1; about 7.6:about 1; about 7.5:about 1; about 7.4:about 1; about 7.3:about 1; about 7.2:about 1; about 7.1:about 1; about 7:about 1; about 6.9:about 1; about 6.8:about 1; about 6.7:about 1; about 6.6:about 1; about 6.5:about 1; about 6.4:about 1; about 6.3:about 1; about 6.2:about 1; about 6.1:about 1; about 6:about 1; about 5.9 about 1; about 5.8 about 1; about 5.7 about 1; about 5.6:about 1; about 5.5:about 1; about 5.4: about 1; about 5.3:about 1; about 5.2:about 1; about 5.1: about 1; about 5:about 1; about 4.9:about 1; about 4.8:about 1; about 4.7:about 1; about 4.6:about 1; about 4.5:about 1; about 4.4:about 1; about 4.3:about 1; about 4.2:about 1; about 4.1:about 1; about 4:about 1; about 3.9:about 1; about 3.8:about 1; about 3.7:about 1; about 3.6:about 1; about 3.5:about 1; about 3.4:about 1; about 3.3:about 1; about 3.2:about 1; about 3.1:about 1; about 3:about 1; about 2.9:about 1; about 2.8:about 1; about 2.7:about 1; about 2.6:about 1; about 2.5:about 1; about 2.4:about 1; about 2.3:about 1; about 2.2:about 1; about 2.1:about 1; about 2:about 1; about 1.9:about 1; about 1.8:about 1; about 1.7:about 1; about 1.6:about 1; about 1.5:about 1; about 1.4:about 1; about 1.3:about 1; about 1.2:about 1; about 1.1:about 1; or about 1:about 1.

Polyvinylpyrrolidinone.

Another non-limiting example of a solubilizing agent is polyvinylpyrrolidone (PVP), having the formula:

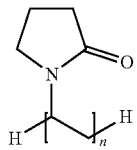

wherein the index n is from about 40 to about 200. PVP's can have an average molecular weight from about 5500 to about 28,000 g/mol. One non-limiting example is PVP-10, having an average molecular weight of approximately 10,000 g/mol.

Polyalkyleneoxides and Ethers Thereof.

Another non-limiting example of solubilizing agents includes polyalkyleneoxides, and polymers of alcohols or polyols. Polymers can be mixed, or contain a single monomeric repeat subunit. For example, polyethylene glycols having an average molecular weight of from about 200 to about 20,000, for example, PEG 200, PEG 400, PEG 600, PEG 1000, PEG 1450, PEG 1500, PEG 4000, PEG 4600, and PEG 8000. In a same embodiment, a composition comprises one or more polyethylene glycols chosen from PEG 400, PEG 1000, PEG 1450, PEG 4600 and PEG 8000.

Other polyalkyleneoxides are polypropylene glycols having the formula:

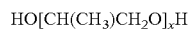

wherein the index x represents the average number of propyleneoxy units in the polymer. The index x can be represented by a whole number or a fraction. For example, a polypropylene glycol having an average molecular weight of 8,000 g/mole (PEG 8000) can be represented by the formulae:

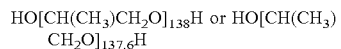

or the polypropylene glycol can be represented by the common, short hand notation: PEG 8000.

Another example of polypropylene glycols can have an average molecular weight from about 1200 g/mol to about 20,000 g/mol, i.e., a polypropylene glycol having an average molecular weight of about 8,000 g/mol, for example, PEG 8000.

Another solubilizing agent is Polysorbate 80 (Tween™ 80), which is an oleate ester of sorbitol and its anhydrides copolymerized with approximately 20 moles of ethylene oxide for each mole of sorbitol and sorbitol anhydrides. Polysorbate 80 is made up of sorbitan mono-9-octadecanoate poly(oxy-1,2-ethandiyl) derivatives.

Solubilizing agents also include poloxamers having the formula:

which are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol.

Excipients.

A pharmaceutical composition of the invention can be a combination of any pharmaceutical compounds described herein with other chemical components, such as carriers, stabilizers, diluents, dispersing agents, suspending agents, thickening agents, or excipients. The pharmaceutical composition facilitates administration of the compound to an organism. Pharmaceutical compositions can be administered in therapeutically-effective amounts as pharmaceutical compositions by various forms and routes including, for example, intravenous, intravitreal, subcutaneous, intramuscular, oral, rectal, aerosol, parenteral, ophthalmic, pulmonary, transdermal, vaginal, otic, nasal, and topical administration.

A pharmaceutical composition can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated readily by combining the active compounds with pharmaceutically-acceptable carriers or excipients.

Such carriers can be used to formulate tablets, powders, pills, dragees, capsules, liquids, gels, syrups, elixirs, slurries, suspensions and the like, for oral ingestion by a subject.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum 24yrazi, talc, polyvinylpyrrolidone, carbopol gel, polyethylene glycol, or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can contain the active ingredients in admixture with filler such as lactose, binders such as starches, or lubricants such as talc or magnesium stearate and, stabilizers. In soft capsules, the active compounds can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Formulations suitable for transdermal administration of the active compounds can employ transdermal delivery devices and transdermal delivery patches, and can be lipophilic emulsions or buffered aqueous solutions, dissolved or dispersed in a polymer or an adhesive. Such patches can be constructed for continuous, pulsatile, or on demand delivery of pharmaceutical compounds. Transdermal delivery can be accomplished by means of iontophoretic patches. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically-acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin or the eye.

For administration by inhalation, the active compounds can be in a form as an aerosol, a mist, or a powder. Pharmaceutical compositions are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compounds described herein can be manufactured, for example, by mixing, dissolving, granulating, dragee-making, levigating, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. The methods and pharmaceutical compositions described herein include the use of crystalline forms (also known as polymorphs), and active metabolites of these compounds having the same type of activity.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

The invention can be administered as eye drops. The average volume of each drop administered to a subject can be about 5 µl, about 10 µl, about 15 µl, about 20 µl, about 30 µl, about 40 µl, about 50 µl, about 60 µl, about 70 µl, about 80 µl, about 90 µl, or about 100 µl. The eye drops can contain about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% of a compound of the invention. The drops can contain about 1 mg/ml, about 5 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 60 mg/ml, about 70 mg/ml, about 80 mg/ml, about 90 mg/ml, about 100 mg/ml, about 120 mg/ml, about 140 mg/ml, about 160 mg/ml, about 180 mg/ml, or about 200 mg/ml of a compound of the invention. The individual dose administered to a subject can be about 0.5 µg, about 1 µg, about 2 µg, about 3 µg, about 4 µg, about 5 µg, about 6 µg, about 7 µg, about 8 µg, about 9 µg, about 10 µg, about 20 µg, about 30 µg, about 40 µg, about 50 µg, about 60 µg, about 70 µg, about 80 µg, about 90 µg, about 100 µg, about 150 µg, about 200 µg, about 250 µg, about 300 µg, about 350 µg, about 400 µg, about 450 µg, about 500 µg, about 550 µg, about 600 µg, about 650 µg, about 700 µg, about 750 µg, about 800 µg, about 850 µg, about 900 µg, about 950 µg, about 1 mg, about 1.1 mg, about 1.2 mg, 1.3 mg, about 1.4 mg, about 1.5 mg, about 1.6 mg, about 1.7 mg, about 1.8 mg, about 1.9 mg, or about 2 mg of a compound of the invention. In some embodiments, more than one drop can be administered to an eye either at one time or at multiple times throughout the day.

Non-limiting examples of excipients suitable for use in eye drops include cyclodextrin, α-cyclodextrin, β-cyclodextrin, 2-hydroxypropyl-β-cyclodextrin (HP-β-CD), random methyl-β-cyclodextrin (RM-β-CD), sulfobutyl ether β-cyclodextrin (SBE-β-CD), γ-cyclodextrin, hydroxypropyl-γ-cyclodextrin (HP-γ-CD), hydroxyethyl-β-cyclodextrin (HE-β-CD), heptakis (2,6-di-O-methyl)-β-cyclodextrin (DMβCD), saline, sodium bisulfate, metabisulfite, ascorbic acid, acetylcysteine, benzalkonium chloride, boric acid, hyaluronic acid, hypromellose, propylene glycol, potassium sorbate, sodium chloride, sodium acetate, disodium edetate, sodium dihydrogen phosphate monohydrate, disodium phosphate, sodium hydroxide, hydrochloric acid, glycerol, mannitol, trometamol, tyloxapol, and any combination thereof.

Non-limiting examples of pharmaceutically-acceptable excipients suitable for use in the invention include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, anti-microbial agents, plant cellulosic material and spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

The disclosed compositions can optionally comprise from about 0.001% to about 0.005% weight by volume pharmaceutically-acceptable preservatives. One non-limiting example of a suitable preservative is benzyl alcohol.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

The disclosed methods include administration of a Tie-2 activator, or a pharmaceutically-acceptable salt thereof, in combination with a pharmaceutically-acceptable carrier. The carrier can be selected to minimize any degradation of the active ingredient and to minimize any adverse side effects in the subject.

The Tie-2 activator or a pharmaceutically-acceptable salt thereof herein can be conveniently formulated into pharmaceutical compositions composed of one or more pharmaceutically-acceptable carriers. See e.g., *Remington's Pharmaceutical Sciences*, latest edition, by E. W. Martin Mack Pub. Co., Easton, PA, which discloses typical carriers and conventional methods of preparing pharmaceutical compositions that can be used in conjunction with the preparation of formulations of the compound described herein and which is incorporated by reference herein. Such pharmaceuticals can be standard carriers for administration of compositions to humans and non-humans, including solutions such as sterile water, saline, and buffered solutions at physiological pH. Other compositions can be administered according to standard procedures. For example, pharmaceutical compositions can also include one or more additional active ingredients such as antimicrobial agents, anti-inflammatory agents, and anesthetics.

Non-limiting examples of pharmaceutically-acceptable carriers include saline solution, Ringer's solution and dextrose solution. The pH of the solution can be from about 5 to about 8, and can be from about 7 to about 7.5. Further carriers include sustained release preparations such as semipermeable matrices of solid hydrophobic polymers containing the Tie-2 activator or a pharmaceutically-acceptable salt thereof, where the matrices are in the form of shaped articles, such as films, liposomes, microparticles, and microcapsules.

The disclosed methods relate to administering the Tie-2 activator or a pharmaceutically-acceptable salt thereof as part of a pharmaceutical composition. In various embodiments, compositions of the invention can comprise a liquid comprising an active agent in solution, in suspension, or both. Liquid compositions can include gels. In one embodiment, the liquid composition is aqueous. Alternatively, the composition can take form of an ointment. In another embodiment, the composition is an in situ gellable aqueous composition. In some embodiments, the composition is an in situ gellable aqueous solution.

Pharmaceutical formulations can include additional carriers, as well as thickeners, diluents, buffers, preservatives, and surface active agents in addition to the compounds disclosed herein. Pharmaceutical formulations can also include one or more additional active ingredients such as antimicrobial agents, anti-inflammatory agents, anesthetics, and the like.

An excipient can fill a role as simple and direct as being an inert filler, or an excipient as used herein can be part of a pH stabilizing system or coating to insure delivery of the ingredients safely to the stomach.

The Tie-2 activator or a pharmaceutically-acceptable salt thereof can also be present in liquids, emulsions, or suspensions for delivery of active therapeutic agents in aerosol form to cavities of the body such as the nose, throat, or bronchial passages. The ratio of Tie-2 activator or a pharmaceutically-acceptable salt thereof to the other compounding agents in these preparations can vary as the dosage form requires.

Depending on the intended mode of administration, the pharmaceutical compositions administered as part of the disclosed methods can be in the form of solid, semi-solid or liquid dosage forms, such as, for example, tablets, suppositories, pills, capsules, powders, liquids, suspensions, lotions, creams, gels, for example, in unit dosage form suitable for single administration of a precise dosage. The compositions can contain, as noted above, an effective amount of the Tie-2 activator or a pharmaceutically-acceptable salt thereof in combination with a pharmaceutically-acceptable carrier and, in addition, can include other medicinal agents, pharmaceutical agents, carriers, adjuvants, diluents, etc.

For solid compositions, nontoxic solid carriers include, for example, pharmaceutical grades of mannitol, lactose, starch, magnesium stearate, sodium saccharin, talc, cellulose, glucose, sucrose, and magnesium carbonate. In one embodiment, a composition comprising the Tie-2 activator or a pharmaceutically-acceptable salt thereof in an amount of approximately 4 mg per 0.1 mL liquid is prepared. The liquid phase comprises sterile water and an appropriate amount of a saccharide or polysaccharide.

Pharmaceutical Compositions.

Pharmaceutical compositions containing the compounds described herein can be administered for prophylactic or therapeutic treatments. Compositions can contain any number of active agents. In therapeutic applications, the compositions can be administered to a subject already suffering from a disease or condition, in an amount sufficient to cure or at least partially arrest the symptoms of the disease or condition, or to cure, heal, improve, reduce, lessen or ameliorate the disease or condition. Compounds can also be administered to lessen or reduce a likelihood of developing, contracting, or worsening a condition. Amounts effective for this use can vary based on the severity and course of the disease or condition, previous therapy, the subject's health status, weight, response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills or injections. The compounds can be packed together or separately, in a single package or in a plurality of packages. One or all of the therapeutic agents can be given in multiple doses. If not simultaneous, the timing between the multiple doses can vary.

Compounds and compositions of the invention can be packaged as a kit. In some embodiments, the invention provides a kit comprising a compound disclosed herein, or a pharmaceutically-acceptable salt thereof, and written instructions on use of the kit in the treatment of a condition described herein. In some embodiments, the invention provides a kit comprising a compound disclosed herein, or a pharmaceutically-acceptable salt thereof, an antibody, and written instructions on use of the kit in the treatment of a condition described herein.

The compounds described herein can be administered before, during, or after the occurrence of a disease or condition, and the timing of administering the composition containing a compound can vary. For example, the compounds can be used as a prophylactic and can be administered continuously to subjects with a propensity to conditions or diseases in order to lessen or reduce a likelihood of the occurrence of the disease or condition. The compounds and compositions can be administered to a subject during or as soon as possible after the onset of the symptoms. The administration of the compounds can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for parenteral injection can be presented in unit dosage form, for example, in ampoules, or in multi-dose containers with a preservative.

A Tie-2 activator described herein can be present in a composition in a range of from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 35 mg to about 40 mg, from about 40 mg to about 45 mg, from about 45 mg to about 50 mg, from about 50 mg to about 55 mg, from about 55 mg to about 60 mg, from about 60 mg to about 65 mg, from about 65 mg to about 70 mg, from about 70 mg to about 75 mg, from about 75 mg to about 80 mg, from about 80 mg to about 85 mg, from about 85 mg to about 90 mg, from about 90 mg to about 95 mg, from about 95 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, or from about 250 mg to about 300 mg.

A Tie-2 activator described herein can be present in a composition in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, or about 300 mg.

Treatment of Subjects with a Tie-2 Activator.

The invention discloses methods for treating a subject afflicted with elevated intraocular pressure with an activator of Tie-2. The subject can be a human. Treatment can include treating a human in a clinical trial. A treatment can comprise administering to a subject a pharmaceutical composition comprising one or more of the activators of Tie-2 described throughout the disclosure. A treatment can comprise administrating to a subject a therapy that promotes the phosphorylation of a Tie-2 molecule.

In some embodiments, the invention provides a Tie-2 activator for use in treatment of elevated intraocular pressure, ocular hypertension, or glaucoma. In some embodiments, the invention provides a Tie-2 activator for use in the manufacture of a medicament for the treatment of elevated intraocular pressure, ocular hypertension, or glaucoma.

In some embodiments, the intraocular pressure or ocular hypertension is caused by a glaucoma. In some embodiments, the glaucoma is a primary open angle glaucoma.

Non-limiting examples of possible subjects for administration include the following. Subjects can be humans, non-human primates such as chimpanzees, and other apes and monkey species; farm animals such as cattle, horses, sheep, goats, and swine; domestic animals such as rabbits, dogs, and cats; and laboratory animals including rats, mice, and guinea pigs. A subject can be of any age. Subjects can be, for example, elderly adults, adults, adolescents, pre-adolescents, children, toddlers, and infants.

Some conditions can lead to an increase in the levels of Ang-2, altering the ratio of Ang-1/Ang-2 in circulation. In some aspects, a therapy can improve the outcome of a disease state, including increased intraocular pressure or glaucoma, by altering the ratio of Ang-1/Ang-2 in circulation. A therapy can provide an Ang-1/Ang-2 ratio or an Ang-2/Ang-1 ratio of about 1:about 1, about 2:about 1, about 3:about 1, about 4:about 1, about 5:about 1, about 6:about 1, about 7:about 1, about 8:about 1, about 9:about 1, or about 10:about 1.

Pharmacodynamic and Pharmacokinetic Parameters.

Pharmacokinetic and pharmacodynamic data can be obtained by various experimental techniques. Appropriate pharmacokinetic and pharmacodynamic profile components describing a particular composition can vary due to variations in the metabolism of an activator of Tie-2 in different subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined by calculating the average of all subject's measurements for each parameter measured.

A therapy can be used to inhibit a specific biological or biochemical function at a lower dosage. A dose can be modulated to achieve a desired pharmacokinetic or pharmacodynamics profile, such as a desired or effective blood profile, as described herein. The half maximum inhibitory concentration ($IC_{50}$) is a measure of the effectiveness of a substance in inhibiting a specific biological or biochemical function. This quantitative measure indicates how much of a particular drug or compound is needed to inhibit a given biological process, such as the activity of HPTPβ by half. Combination drug treatments can present lower $IC_{50}$ values as compared to monotherapies.

The outcome of treating a human subject with a therapy can be measured by calculating pharmacodynamic and pharmacokinetic parameters. Non-limiting examples of pharmacodynamic and pharmacokinetic parameters that can be used to determine the effect of treatment of a subject with a therapy of the disclosure include: a) the amount of drug administered, which can be represented as a dose D; b) the dosing interval, which can be represented as $\tau$; c) the apparent volume in which a drug is distributed, which can be represented as a volume of distribution $V_d$, where $V_d=D/C_0$; d) the amount of drug in a given volume of tissue, which can be represented as concentration $C_0$ or $C_{ss}$, where $C_0$ or $C_{ss}=D/Vd$; e) the half-life of a drug $t_{1/2}$, where $t_{1/2}=\ln(2)/k_e$; f) the rate at which a drug is removed from the body $k_e$, where $k_e=\ln(2)/t_{1/2}=CL/V_d$; g) the rate of infusion required to balance the equation $K_{in}$, where $K_{in}=C_{ss} \cdot CL$; h) the integral of the concentration-time curve after administration of a single dose, which can be represented as $AUC_{0-\infty}$, wherein $\int_0^\infty C\,dt$, or in steady-state, which can be represented as $AUC\tau_{,ss}$, wherein $\int_t^{t+\tau} C\,dt$; i) the volume of tissue cleared of the drug per unit time, which can be represented as CL (clearance), wherein $CL=V_d \cdot k_e=D/AUC$; j) the systemically available fraction of a drug, which can be represented as f, where $$f = \frac{AUCpo.Div}{AUCiv.Dpo};$$

the peak tissue concentration of a drug after administration $C_{max}$; l) the time taken by a drug to reach $C_{max}$, $t_{max}$; m) the lowest concentration that a drug reaches before the next dose is administered $C_{min}$; and n) the peak trough fluctuation within one dosing interval at steady state, which can be represented as $$\% \, PTF = 100 \cdot \frac{(Cmax, ss - Cmin, ss)}{Cav, ss} \text{ where } C_{av,ss} = \frac{AUC\tau, ss}{\tau}.$$

The pharmacokinetics parameters can be any parameters suitable for describing the tissue concentration profiles of a therapy of the disclosure. For example, the pharmacokinetics profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The pharmacokinetic parameters can be any parameters suitable for describing a small molecule activator of Tie-2. The $C_{max}$ can be, for example, not less than about 1 ng/mL; not less than about 2 ng/mL; not less than about 3 ng/mL; not less than about 4 ng/mL; not less than about 5 ng/mL; not less than about 6 ng/mL; not less than about 7 ng/mL; not less than about 8 ng/mL; not less than about 9 ng/mL; not less than about 10 ng/mL; not less than about 15 ng/mL; not less than about 20 ng/mL; not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; or any other $C_{max}$ appropriate for describing a pharmacokinetic profile of an activator of Tie-2 described herein. The $C_{max}$ can be, for example, about 1 ng/mL to about 5,000 ng/mL; about 1 ng/mL to about 4,500 ng/mL; about 1 ng/mL to about 4,000 ng/mL; about 1 ng/mL to about 3,500 ng/mL; about 1 ng/mL to about 3,000 ng/mL; about 1 ng/mL to about 2,500 ng/mL; about 1 ng/mL to about 2,000 ng/mL; about 1 ng/mL to about 1,500 ng/mL; about 1 ng/mL to about 1,000 ng/mL; about 1 ng/mL to about 900 ng/mL; about 1 ng/mL to about 800 ng/mL; about 1 ng/mL to about 700 ng/mL; about 1 ng/mL to about 600 ng/mL; about 1 ng/mL to about 500 ng/mL; about 1 ng/mL to about 450 ng/mL; about 1 ng/mL to about 400 ng/mL; about 1 ng/mL to about 350 ng/mL; about 1 ng/mL to about 300 ng/mL; about 1 ng/mL to about 250 ng/mL; about 1 ng/mL to about 200 ng/mL; about 1 ng/mL to about 150 ng/mL; about 1 ng/mL to about 125 ng/mL; about 1 ng/mL to about 100 ng/mL; about 1 ng/mL to about 90 ng/mL; about 1 ng/mL to about 80 ng/mL; about 1 ng/mL to about 70 ng/mL; about 1 ng/mL to about 60 ng/mL; about 1 ng/mL to about 50 ng/mL; about 1 ng/mL to about 40 ng/mL; about 1 ng/mL to about 30 ng/mL; about 1 ng/mL to about 20 ng/mL; about 1 ng/mL to about 10 ng/mL; about 1 ng/mL to about 5 ng/mL; about 10 ng/mL to about 4,000 ng/mL; about 10 ng/mL to about 3,000 ng/mL; about 10 ng/mL to about 2,000 ng/mL; about 10 ng/mL to about 1,500 ng/mL; about 10 ng/mL to about 1,000 ng/mL; about 10 ng/mL to about 900 ng/mL; about 10 ng/mL to about 800 ng/mL; about 10 ng/mL to about 700 ng/mL; about 10 ng/mL to about 600 ng/mL; about 10 ng/mL to about 500 ng/mL; about 10 ng/mL to about 400 ng/mL; about 10 ng/mL to about 300 ng/mL; about 10 ng/mL to about 200 ng/mL; about 10 ng/mL to about 100 ng/mL; about 10 ng/mL to about 50 ng/mL; about 25 ng/mL to about 500 ng/mL; about 25 ng/mL to about 100 ng/mL; about 50 ng/mL to about 500 ng/mL; about 50 ng/mL to about 100 ng/mL; about 100 ng/mL to about 500 ng/mL; about 100 ng/mL to about 400 ng/mL; about 100 ng/mL to about 300 ng/mL; or about 100 ng/mL to about 200 ng/mL.

The $T_{max}$ of an activator of Tie-2 described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of an activator of Tie-2 described herein. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours.

The $AUC_{(0-inf)}$ or $AUC_{(last)}$ of an activator of Tie-2 described herein can be, for example, not less than about 1 ng·hr/mL, not less than about 5 ng·hr/mL, not less than about 10 ng·hr/mL, not less than about 20 ng·hr/mL, not less than about 30 ng·hr/mL, not less than about 40 ng·hr/mL, not less than about 50 ng·hr/mL, not less than about 100 ng·hr/mL, not less than about 150 ng·hr/mL, not less than about 200 ng·hr/mL, not less than about 250 ng·hr/mL, not less than about 300 ng·hr/mL, not less than about 350 ng·hr/mL, not less than about 400 ng·hr/mL, not less than about 450 ng·hr/mL, not less than about 500 ng·hr/mL, not less than about 600 ng·hr/mL, not less than about 700 ng·hr/mL, not less than about 800 ng·hr/mL, not less than about 900 ng·hr/mL, not less than about 1000 ng·hr/mL, not less than about 1250 ng·hr/mL, not less than about 1500 ng·hr/mL, not less than about 1750 ng·hr/mL, not less than about 2000 ng·hr/mL, not less than about 2500 ng·hr/mL, not less than about 3000 ng·hr/mL, not less than about 3500 ng·hr/mL, not less than about 4000 ng·hr/mL, not less than about 5000 ng·hr/mL, not less than about 6000 ng·hr/mL, not less than about 7000 ng·hr/mL, not less than about 8000 ng·hr/mL, not less than about 9000 ng·hr/mL, not less than about 10,000 ng·hr/mL, or any other $AUC_{(0-inf)}$ appropriate for describing a pharmacokinetic profile of a compound described herein. The $AUC_{(0-inf)}$ of an activator of Tie-2 can be, for example, about 1 ng·hr/mL to about 10,000 ng·hr/mL; about 1 ng·hr/mL to about 10 ng·hr/mL; about 10 ng·hr/mL to about 25 ng·hr/mL; about 25 ng·hr/mL to about 50 ng·hr/mL; about 50 ng·hr/mL to about 100 ng·hr/mL; about 100 ng·hr/mL to about 200 ng·hr/mL; about 200 ng·hr/mL to about 300 ng·hr/mL; about 300 ng·hr/mL to about 400 ng·hr/mL; about 400 ng·hr/mL to about 500 ng·hr/mL; about 500 ng·hr/mL to about 600 ng·hr/mL; about 600 ng·hr/mL to about 700 ng·hr/mL; about 700 ng·hr/mL to about 800 ng·hr/mL; about 800 ng·hr/mL to about 900 ng·hr/mL; about 900 ng·hr/mL to about 1,000 ng·hr/mL; about 1,000 ng·hr/mL to about 1,250 ng·hr/mL; about 1,250 ng·hr/mL to about 1,500 ng·hr/mL; about 1,500 ng·hr/mL to about 1,750 ng·hr/mL; about 1,750 ng·hr/mL to about 2,000 ng·hr/mL; about 2,000 ng·hr/mL to about 2,500 ng·hr/mL; about 2,500 ng·hr/mL to about 3,000 ng·hr/mL; about 3,000 ng·hr/mL to about 3,500 ng·hr/mL; about 3,500 ng·hr/mL to about 4,000 ng·hr/mL; about 4,000 ng·hr/mL to about 4,500 ng·hr/mL; about 4,500 ng·hr/mL to about 5,000 ng·hr/mL; about 5,000 ng·hr/mL to about 5,500 ng·hr/mL; about 5,500 ng·hr/mL to about 6,000 ng·hr/mL; about 6,000 ng·hr/mL to about 6,500 ng·hr/mL; about 6,500 ng·hr/mL to about 7,000 ng·hr/mL; about 7,000 ng·hr/mL to about 7,500 ng·hr/mL; about 7,500 ng·hr/mL to about 8,000 ng·hr/mL; about 8,000 ng·hr/mL to about 8,500 ng·hr/mL; about 8,500 ng·hr/mL to about 9,000 ng·hr/mL; about 9,000 ng·hr/mL to about 9,500 ng·hr/mL; or about 9,500 ng·hr/mL to about 10,000 ng·hr/mL.

The concentration in a tissue or fluid of an eye of an activator of Tie-2 described herein can be determined, for example, the intraocular concentration or amount. Non-limiting examples of tissues of the eye include cornea, iris, zonule fibers, sclera, lens, vitreous humor, fovea, choroid, ciliary muscle, aqueous humor, retina, and optic nerve. The concentration in the tissue of the eye of an activator of Tie-2 described herein can be, for example, about 0.1 nanograms per gram (ng/g), about 0.2 ng/g, about 0.3 ng/g, about 0.4 ng/g, about 0.5 ng/g, about 0.6 ng/g, about 0.7 ng/g, about 0.9 ng/g, about 1 ng/g, about 2 ng/g, about 3 ng/g, about 4 ng/g, about 5 ng/g, about 6 ng/g, about 7 ng/g, about 9 ng/g, about 10 ng/g, about 20 ng/g, about 30 ng/g, about 40 ng/g, about 50 ng/g, about 60 ng/g, about 70 ng/g, about 90 ng/g, about 0.1 micrograms per gram (μg/g), about 0.2 μg/g, about 0.3 μg/g, about 0.4 μg/g, about 0.5 μg/g, about 0.6 μg/g, about 0.7 μg/g, about 0.9 μg/g, about 1 μg/g, about 2 μg/g, about 3 μg/g, about 4 μg/g, about 5 μg/g, about 6 μg/g, about 7 μg/g, about 9 μg/g, about 10 μg/g, about 20 μg/g, about 30 μg/g, about 40 μg/g, about 50 μg/g, about 60 μg/g, about 70 μg/g, about 90 μg/g, about 0.1 milligrams per gram (mg/g), about 0.2 mg/g, about 0.3 mg/g, about 0.4 mg/g, about 0.5 mg/g, about 0.6 mg/g, about 0.7 mg/g, about 0.9 mg/g, or about 1 mg/g tissue weight.

The concentration in the tissue of the eye of an activator of Tie-2 described herein can be, for example, from about 0.1 ng/g to about 0.2 ng/g, from about 0.2 ng/g to about 0.3 ng/g, from about 0.3 ng/g to about 0.4 ng/g, from about 0.4 ng/g to about 0.5 ng/g, from about 0.5 ng/g to about 0.6 ng/g, from about 0.6 ng/g to about 0.7 ng/g, from about 0.7 ng/g to about 0.8 ng/g, from about 0.8 ng/g to about 0.9 ng/g, from about 0.9 ng/g to about 1 ng/g, from about 1 ng/g to about 2 ng/g, from about 2 ng/g to about 3 ng/g, from about 3 ng/g to about 4 ng/g, from about 4 ng/g to about 5 ng/g, from about 5 ng/g to about 6 ng/g, from about 6 ng/g to about 7 ng/g, from about 7 ng/g to about 8 ng/g, from about 8 ng/g to about 9 ng/g, from about 9 ng/g to about 10 ng/g, from about 10 ng/g to about 20 ng/g, from about 20 ng/g to about 30 ng/g, from about 30 ng/g to about 40 ng/g, from about 40 ng/g to about 50 ng/g, from about 50 ng/g to about 60 ng/g, from about 60 ng/g to about 70 ng/g, from about 70 ng/g to about 80 ng/g, from about 80 ng/g to about 90 ng/g, from about 90 ng/g to about 0.1 μg/g, from about 0.1 μg/g to about 0.2 μg/g, from about 0.2 μg/g to about 0.3 μg/g, from about 0.3 μg/g to about 0.4 μg/g, from about 0.4 μg/g to about 0.5 μg/g, from about 0.5 μg/g to about 0.6 μg/g, from about 0.6 μg/g to about 0.7 μg/g, from about 0.7 μg/g to about 0.8 μg/g, from about 0.8 μg/g to about 0.9 μg/g, from about 0.9 μg/g to about 1 μg/g, from about 1 μg/g to about 2 μg/g, from about 2 μg/g to about 3 μg/g, from about 3 μg/g to about 4 μg/g, from about 4 μg/g to about 5 μg/g, from about 5 μg/g to about 6 μg/g, from about 6 μg/g to about 7 μg/g, from about 7 μg/g to about 8 μg/g, from about 8 μg/g to about 9 μg/g, from about 9 μg/g to about 10 μg/g, from about 10 μg/g to about 20 μg/g, from about 20 μg/g to about 30 μg/g, from about 30 μg/g to about 40 μg/g, from about 40 μg/g to about 50 μg/g, from about 50 μg/g to about 60 μg/g, from about 60 μg/g to about 70 μg/g, from about 70 μg/g to about 80 μg/g, from about 80 μg/g to about 90 μg/g, from about 90 μg/g to about 0.1 mg/g, from about 0.1 mg/g to about 0.2 mg/g, from about 0.2 mg/g to about 0.3 mg/g, from about 0.3 mg/g to about 0.4 mg/g, from about 0.4 mg/g to about 0.5 mg/g, from about 0.5 mg/g to about 0.6 mg/g, from about 0.6 mg/g to about 0.7 mg/g, from about 0.7 mg/g to about 0.8 mg/g, from about 0.8 mg/g to about 0.9 mg/g, or from about 0.9 mg/g to about 1 mg/g tissue weight.

Administration of a Tie-2 activator to the eye can reduce the intraocular pressure, for example, by about 0.1 mmHg, about 0.2 mmHg, about 0.3 mmHg, about 0.4 mmHg, about 0.5 mmHg, about 0.6 mmHg, about 0.7 mmHg, about 0.8 mmHg, about 0.9 mmHg, about 1 mmHg, about 1.1 mmHg, about 1.2 mmHg, about 1.3 mmHg, about 1.4 mmHg, about 1.5 mmHg, about 1.6 mmHg, about 1.7 mmHg, about 1.8 mmHg, about 1.9 mmHg, about 2 mmHg, about 2.1 mmHg, about 2.2 mmHg, about 2.3 mmHg, about 2.4 mmHg, about 2.5 mmHg, about 2.6 mmHg, about 2.7 mmHg, about 2.8 mmHg, about 2.9 mmHg, about 3 mmHg, about 3.1 mmHg, about 3.2 mmHg, about 3.3 mmHg, about 3.4 mmHg, about 3.5 mmHg, about 3.6 mmHg, about 3.7 mmHg, about 3.8 mmHg, about 3.9 mmHg, about 4 mmHg, about 4.1 mmHg, about 4.2 mmHg, about 4.3 mmHg, about 4.4 mmHg, about 4.5 mmHg, about 4.6 mmHg, about 4.7 mmHg, about 4.8 mmHg, about 4.9 mmHg, about 5 mmHg, about 5.1 mmHg, about 5.2 mmHg, about 5.3 mmHg, about 5.4 mmHg, about 5.5 mmHg, about 5.6 mmHg, about 5.7 mmHg, about 5.8 mmHg, about 5.9 mmHg, about 6 mmHg, about 6.1 mmHg, about 6.2 mmHg, about 6.3 mmHg, about 6.4 mmHg, about 6.5 mmHg, about 6.6 mmHg, about 6.7 mmHg, about 6.8 mmHg, about 6.9 mmHg, about 7 mmHg, about 7.1 mmHg, about 7.2 mmHg, about 7.3 mmHg, about 7.4 mmHg, about 7.5 mmHg, about 7.6 mmHg, about 7.7 mmHg, about 7.8 mmHg, about 7.9 mmHg, about 8 mmHg, about 8.1 mmHg, about 8.2 mmHg, about 8.3 mmHg, about 8.4 mmHg, about 8.5 mmHg, about 8.6 mmHg, about 8.7 mmHg, about 8.8 mmHg, about 8.9 mmHg, about 9 mmHg, about 9.1 mmHg, about 9.2 mmHg, about 9.3 mmHg, about 9.4 mmHg, about 9.5 mmHg, about 9.6 mmHg, about 9.7 mmHg, about 9.8 mmHg, about 9.9 mmHg, about 10 mmHg, about 11 mmHg, about 12 mmHg, about 13 mmHg, about 14 mmHg, about 15 mmHg, about 16 mmHg, about 17 mmHg, about 18 mmHg, about 19 mmHg, or about 20 mmHg Administration of a Tie-2 activator to the eye can reduce the intraocular pressure, for example, by at least 20 mmHg, by about 0.1 mmHg to about 20 mmHg, by about 0.1 mmHg to about 15 mmHg, by about 0.1 mmHg to about 10 mmHg, by about 0.1 mmHg to about 9 mmHg, by about 0.1 mmHg to about 8 mmHg, by about 0.1 mmHg to about 7 mmHg, by about 0.1 mmHg to about 6 mmHg, by about 0.1 mmHg to about 5 mmHg, by about 0.1 mmHg to about 4 mmHg, by about 0.1 mmHg to about 3 mmHg, by about 0.1 mmHg to about 2 mmHg, by about 0.1 mmHg to about 1 mmHg, by about 0.5 mmHg to about 20 mmHg, by about 0.5 mmHg to about 15 mmHg, by about 0.5 mmHg to about 10 mmHg, by about 0.5 mmHg to about 9 mmHg, by about 0.5 mmHg to about 8 mmHg, by about 0.5 mmHg to about 7 mmHg, by about 0.5 mmHg to about 6 mmHg, by about 0.5 mmHg to about 5 mmHg, by about 0.5 mmHg to about 4 mmHg, by about 0.5 mmHg to about 3 mmHg, by about 0.5 mmHg to about 2 mmHg, by about 0.5 mmHg to about 1 mmHg, by about 1 mmHg to about 20 mmHg, by about 1 mmHg to about 15 mmHg, by about 1 mmHg to about 10 mmHg, by about 1 mmHg to about 9 mmHg, by about 1 mmHg to about 8 mmHg, by about 1 mmHg to about 7 mmHg, by about 1 mmHg to about 6 mmHg, by about 1 mmHg to about 5 mmHg, by about 1 mmHg to about 4 mmHg, by about 1 mmHg to about 3 mmHg, or by about 1 mmHg to about 2 mmHg.

Administration of a Tie-2 activator can be topical, such as in an eye drop unit dosage form, based on several findings. In an in vitro study, a formulation of a Tie-2 activator Compound 1 (1.5% of the sodium salt with 5% HPβCD in 50:50 DSW:sterile water) demonstrated substantial diffusion across a rabbit cornea and sclera in Franz cell. In an in vivo study in mice, three topical doses of a Tie-2 activator (Compound 1 at 40 mg/mL in 10% HPβCD) led to accumulation of about 20 micrograms per gram (μg/g) tissue to 30 μg/g tissue in the choroid and retina. In an in vivo study in rabbits, after three topical doses of a Tie-2 activator (Compound 1 at 40 mg/mL in 10% HPβCD) retinal and choroid levels of the Tie-2 activator were about 341 nanograms per gram (ng/g) and 76 ng/g, respectively. In another in vivo study in rabbits, after three topical doses of the Tie-2 activator Compound 1 at 40 mg/mL in 10% HPβCD or 20 mg/mL in 5% dextrose, choroid levels were 8.87 ng/g and 4.31 ng/g, respectively, for the 40 mg/mL and 20 mg/mL formulations at one hour after the last dose. Retina levels were 4.45 ng/g and a. 37 ng/g, respectively, for the 40 mg/mL and 20 mg/mL formulations at one hour after the last dose.

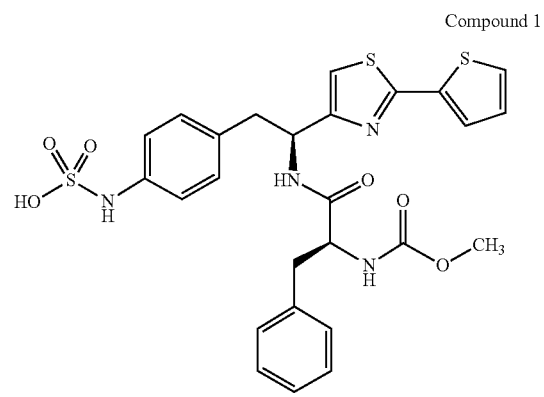 [SMILES: COC(=O)N[C@@H](Cc1ccccc1)C(=O)N[C@@H](Cc1ccc(NS(=O)(=O)O)cc1)c1csc(-c2cccs2)n1]

Compound 1

Treatment of Intraocular Pressure with a Tie-2 Activator

FIG. 1 shows the effect of administration of a Tie-2 activator (Compound 1) delivered twice daily (BID) at varying doses on intraocular pressure (IOP) relative to a pre-treatment baseline. The difference in IOP was determined at the end of the trial, which was 28 days after treatment began (28 Day EOT). Changes in IOP were determined both in the study eye and the fellow eye. Doses greater than 15 mg BID of Compound 1 resulted in decreased IOP in patients with diabetic macular edema.

Figure 2:
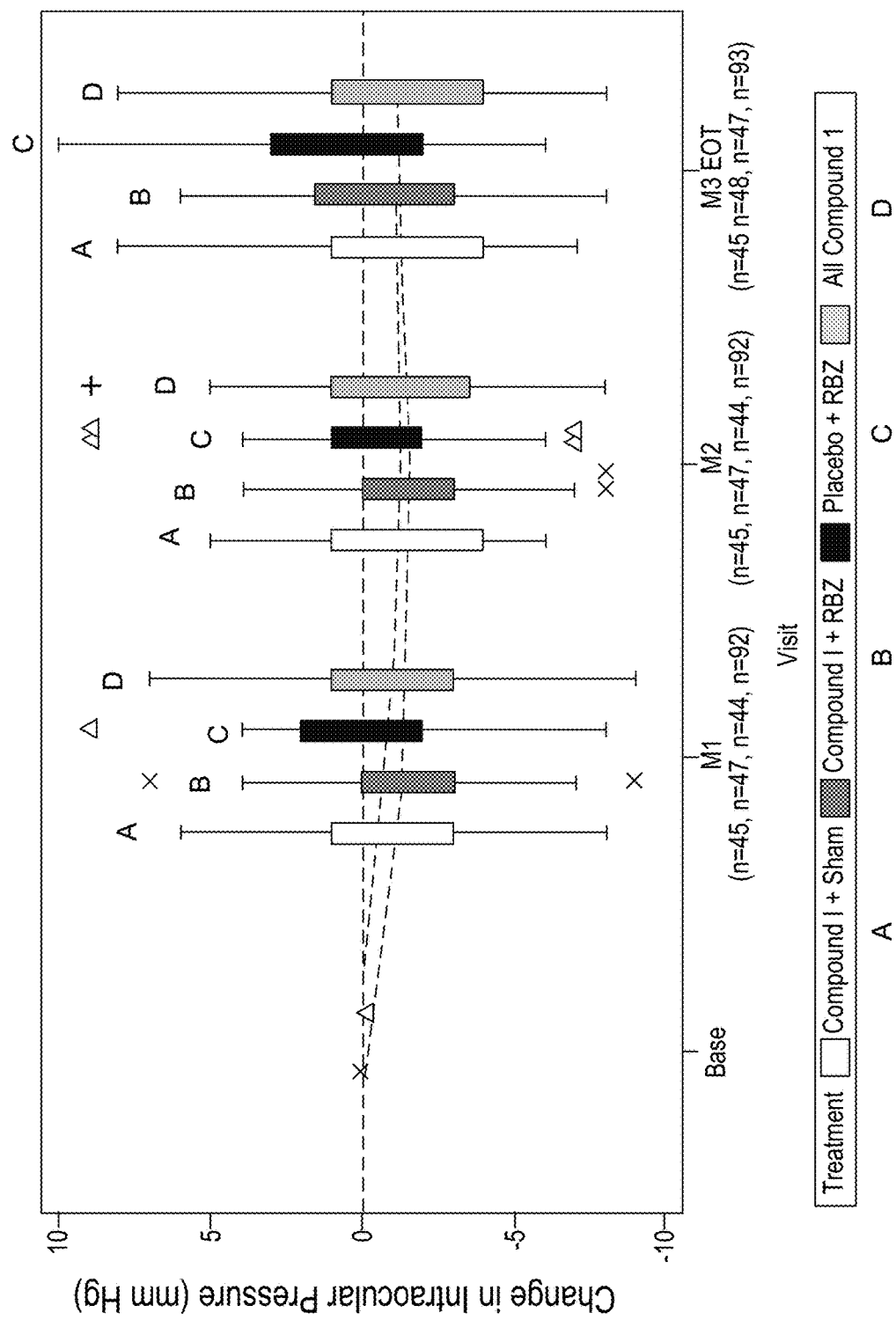
FIG. 2 illustrates changes in intraocular pressure from baseline. A: Compound 1+Sham; B: Compound 1+RBZ; C: Placebo+RBA; D: All Compound 1.

FIG. 2 shows the effect on intraocular pressure of administration of a Tie-2 activator (Compound 1) combined with a sham treatment; Compound 1 combined with ranibizumab (RBZ); a placebo combined with RBZ; or the combined results of both Compound 1 treatment groups. The difference in IOP was determined relative to a pre-treatment baseline (Base) at months 1, 2, and 3 (M1-M3). Intraocular pressure was determined in the study eye in millimeters of mercury (mmHg).

TABLE 1 shows the effect of shows the effect on intraocular pressure of administration of: 1) Compound 1 combined with a sham treatment (Compound 1+sham); 2) Compound 1 combined with ranibizumab (Compound 1+RBZ); or 3) a placebo combined with RBZ (placebo+RBZ). The difference in IOP was determined relative to a pre-treatment Baseline at Months 1, 2, and 3. Intraocular pressure was determined in the study eye/fellow eye in mmHg.

TABLE 1

| IOP | Treatment arm | | |
|---|---|---|---|
| | Compound 1 + sham | Compound 1 + RBZ | placebo + RBZ |
| Baseline | 15.8/15.4 | 15.9/16.1 | 15.2/15.8 |
| Month 1 | 14.8/14.5 | 14.7/14.4 | 15.0/15.5 |
| Month 2 | 14.4/14.3 | 14.6/14.7 | 15.0/15.5 |
| Month 3 | 14.3/14.0 | 15.1/14.7 | 15.3/15.7 |

EXAMPLES

Example 1. Compounds with Inhibitory Activity to HPTP-β

Non-limiting examples of the HPTP-β $IC_{50}$ (μM) activity for illustrative compounds are listed in TABLE 2.

TABLE 2

| No. | Compound | HPTP-β $IC_{50}$ μM |
|---|---|---|
| AA1 | 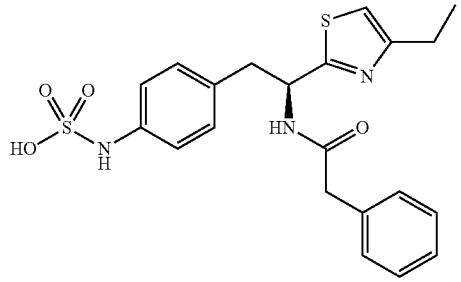<br>(S)-{4-[2-(4-Ethylthiazol-2-yl)-2-(phenylacetylamino)ethyl]-phenyl}sulfamic acid | 0.000157 |
| AA2 | 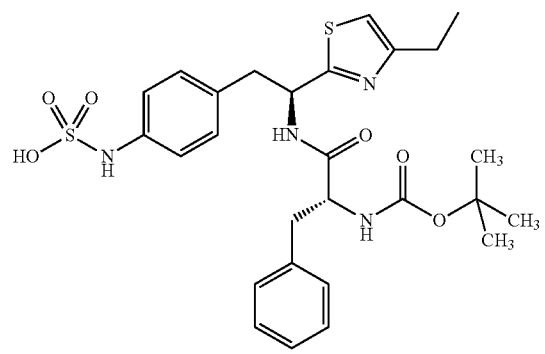<br>4-{(S)-2-[(R)-2-(tert-butoxycarbonylamino)-3-phenylpropanamido]-2-(4-ethylthiazol-2-yl)ethyl}phenylsulfamic acid | 0.004 |

TABLE 2-continued

| No. | Compound | HPTP-β IC$_{50}$ μM |
|---|---|---|
| AA3 | 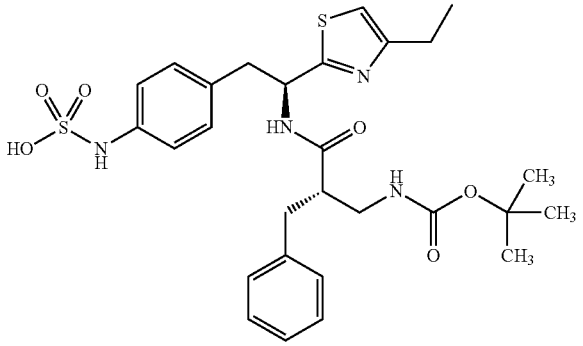 {1-[1-(5-Ethylthiazol-2-yl)-(S)-2-(4-sulfoaminophenyl)ethyl-carbamoyl]-(S)-2-phenylethyl}methyl carbamic acid tert-butyl ester | 0.031 |
| AA4 | 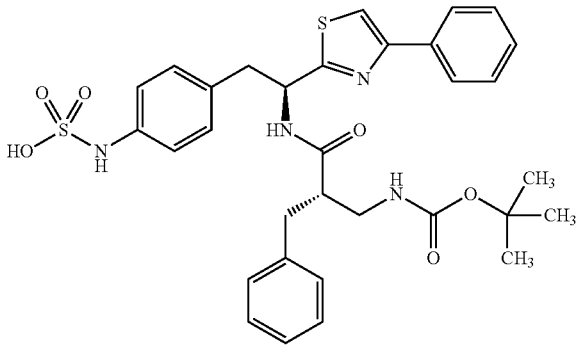 {1-[1-(5-phenylthiazol-2-yl)-(S)-2-(4-sulfoaminophenyl)ethylcarbamoyl]-(S)-2-phenylethyl}methyl carbamic acid tert-butyl ester | <5 × 10$^{-8}$ |
| AA5 | 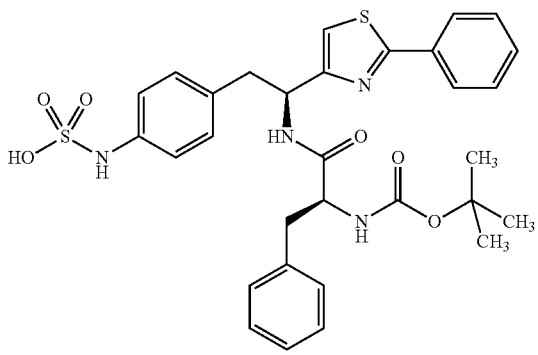 4-{(S)-2-(S)-2-(tert-Butoxycarbonylamino)-3-phenylpropanamido-2-(2-phenylthiazol-4-yl)}phenylsulfamic acid | <5 × 10$^{-8}$ |

TABLE 2-continued
| No. | Compound | HPTP-β IC$_{50}$ μM |
|---|---|---|
| AA6 | 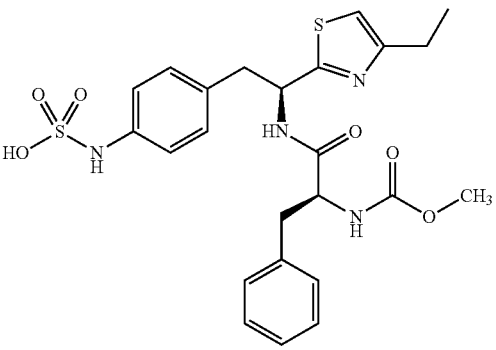<br>4-{(S)-2-(4-Ethylthiazol-2-yl)-2-[(S)-2-(methoxycarbonylamino)-3-phenylpropanamido]ethyl}phenylsulfamic acid | 0.000162 |
| AA7 | 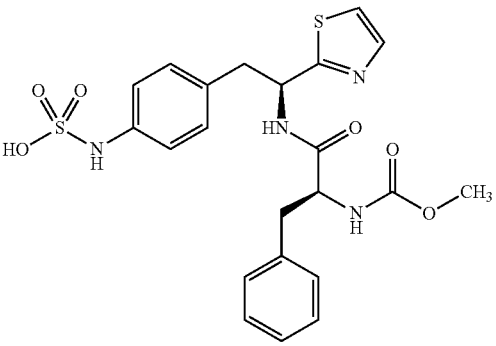<br>4-{(S)-2-[(S)-2-(Methoxycarbonylamino)-3-phenylpropanamido]-2-(thiazol-2-yl)ethyl}phenylsulfamic acid | 0.006 |
| AA8 | 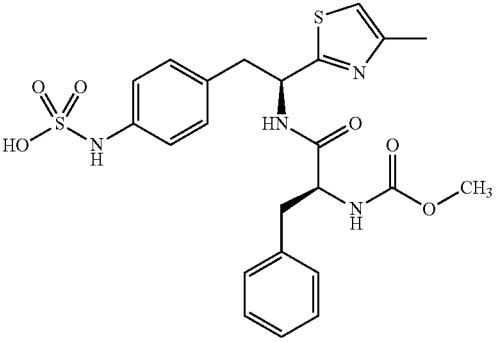<br>4-{(S)-2-[(S)-2-(Methoxycarbonylamino)-3-phenylpropanamido]-2-(4-methylthiazol-2-yl)ethyl}phenylsulfamic acid | 0.001 |

TABLE 2-continued
| No. | Compound | HPTP-β IC$_{50}$ μM |
|---|---|---|
| AA9 | 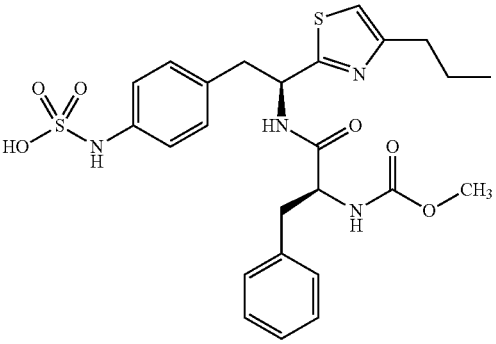<br>4-{(S)-2-[(S)-2-(Methoxycarbonylamino)-3-phenylpropanamido]-2-(4-propylthiazol-2-yl)ethyl}phenylsulfamic acid | 0.0001 |
| AA10 | 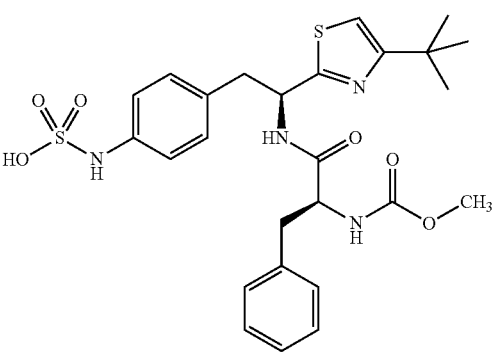<br>4-{(S)-2-(4-tert-Butylthiazol-2-yl)-2-[(S)-2-(methoxycarbonylamino)-3-phenylpropanamido]ethyl}phenylsulfamic acid | 0.0002 |
| AA11 | 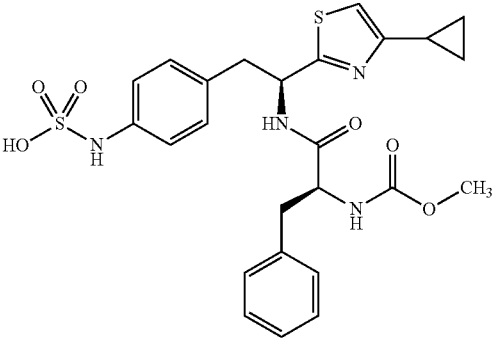<br>4-{(S)-2-(4-Cyclopropylthiazol-2-yl)-2-[(S)-2-(methoxycarbonylamino)-3-phenylpropanamido]ethyl}phenylsulfamic acid | 0.00001 |

TABLE 2-continued
| No. | Compound | HPTP-β IC$_{50}$ μM |
|---|---|---|
| AA12 | 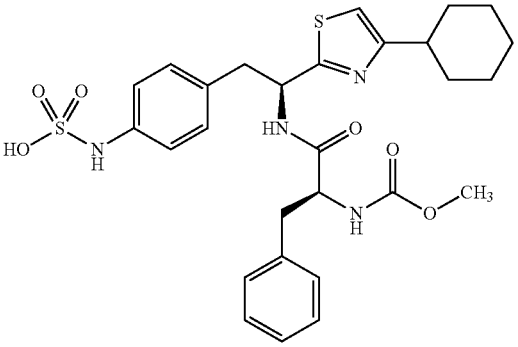<br>4-{(S)-2-(4-Cyclohexylthiazol-2-yl)-2-[(S)-2-(methoxycarbonylamino)-3-phenyl-propanamido]ethyl}phenylsulfamic acid | <5 × 10$^{-8}$ |
| AA13 | 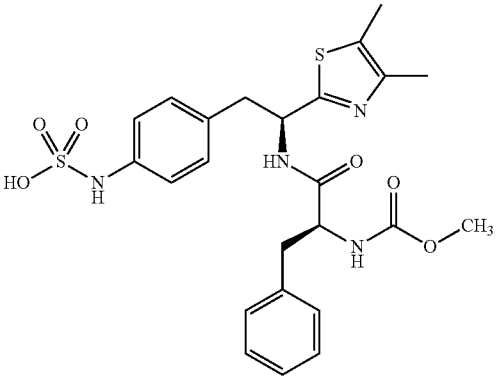<br>4-{(S)-2-(4,5-Dimethylthiazol-2-yl)-2-[(S)-2-(methoxycarbonylamino)-3-phenyl-propanamido]ethyl}phenylsulfamic acid | 0.001 |
| AA14 | 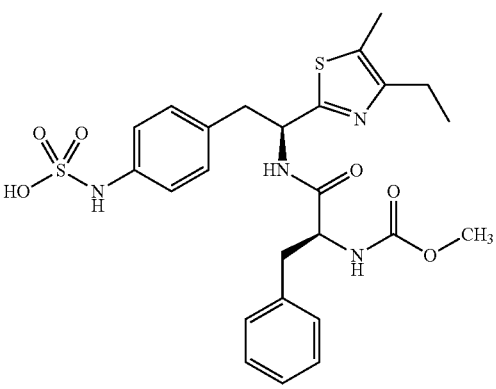<br>4-{(S)-2-(4-Ethyl-5-methylthiazol-2-yl)-2-[(S)-2-(methoxy-carbonylamino)-3-phenyl-propanamido]ethyl}phenylsulfamic acid | 0.0001 |

TABLE 2-continued
| No. | Compound | HPTP-β IC$_{50}$ μM |
|---|---|---|
| AA15 | 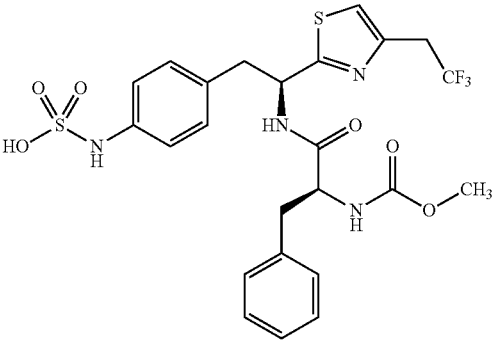 4-{(S)-2-[(S)-2-(Methoxycarbonylamino)-3-phenylpropanamido]-2-[4-(2,2,2-trifluoroethyl)thiazol-2-yl]ethyl}phenylsulfamic acid | 0.0003 |
| AA16 | 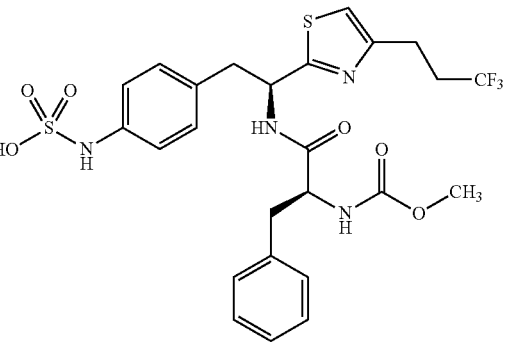 4-{(S)-2-[(S)-2-(Methoxycarbonylamino)-3-phenylpropanamido]-2-[4-(3,3,3-trifluoropropyl)thiazol-2-yl]ethyl}phenylsulfamic acid | 0.00008 |
| AA17 | 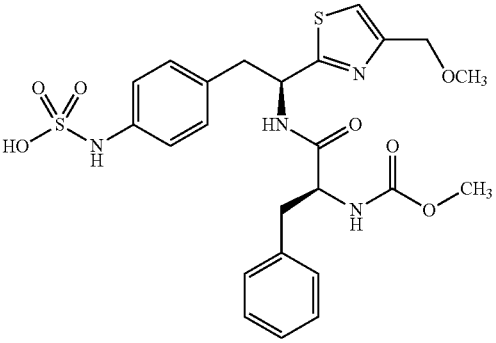 4-{(S)-2-[(S)-2-(Methoxycarbonylamino)-3-phenylpropanamido]-2-[4-(methoxymethyl)thiazol-2-yl]ethyl}phenylsulfamic acid | 0.001 |

TABLE 2-continued
| No. | Compound | HPTP-β IC$_{50}$ μM |
|---|---|---|
| AA18 | 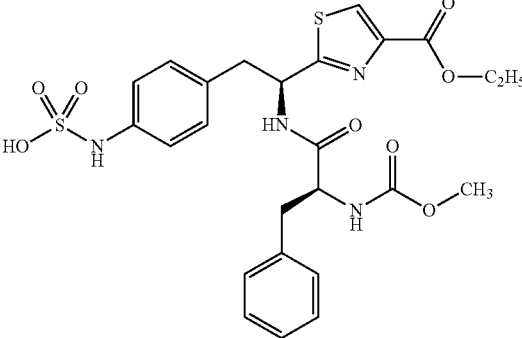<br>4-{(S)-2-(4-(Ethoxycarbonyl)thiazol-2-yl)-2-[(S)-2-(methoxy-carbonylamino)-3-phenylpropanamido]ethyl}phenylsulfamic acid | 0.0002 |
| AA19 | 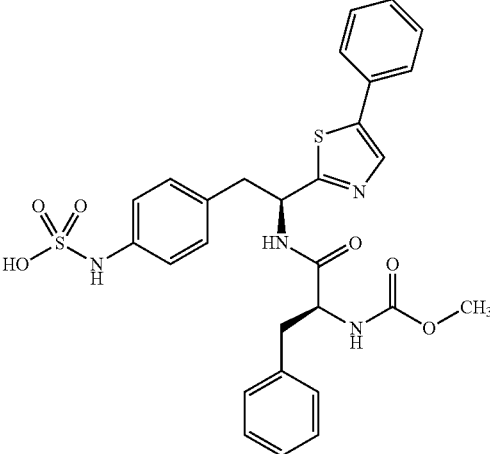<br>4-{(S)-2-[(S)-2-(Methoxycarbonylamino)-3-phenylpropanamido]-2-[5-phenylthiazol-2-yl)ethyl}phenylsulfamic acid | 0.0003 |
| AA20 | 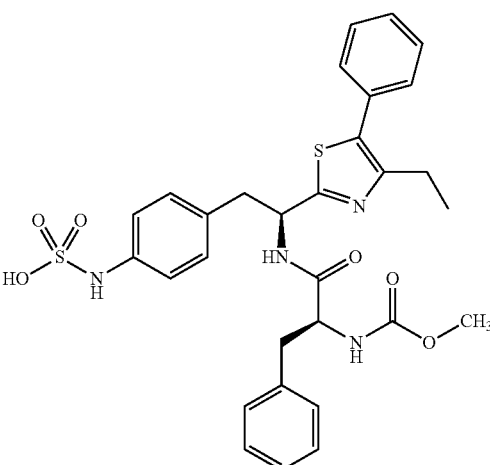<br>4-{(S)-2-(4-Ethyl-5-phenylthiazol-2-yl)-2-[(S)-2-(methoxy-carbonylamino)-3-phenyl-propanamido]ethyl}phenylsulfamic acid | <5 × 10$^{-8}$ |

TABLE 2-continued

| No. | Compound | HPTP-β IC$_{50}$ μM |
|---|---|---|
| AA21 | 4-{(S)-2-[(S)-2-(Methoxycarbonylamino)-3-phenylpropanamido]-2-(4-phenylthiazol-2-yl)ethyl}phenylsulfamic acid | <2 × 10$^{-6}$ |
| AA22 | 4-{(S)-2-[(S)-2-(Methoxycarbonylamino)-3-phenylpropanamido]-2-(4-(thiophen-2-yl)thiazol-2-yl)ethyl}phenylsulfamic acid | <5 × 10$^{-8}$ |
| AA23 | 4-{(S)-2-[(S)-2-(Methoxycarbonylamino)-3-phenylpropanamido]-2-[4-(thiophen-3-yl)thiazol-2-yl]ethyl}phenylsulfamic acid | 0.00009 |

TABLE 2-continued

| No. | Compound | HPTP-β IC$_{50}$ μM |
|---|---|---|
| AA24 | 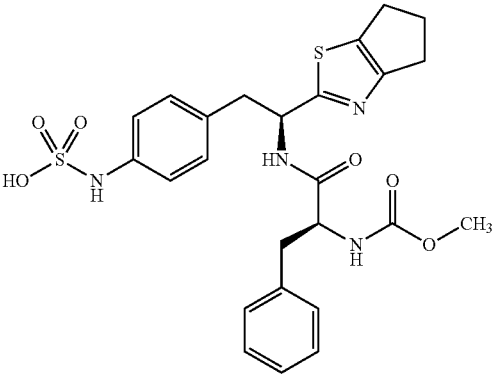  4-{(S)-2-(5,6-Dihydro-4H-cyclopenta[d]thiazol-2-yl)-2-[(S)-2-(methoxycarbonylamino)-3-phenylpropanamido]ethyl}phenylsulfamic acid | 0.001 |
| AA25 | 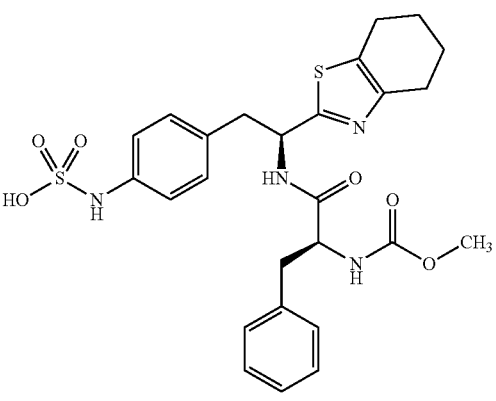  4-{(S)-2-[(S)-2-(Methoxycarbonylamino)-3-phenylpropanamido]-2-(4,5,6,7-tetrahydrobenzo[d]thiazol-2-yl)ethyl}phenylsulfamic acid | 0.0004 |
| AA26 | 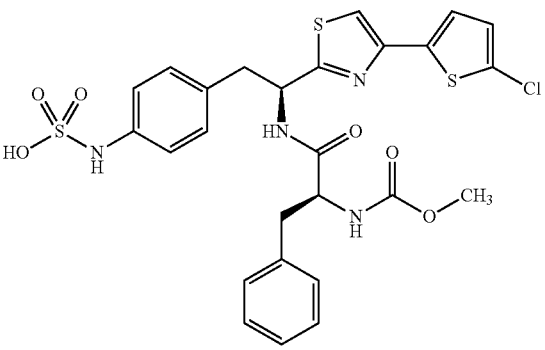  4-{(S)-2-[4-(5-Chlorothiophen-2-yl)thiazol-2-yl]-2-[(S)-2-(methoxycarbonylamino)-3-phenylpropanamido]ethyl}phenyl-sulfamic acid | <5 × 10$^{-8}$ |

TABLE 2-continued
| No. | Compound | HPTP-β IC$_{50}$ μM |
|---|---|---|
| AA27 | 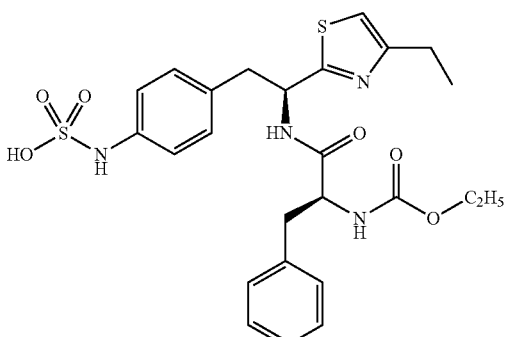 4-{(S)-2-[(S)-2-(Ethoxycarbonylamino)-3-phenylpropanamido]-2-(4-ethylthiazol-2-yl)ethyl}phenylsulfamic acid | 0.00014 |
| AA28 | 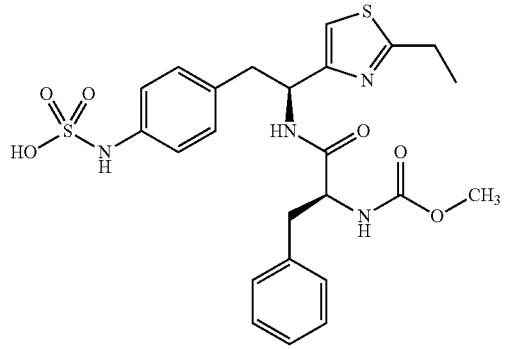 4-{(S)-2-[(S)-2-(Methoxycarbonylamino)-3-phenylpropanamido]-2-(2-ethylthiazol-4-yl)ethyl}phenylsulfamic acid | 0.0001 |
| AA29 | 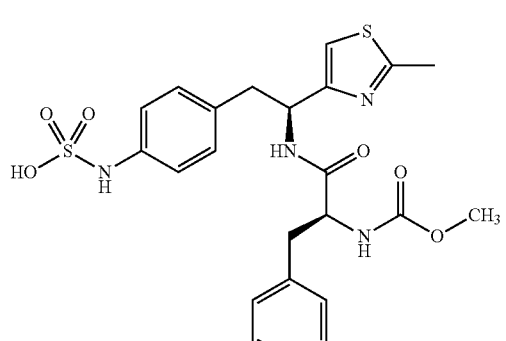 4-{(S)-2-[(S)-2-(Methoxycarbonylamino)-3-phenylpropanamido]-2-(2-methylthiazol-4-yl)ethyl}phenylsulfamic acid | 0.001 |

TABLE 2-continued

| No. | Compound | HPTP-β IC$_{50}$ μM |
|---|---|---|
| AA30 | 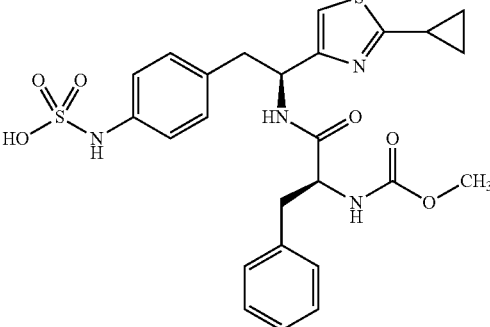<br>4-{(S)-2-(2-Cyclopropylthiazol-4-yl)-2-[(S)-2-(methoxy-carbonylamino)-3-phenylpropanamido]ethyl}phenylsulfamic acid | 0.0002 |
| AA31 | 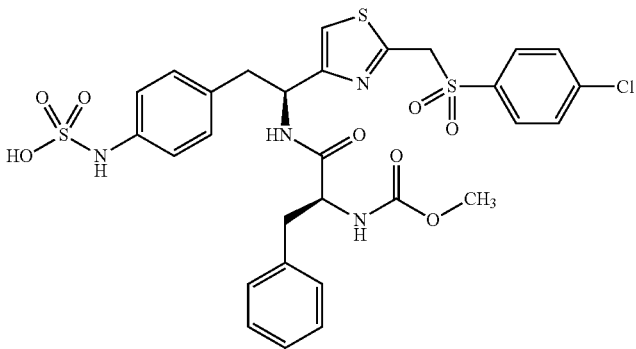<br>4-{(S)-2-{2-[(4-Chlorophenylsulfonyl)methyl]thiazol-4-yl}-2-[(S)-2-(methoxycarbonylamino)-3-phenylpropanamido]ethyl}phenylsulfamic acid | 0.00008 |
| AA32 | 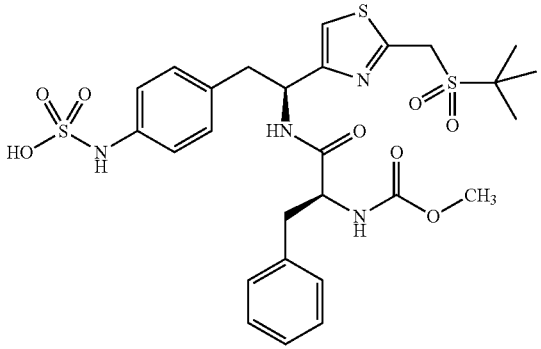<br>4-{(S)-2-[2-(tert-Butylsulfonylmethyl)thiazol-4-yl]-2-[(S)-2-(methoxycarbonylamino)-3-phenylpropanamido]ethyl}phenylsulfamic acid | 0.002 |

TABLE 2-continued

| No. | Compound | HPTP-β IC$_{50}$ μM |
|---|---|---|
| AA33 | 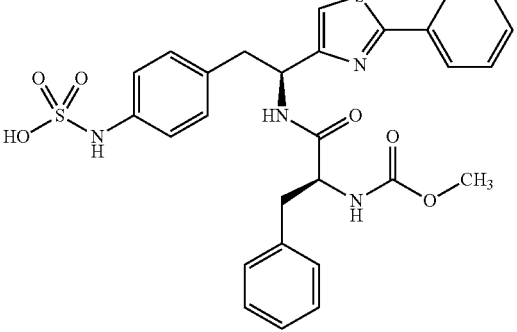<br>4-{(S)-2-[(S)-2-(Methoxycarbonylamino)-3-phenylpropionamido]-2-(2-phenylthiazole-4-yl)ethyl}phenylsulfamic acid | $7 \times 10^{-7}$ |
| AA34 | 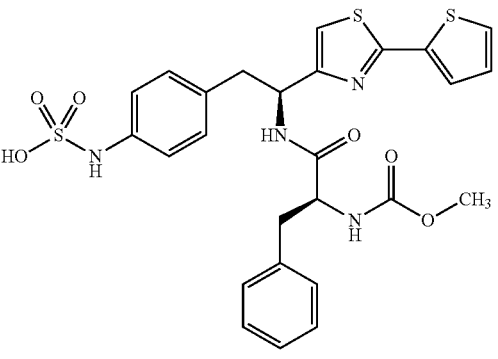<br>4-{(S)-2-[(S)-2-(Methoxycarbonylamino)-3-phenylpropanamido]-2-[2-(thiophen-2-yl)thiazol-4-yl]ethyl}phenylsulfamic acid | $5 \times 10^{-8}$ |
| AA35 | 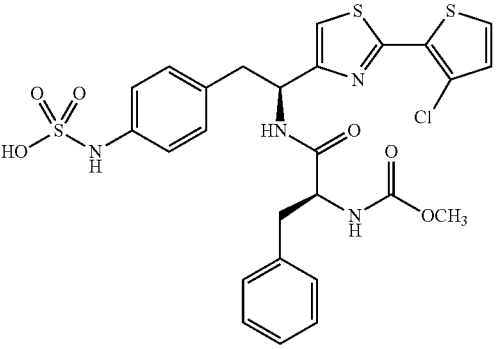<br>4-{(S)-2-[2-(3-Chlorothiophen-2-yl)thiazol-4-yl]-2-[(S)-2-(methoxycarbonylamino)-3-phenylpropanamido]ethyl}phenylsulfamic acid | $<5 \times 10^{-8}$ |

TABLE 2-continued

| No. | Compound | HPTP-β IC$_{50}$ μM |
|---|---|---|
| AA36 | 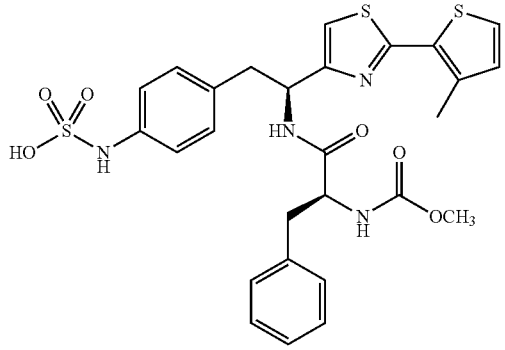<br>4-{(S)-2-[(S)-2-(Methoxycarbonylamino)-3-phenylpropanamido]-2-[2-(3-methylthiophen-2-yl)thiazol-4-yl]ethyl}phenylsulfamic acid | <5 × 10$^{-8}$ |
| AA37 | 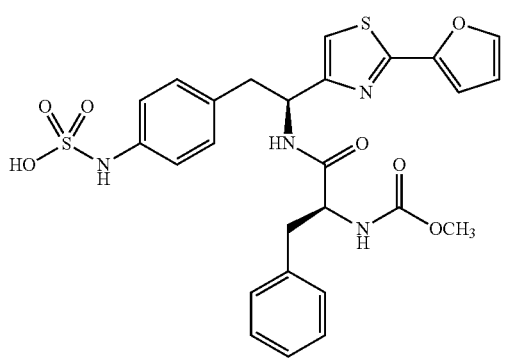<br>4-{[(S)-2-(2-(Furan-2-yl)thiazol-4)yl]-2-[(S)-2-(methoxycarbonylamino)-3-phenylpropanamido]ethyl}phenylsulfamic acid | 0.0004 |
| AA38 | 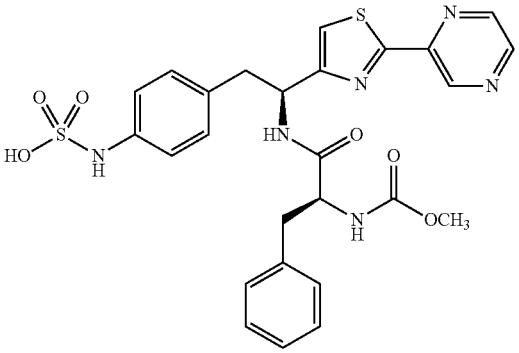<br>4-{(S)-2-[(S)-2-(Methoxycarbonylamino)-3-phenylpropanamido]-2-[2-(pyrazin-2-yl)thiazol-4-yl]ethyl}phenylsulfamic acid | 0.003 |

TABLE 2-continued
| No. | Compound | HPTP-β IC$_{50}$ μM |
|---|---|---|
| AA39 | 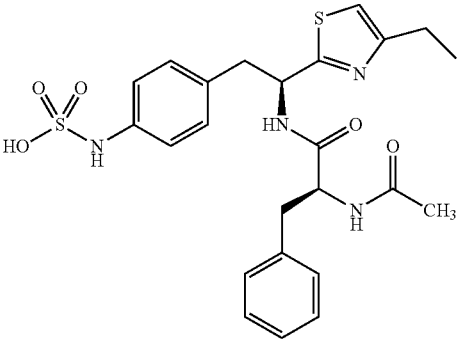 4-[(S)-2-((S)-2-Acetamido-3-phenylpropanamido)-2-(4-ethylthiazol-2-yl)ethyl]phenylsulfamic acid | 0.001 |
| AA40 | 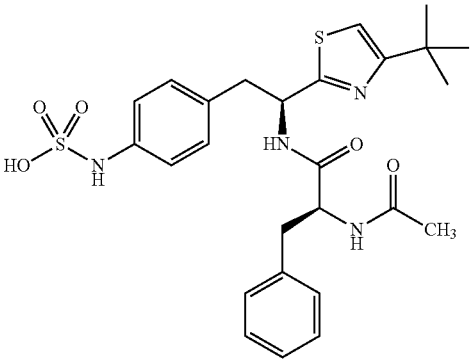 4-[(S)-2-((S)-2-Acetamido-3-phenylpropanamido)-2-(4-tert-butylthiazol-2-yl)ethyl]phenylsulfamic acid | 0.0003 |
| AA41 | 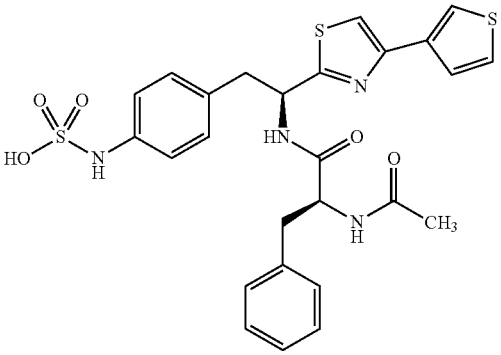 4-{(S)-2-((S)-2-Acetamido-3-phenylpropanamido)-2-[4-(thiophen-3-yl)thiazol-2-yl]ethyl}phenylsulfamic acid | 0.00024 |

TABLE 2-continued

| No. | Compound | HPTP-β IC$_{50}$ μM |
|---|---|---|
| AA42 | 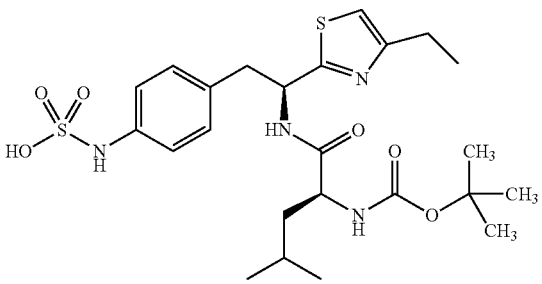<br>4-{(S)-2-[(S)-2-(tert-Butoxycarbonylamino)-3-methylbutanamido]-2-(4-ethylthiazol-2-yl)ethyl}phenylsulfamic acid | 0.006 |
| AA43 | 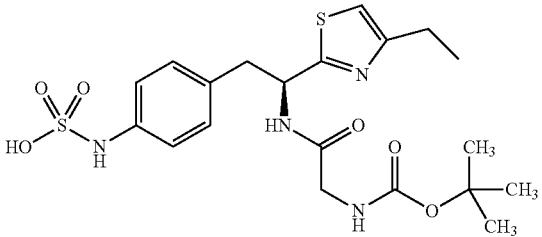<br>(S)-4-{2-[2-(tert-Butoxycarbonylamino)acetamido]-2-(4-ethylthiazol-2-yl)ethyl}phenylsulfamic acid | 0.028 |
| AA44 | 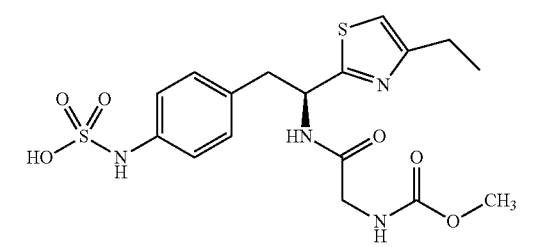<br>(S)-4-{2-(4-Ethylthiazol-2-yl)-2-[2-(methoxycarbonylamino)acetamido]ethyl}phenylsulfamic acid | 0.020 |
| AA45 | 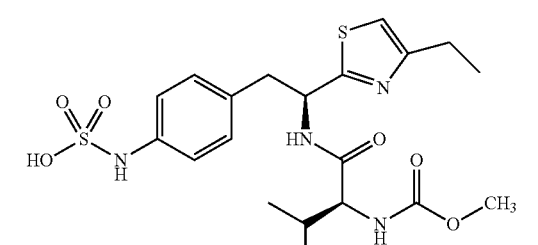<br>4-{(S)-2-(4-Ethylthiazol-2-yl)-2-[(S)-2-(methoxycarbonylamino)-3-methylbutanamido]-ethyl}phenylsulfamic acid | 0.003 |

TABLE 2-continued

| No. | Compound | HPTP-β IC$_{50}$ μM |
|---|---|---|
| AA46 | 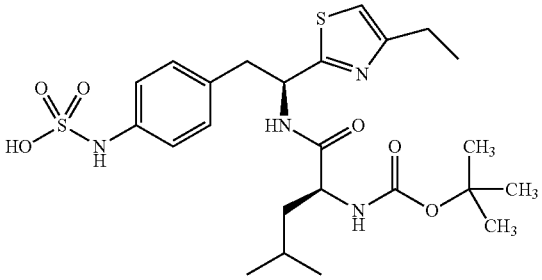<br>4-{(S)-2-[(S)-2-(tert-Butoxycarbonylamino)-4-methylpentanamido]-2-(4-ethylthiazol-2-yl)ethyl}phenylsulfamic acid | 0.001 |
| AA47 | 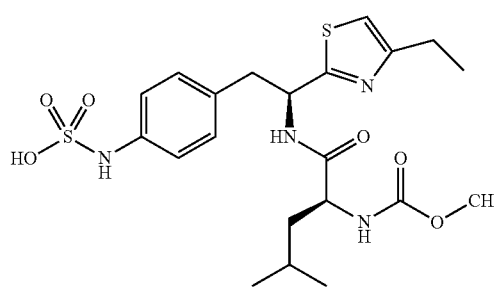<br>4-{(S)-2-(4-Ethylthiazol-2-yl)-2-[(S)-2-(methoxycarbonylamino)-4-methylpentanamido]ethyl}phenylsulfamic acid | 0.0003 |
| AA48 | 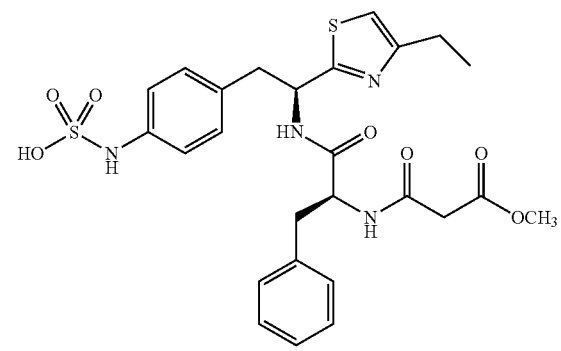<br>4-((S)-2-(4-Ethylthiazol-2-yl)-2-{(S)-2-[2-(methoxycarbonylamino)-acetamido]-3-phenylpropanamido}ethyl)phenylsulfamic acid | 0.0003 |
| AA49 | 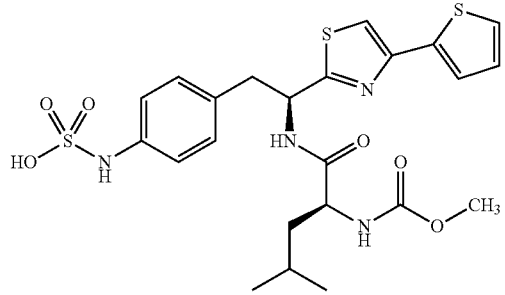<br>4-{(S)-2-[(S)-2-(Methoxycarbonylamino)-4-methylpentanamido]-2-[2-(thiophen-2-yl)thiazol-4-yl]ethyl}phenylsulfamic acid | <5 × 10$^{-8}$ |

TABLE 2-continued
| No. | Compound | HPTP-β IC$_{50}$ μM |
|---|---|---|
| AA50 | 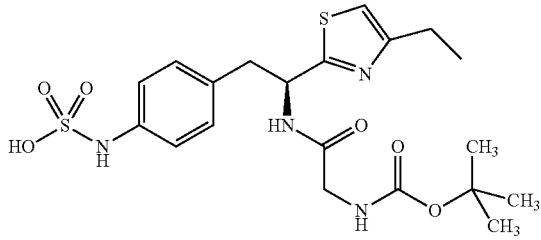<br>(S)-4-{2-[2-(tert-Butoxycarbonylamino)acetamido]-2-(4-ethylthiazol-2-yl)ethyl}-phenylsulfamic acid | 0.028 |
| AA51 | 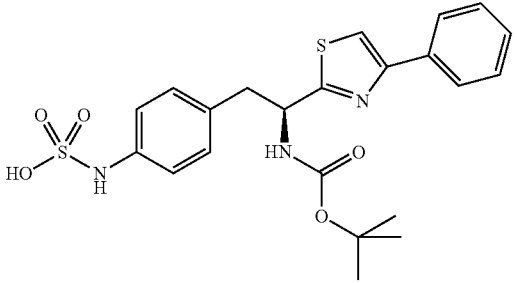<br>[1-(S)-(Phenylthiazol-2-yl)-2-(4-sulfoaminophenyl)ethyl]-carbamic acid tert-butyl ester | 0.049 |
| AA52 | 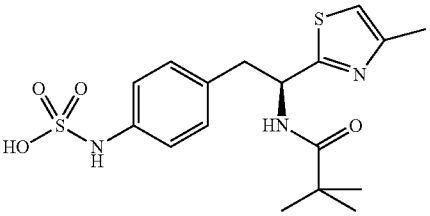<br>(S)-4-(2-(4-Methylthiazol-2-yl)-2-pivalamidoethyl)phenyl-sulfamic acid | 0.112 |
| AA53 | 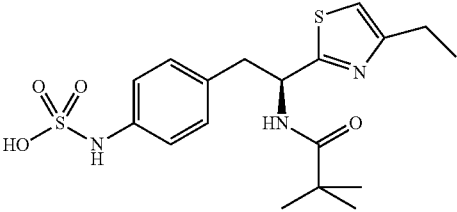<br>(S)-4-(2-(4-Ethylthiazol-2-yl)-2-pivalamidoethyl)phenyl-sulfamic acid | 0.085 |

TABLE 2-continued

| No. | Compound | HPTP-β IC$_{50}$ μM |
|---|---|---|
| AA54 | 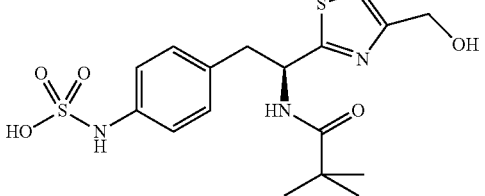<br>(S)-4-{2-[4-(hydroxymethyl)thiazol-2-yl]-2-pivalamidoethyl}phenyl-sulfamic acid | 0.266 |
| AA55 | 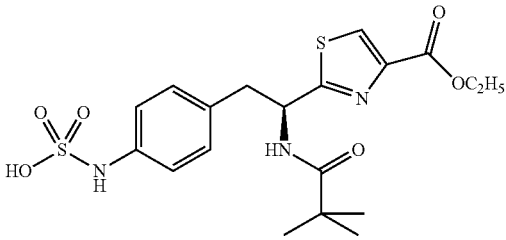<br>(S)-4-{[2-(4-Ethoxycarbonyl)thiazol-2-yl]-2-pivalamidoethyl}phenylsulfamic acid | 0.584 |
| AA56 | 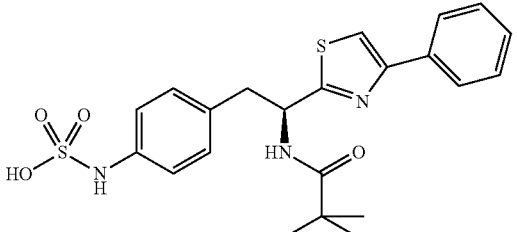<br>(S)-4-(2-(4-Phenylthiazol-2-yl)-2-pivalamidoethyl)phenylsulfamic acid | 0.042 |
| AA57 | 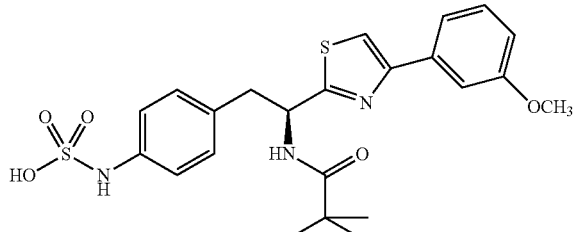<br>4-((S)-2-(4-(3-Methoxyphenyl)thiazol-2-yl)-2-pivalamidoethyl)phenylsulfamic acid | 0.110 |
| AA58 | 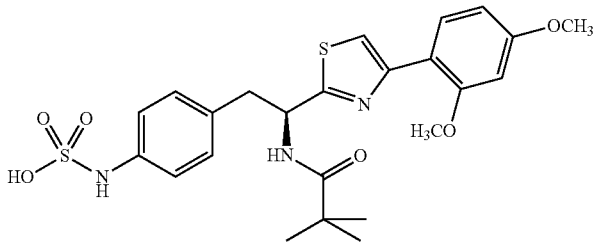<br>4-((S)-2-(4-(2,4-Dimethoxyphenyl)thiazol-2-yl)-2-pivalamidoethyl)phenyl-sulfamic acid | 0.086 |

TABLE 2-continued
| No. | Compound | HPTP-β IC$_{50}$ μM |
|---|---|---|
| AA59 | 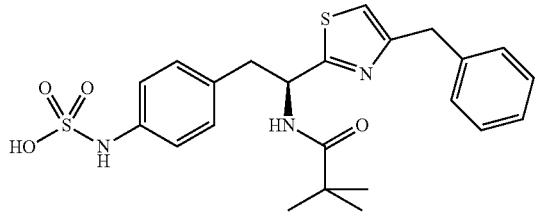<br>(S)-4-(2-(4-Benzylthiazol-2-yl)-2-pivalamidoethyl)phenylsulfamic acid | 0.113 |
| AA60 | 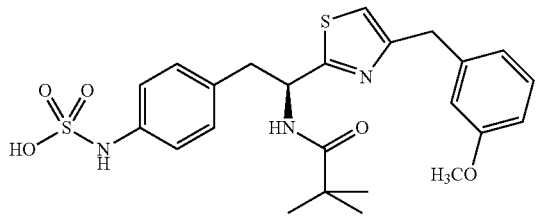<br>(S)-4-(2-(4-(3-Methoxybenzyl)thiazol-2-yl)-2-pivalamidoethyl)phenylsulfamic acid | 0.132 |
| AA61 | 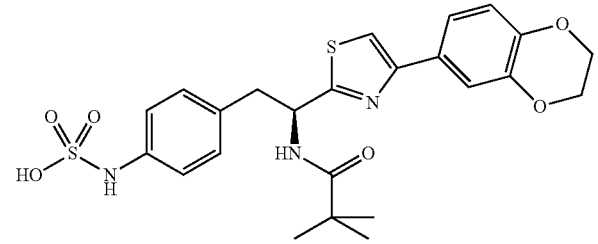<br>4-((S)-2-(4-(2,3-Dihydrobenzo[b][1,4]dioxin-6-yl)thiazol-2-yl)-2-pivalamidoethyl)phenylsulfamic acid | 0.138 |
| AA62 | 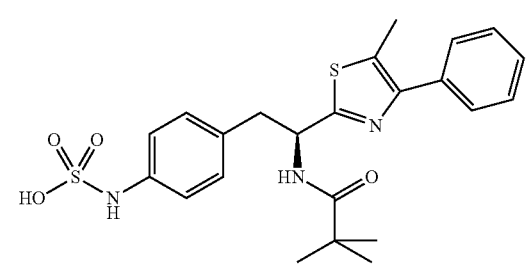<br>(S)-4-(2-(5-Methyl-4-phenylthiazol-2-yl)-2-pivalamidoethyl)phenylsulfamic acid | 0.098 |

TABLE 2-continued
| No. | Compound | HPTP-β IC$_{50}$ μM |
|---|---|---|
| AA63 | 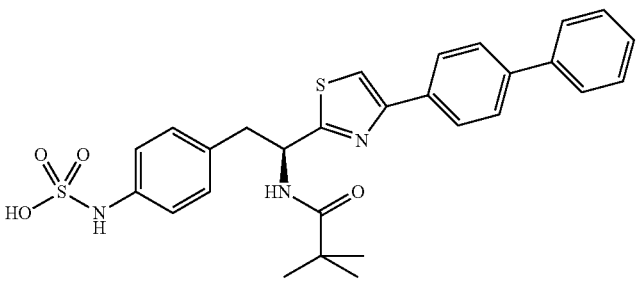(S)-4-(2-(4-(Biphen-4-yl)thiazol-2-yl)-2-pivalamidoethyl)phenylsulfamic acid | 0.381 |
| AA64 | 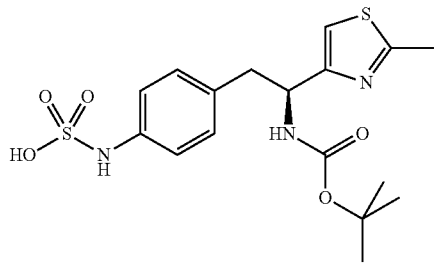(S)-4-(2-tert-Butoxycarbonylamino)-2-(2-methylthiazol-4-yl)ethyl)phenylsulfamic acid | 0.033 |
| AA65 | 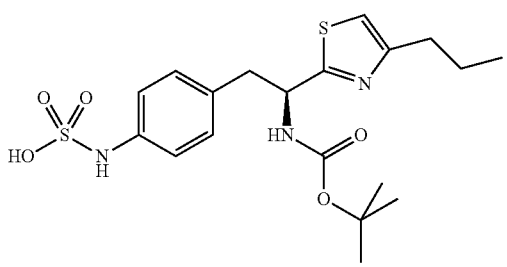(S)-4-(2-(tert-Butoxycarbonylamino)-2-(4-propylthiazol-2-yl)ethyl)phenyl sulfamic acid | 0.04 |
| AA66 | 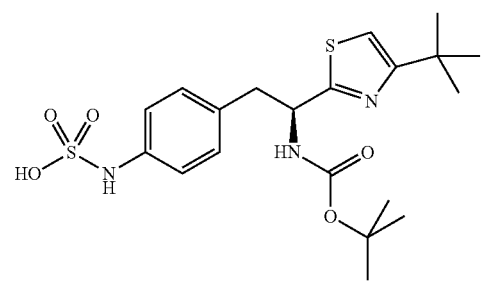(S)-4-(2-(tert-Butoxycarbonylamino)-2-(4-tert-butylthiazol-2-yl)ethyl)phenyl sulfamic acid | 0.027 |

TABLE 2-continued

| No. | Compound | HPTP-β IC$_{50}$ μM |
|---|---|---|
| AA67 | 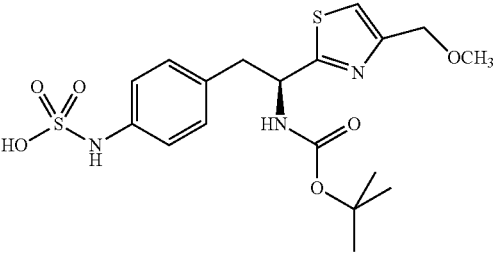<br>(S)-4-(2-(tert-Butoxycarbonylamino)-2-(4-(methoxymethyl)thiazol-2-yl)ethyl)-phenyl sulfamic acid | 0.18 |
| AA68 | 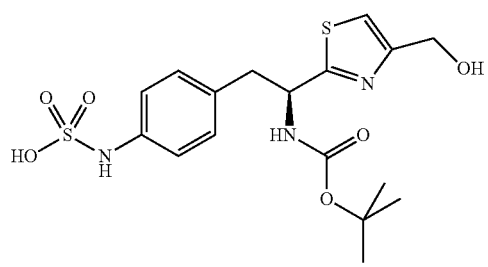<br>(S)-4-(2-(tert-Butoxycarbonylamino)-2-(4-(hydroxymethyl)thiazol-2-yl)ethyl)phenylsulfamic acid | 0.644 |
| AA69 | 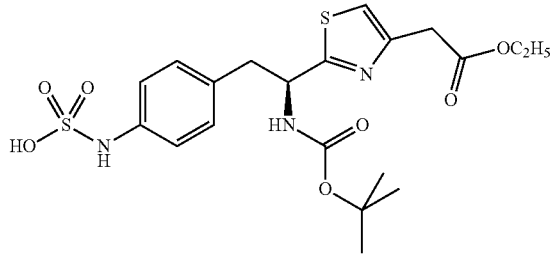<br>(S)-4-(2-(tert-Butoxycarbonylamino)-2-(4-(2-ethoxy-2-oxoethyl)thiazol-2-yl)ethyl)phenylsulfamic acid | 0.167 |
| AA70 | 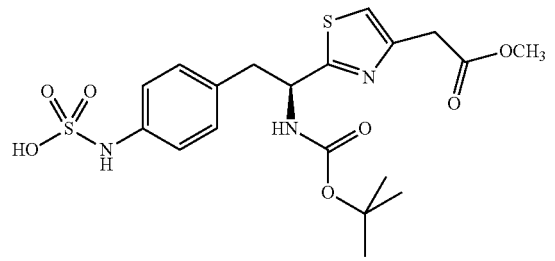<br>(S)-4-(2-(tert-Butoxycarbonyl)-2-(4-(2-(2-methoxy-2-oxoyethyl amino)-2-oxoethyl)thiazole-2-yl)ethyl)phenylsulfamic acid | 0.132 |

TABLE 2-continued

| No. | Compound | HPTP-β IC$_{50}$ μM |
|---|---|---|
| AA71 | 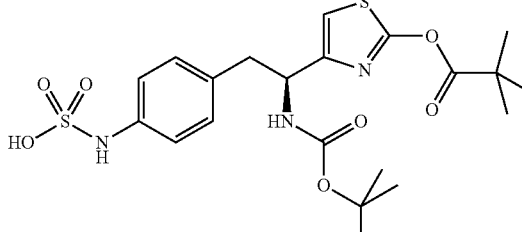<br>(S)-4-(2-(tert-Butoxycarbonylamino)-2-(2-pivalamidothiazol-4-yl)ethyl)phenylsulfamic acid | 0.555 |
| AA72 | 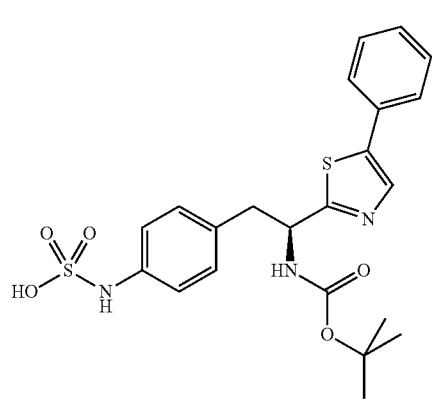<br>(S)-4-(2-(tert-Butoxycarbonylamino)-2-(5-phenylthiazol-2-yl)ethyl)-phenyl sulfamic acid | 0.308 |
| AA73 | 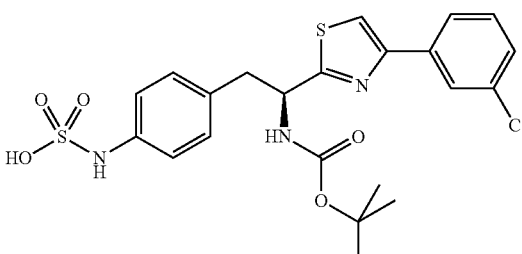<br>4-((S)-2-(tert-Butoxycarbonylamino)-2-(4-(3-(trifluoromethyl)phenyl)thiazol-2-yl)ethyl)-phenyl sulfamic acid | 0.253 |
| AA74 | 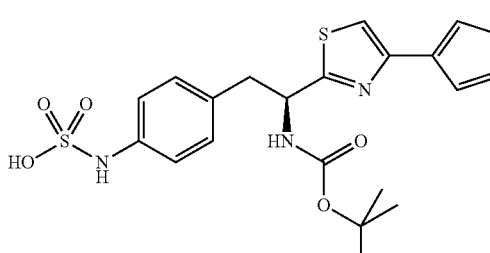<br>4-((S)-2-(tert-Butoxycarbonylamino)-2-(4-(thiophen-3-yl)thiazol-2-yl)phenyl)phenyl sulfamic acid | 0.045 |

TABLE 2-continued

| No. | Compound | HPTP-β IC$_{50}$ μM |
|---|---|---|
| AA75 | (S)-{4-[2-(4-Ethylthiazol-2-yl)-2-(phenylacetylamido)ethyl]-phenyl}sulfamic acid | 0.05 |
| AA76 | (S)-4-(2-(4-Ethylthiazol-2-yl)-2-(2-(2-fluorophenyl)acetamido)ethyl)phenyl-sulfamic acid | 0.012 |
| AA77 | (S)-4-(2-(4-Ethylthiazol-2-yl)-2-(2-(3-fluorophenyl)acetamido)ethyl)phenyl-sulfamic acid | 0.0003 |
| AA78 | (S)-4-(2-(2-(2,3-Difluorophenyl)acetamido)-2-(4-ethylthiazol-2-yl)ethyl)phenyl-sulfamic acid | 0.028 |

TABLE 2-continued
| No. | Compound | HPTP-β IC$_{50}$ μM |
|---|---|---|
| AA79 | 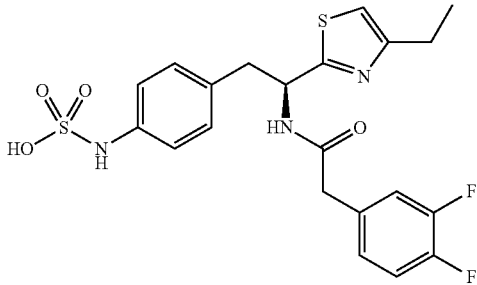<br>(S)-4-(2-(2-(3,4-Difluorophenyl)acetamido)-2-(4-ethylthiazol-2-yl)ethyl)phenyl-sulfamic acid | 0.075 |
| AA80 | 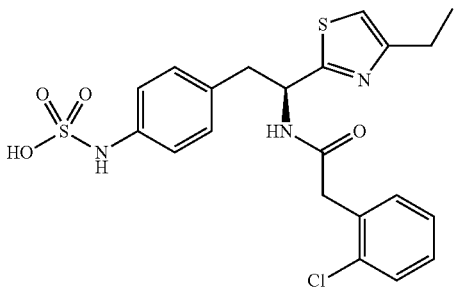<br>(S)-4-(2-(2-(2-Chlorophenyl)acetamido)-2-(4-ethylthiazol-2-yl)ethyl)phenyl-sulfamic acid | 0.056 |
| AA81 | 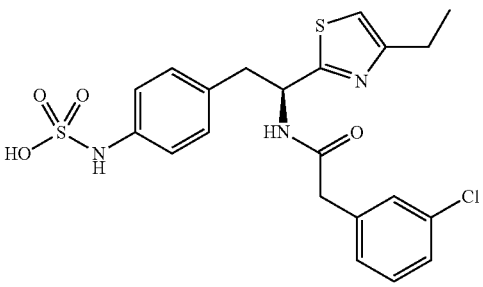<br>(S)-4-(2-(2-(3-Chlorophenyl)acetamido)-2-(4-ethylthiazol-2-yl)ethyl)phenyl-sulfamic acid | 0.033 |
| AA82 | 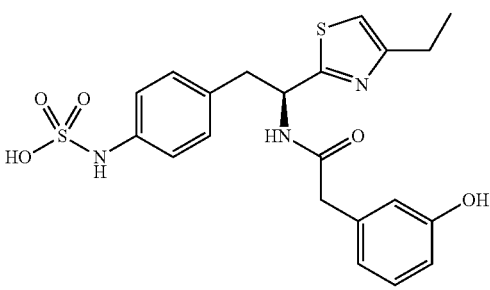<br>(S)-4-(2-(4-Ethylthiazol-2-yl)-2-(2-(3-hydroxyphenyl)acetamido)ethyl)phenyl-sulfamic acid | 0.04 |

TABLE 2-continued
| No. | Compound | HPTP-β IC$_{50}$ μM |
|---|---|---|
| AA83 | 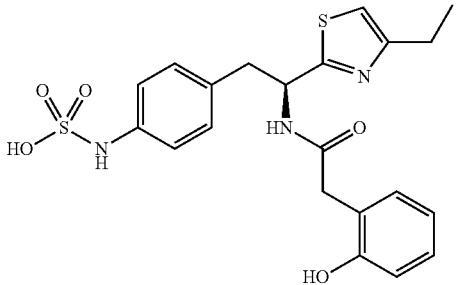<br>(S)-4-(2-(4-Ethylthiazol-2-yl)-2-(2-(2-methoxyphenyl)acetamido)ethyl)phenyl-sulfamic acid | 0.014 |
| AA84 | 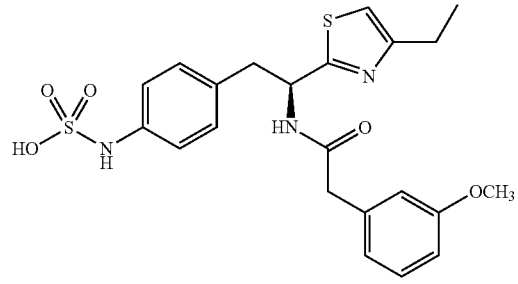<br>(S)-4-(2-(4-Ethylthiazol-2-yl)-2-(2-(3-methoxyphenyl)acetamido)ethyl)phenyl-sulfamic acid | 0.008 |
| AA85 | 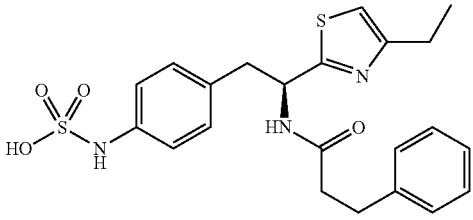<br>(S)-4-(2-(4-Ethylthiazol-2-yl)-2-(3-phenylpropanamido)ethyl)phenylsulfamic acid | 0.002 |
| AA86 | 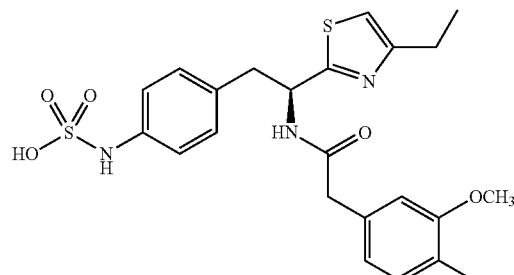<br>(S)-4-(2-(2-(3,4-Dimethoxyphenyl)acetamido)-2-(4-ethylthiazol-2-yl)ethyl)-phenylsulfamic acid | 0.028 |

TABLE 2-continued

| No. | Compound | HPTP-β IC$_{50}$ μM |
|---|---|---|
| AA87 | (S)-4-(2-(2-(2,3-Dimethoxyphenyl)acetamido)-2-(4-ethylthiazol-2-yl)ethyl)-phenylsulfamic acid | 0.037 |
| AA88 | (S)-4-(2-(3-(3-Chlorophenyl)propanamido)-2-(4-ethylthiazol-2-yl)ethyl)phenyl-sulfamic acid | 0.0002 |
| AA89 | (S)-4-(2-(4-Ethylthiazol-2-1)-2-(3-(2-methoxyphenyl)propanamido)ethyl)phenyl-sulfamic acid | 0.003 |
| AA90 | (S)-4-(2-(4-Ethylthiazol-2-yl)-2-(3-(3-methoxyphenyl)propanamido)ethyl)phenyl-sulfamic acid | 0.01 |

TABLE 2-continued

| No. | Compound | HPTP-β IC$_{50}$ μM |
|---|---|---|
| AA91 | (S)-4-(2-(4-Ethylthiazol-2-yl)-2-(3-(4-methoxyphenyl)propanamido)ethyl)phenyl-sulfamic acid | 0.006 |
| AA92 | (S)-4-{2-[2-(4-Ethyl-2,3-dioxopiperazin-1-yl)acetamide]-2-(4-ethylthiazol-2-yl)ethyl}phenylsulfamic acid | 0.002 |
| AA93 | (S)-4-{2-(4-Ethylthiazol-2-yl)-2-[2-(5-methyl-2,4-dioxo-3,4-dihydropyrimidin-1(2H)-yl)acetamide]ethyl}phenylsulfamic acid | 0.002 |
| AA94 | (S)-4-[2-(Benzo[d][1,3]dioxole-5-carboxamido)-2-(4-ethylthiazol-2-yl)ethyl]phenylsulfamic acid | 0.042 |

TABLE 2-continued

| No. | Compound | HPTP-β IC$_{50}$ μM |
|---|---|---|
| AA95 | (S)-4-(2-(5-methyl-1,3,4-thiadiazol-2-ylamino)-2-(2-phenylthiazol-4-yl)ethyl)phenylsulfamic acid | 0.003 |
| AA96 | (S)-4-(2-(5-Phenyl-1,3,4-thiadiazol-2-ylamino)-2-(2-phenylthiazol-4-yl)ethyl)-phenylsulfamic acid | 0.046 |
| AA97 | 4-((S)-2-(5-Propyl-1,3,4-thiadiazol-2-ylamino)-2-(2-(thiophen-2-yl)thiazol-4-yl)ethyl)phenylsulfamic acid | 0.0002 |
| AA98 | 4-((S)-2-(5-Benzyl-1,3,4-thiadiazol-2-ylamino)-2-(2-(thiophen-2-yl)thiazol-4-yl)ethyl)phenylsulfamic acid | 0.0006 |

TABLE 2-continued

| No. | Compound | HPTP-β IC$_{50}$ μM |
|---|---|---|
| AA99 | 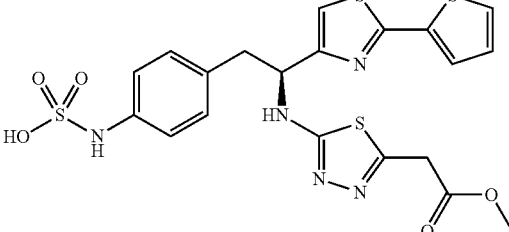<br>4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid | 0.002 |
| AA100 | 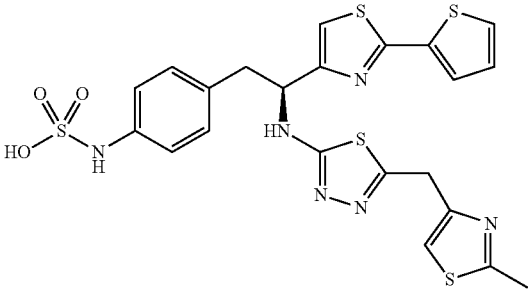<br>4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid | $9 \times 10^{-6}$ |

Example 2. Ocular Pharmacokinetics after Administration of Compound 1

To measure the concentration of Compound 1 in plasma and ocular tissues following topical ocular, subcutaneous, and intravitreal administration, New Zealand White rabbits were administered Compound 1, and plasma and ocular samples were collected at pre-determined time points. Compound 1 formulations were prepared fresh on each day of dosing.

Ocular tissue samples from both eyes of each animal were collected and weights were recorded. Plasma and ocular tissue sample concentrations of Compound 1 were determined by LC-MS/MS.

New Zealand White rabbits weighing 2.5 to 3.5 kg were used on this study. Rabbits were housed one per cage. Animals were not fasted and only healthy animals with no ocular illness were used. Two rabbits per group were sacrificed at each of four ocular tissue sampling time points for a total of eight rabbits per group. The study design is presented in TABLE 3 and TABLE 4.

Animals were anesthetized for ocular (topical) and intravitreal dosing following the 12IA7 IACUC protocol. Each rabbit received a bolus dose of test formulation either via topical ocular administration 3 times daily on Days 1 and 2 (at 0, 6, and 12 hours), and once on Day 3 (at 0 hours) into both eyes; via intravitreal administration into both eyes once on Day 1 (at 0 hours); or via subcutaneous administration 2 times daily on Days 1 and 2 (at 0 and 8 hours) and once daily on Day 3 (at 0 hours). Doses were given within an approximately 1 hour window each day where applicable.

Pre-screening clinical ophthalmic exams were done prior to study (includes slit-lamp biomicroscopy and indirect ophthalmoscopy). Ocular findings were scored using the McDonald-Shadduck Score System, and only animals that scored zero in all categories were used in the study.

On Day 1, for intravitreal administration, or on Day 3, for topical ocular and subcutaneous administration, at the appropriate ocular tissue collection time points, animals were euthanized and both eyes were enucleated immediately. Following enucleation, each eye was rinsed with phosphate-buffered saline. Ocular tissue samples from both eyes of each animal were collected at predetermined time points and weights were recorded. All the samples were frozen immediately on dry ice, and stored at −60° C. to −80° C. pending bioanalysis.

Each blood sample was collected on Day 3 post dose at pre-determined time points from the rabbits via an ear vessel and placed into chilled polypropylene tubes containing sodium heparin as an anticoagulant. Samples were spun by centrifuge at 4° C. and 3,000×g for 5 minutes. Samples were maintained chilled throughout processing. Each plasma sample was placed on dry ice and stored in a freezer at −60° C. to −80° C. pending bioanalysis.

TABLE 3 and TABLE 4 show a summary of the study design.

TABLE 3

| Dose group | Test compound | Dosing route | Animals per time point N= | Total animals | Dosing regimen | Dose |
|---|---|---|---|---|---|---|
| 1 | Compound 1 sodium salt | Topical ocular (OU) | 2 | 8 | Day 1: 0, 6, and 12 hr; Day 2: 0, 6, and 12 hr; Day 3: 0 hr | 1.2 mg per eye |
| 2 | Compound 1 sodium salt | Subcutaneous | 2 | 8 | Day 1: 0 and 8 hr; Day 2: 0 and 8 hr; Day 3: 0 hr | 5 mg/kg |
| 3 | Compound 1 free acid | Subcutaneous | 2 | 8 | Day 1: 0 hr; Day 2: 0 hr; Day 3: 0 hr | 5 mg/kg |
| 4 | Compound 1 sodium salt | Intravitreal (OU) | 2 | 8 | Day 1: 0 hr | 2.5 mg per eye |
| 5 | Compound 1 free acid | Intravitreal (OU) | 2 | 8 | Day 1: 0 hr | 2.5 mg per eye |

OU: both eyes

TABLE 4

| Dose group | Dosing formulation conc. | Dosing volume | Vehicle | Plasma sampling time points (Day 3) | Ocular tissue sampling time points (Day 3) |
|---|---|---|---|---|---|
| 1 | 40 mg/mL (solution) | 30 μL per eye | 15% HPβCD + 1% dextrose in water | 30 min; 1, 2, and 4 hr | 30 min, 1, 2, and 4 hr |
| 2 | 40 mg/mL (solution) | 0.125 mL/kg | 15% HPβCD + 1% dextrose in water | 15* and 30 min; 1, 2, and 4 hr | 30 min, 1, 2, and 4 hr |
| 3 | 25 mg/mL (solution) | 0.2 mL/kg | 40 mM phosphate buffer pH 4.0 + 2.5% dextrose in water | 15* and 30 min; 1, 2, and 4 hr | 30 min, 1, 2, and 4 hr |
| 4 | 25 mg/mL (solution) | 100 μL per eye | 10% HPβCD + 2% dextrose in water | 1**, 3**, 6, and 24 hr | 6, 24, 48, and 72 hours |
| 5 | 25 mg/mL (solution) | 100 μL per eye | 40 mM phosphate buffer pH 4.0 + 2.5% dextrose in water | 1**, 3**, 6, and 24 hr | 6, 24, 48, and 72 hours |

*Rabbits from the 30 minute ocular tissue sampling time point were bled at 15 minutes post dose.
**Rabbits from the 48 hour ocular tissue sampling time point were bled for the 1 hour plasma sampling. Rabbits from the 72 hour ocular tissue sampling time point were bled for the 3 hour plasma sampling.
HPβCD: hydroxypropyl-beta-cyclodextrin An LC-MS/MS method was developed for the determination of Compound 1 in rabbit aqueous tissues (plasma, aqueous and vitreous humor) and solid ocular tissue samples. A pre-study standard curve was analyzed to determine the specificity, range, and lower limit of quantitation of the method. Plasma and tissue homogenate study samples were extracted and analyzed. All the samples were treated identically to the standards.

One eight-point standard curve was used in each analytical batch. To be accepted, each batch must have had at least five of eight standards with accuracy within ±20% of nominal, except at the lower limit of quantification (LLOQ), where ±25% was acceptable.

Pharmacokinetic parameters were calculated from the time course of the plasma concentration. The maximum plasma concentration ($C_{max}$) and time to the maximum plasma drug concentration ($T_{max}$) were the observed values for each concentration-time profiles. The area under the plasma drug concentration-time curve ($AUC_{last}$, with last being from time 0 to the last quantifiable point) was calculated using the trapezoidal formula. The mean residence time $MRT_{last}$ was calculated as a ratio of $AUMC_{last}$ (area under the first movement curve) to $AUC_{last}$.

No ocular abnormalities were noted in any animals in any of the dose groups.

Individual and average concentrations for Compound 1 are shown in TABLES 5-18. Concentration versus time data is plotted in FIGS. 3-16. All data are expressed as ng/g of the free drug. Samples that were below the limit of quantitation (0.2 ng/mL) were not used in the calculation of averages.

Figure 3:
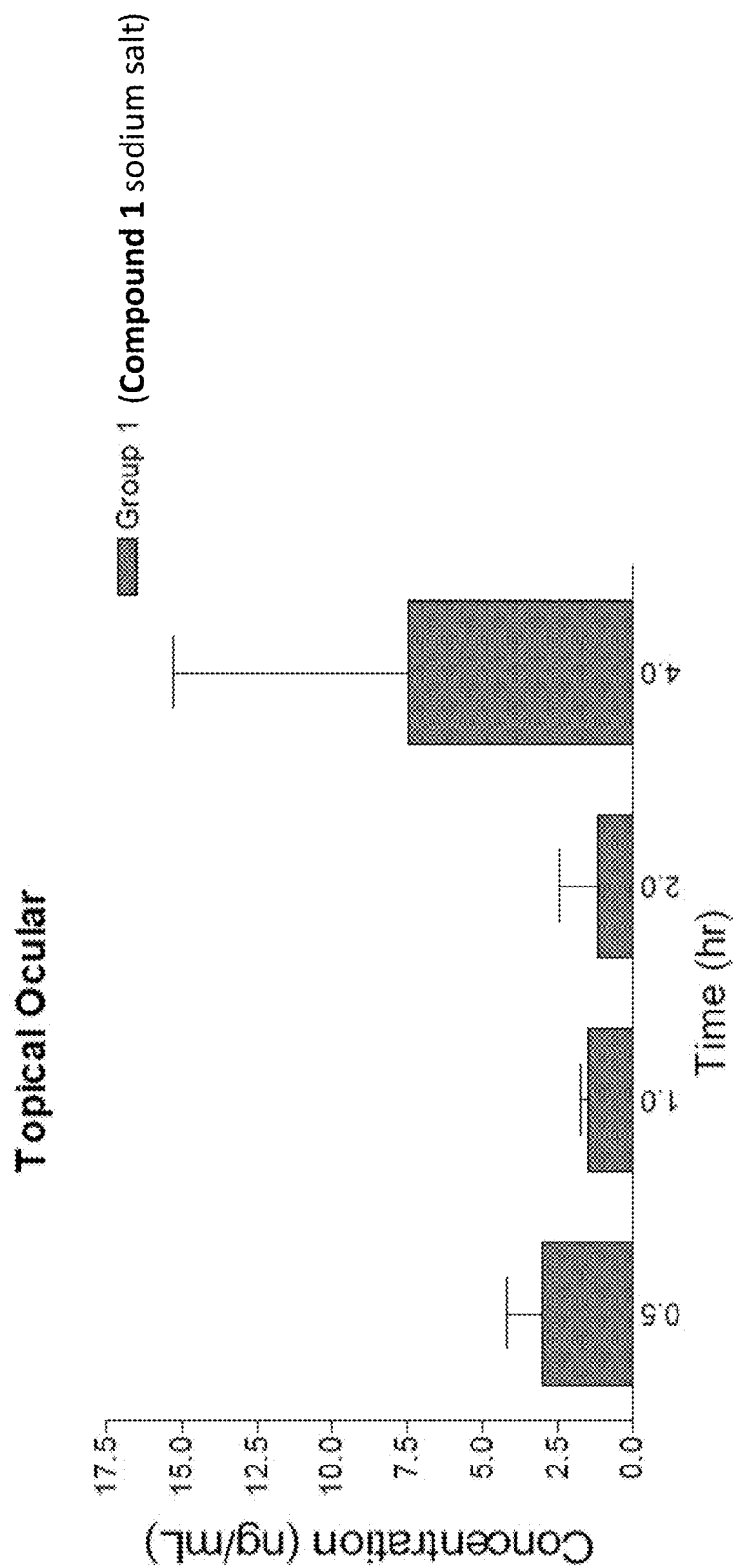
FIG. 3 illustrates changes in average plasma concentration of Compound 1 after topical ocular administration in male New Zealand White rabbits.
Figure 4:
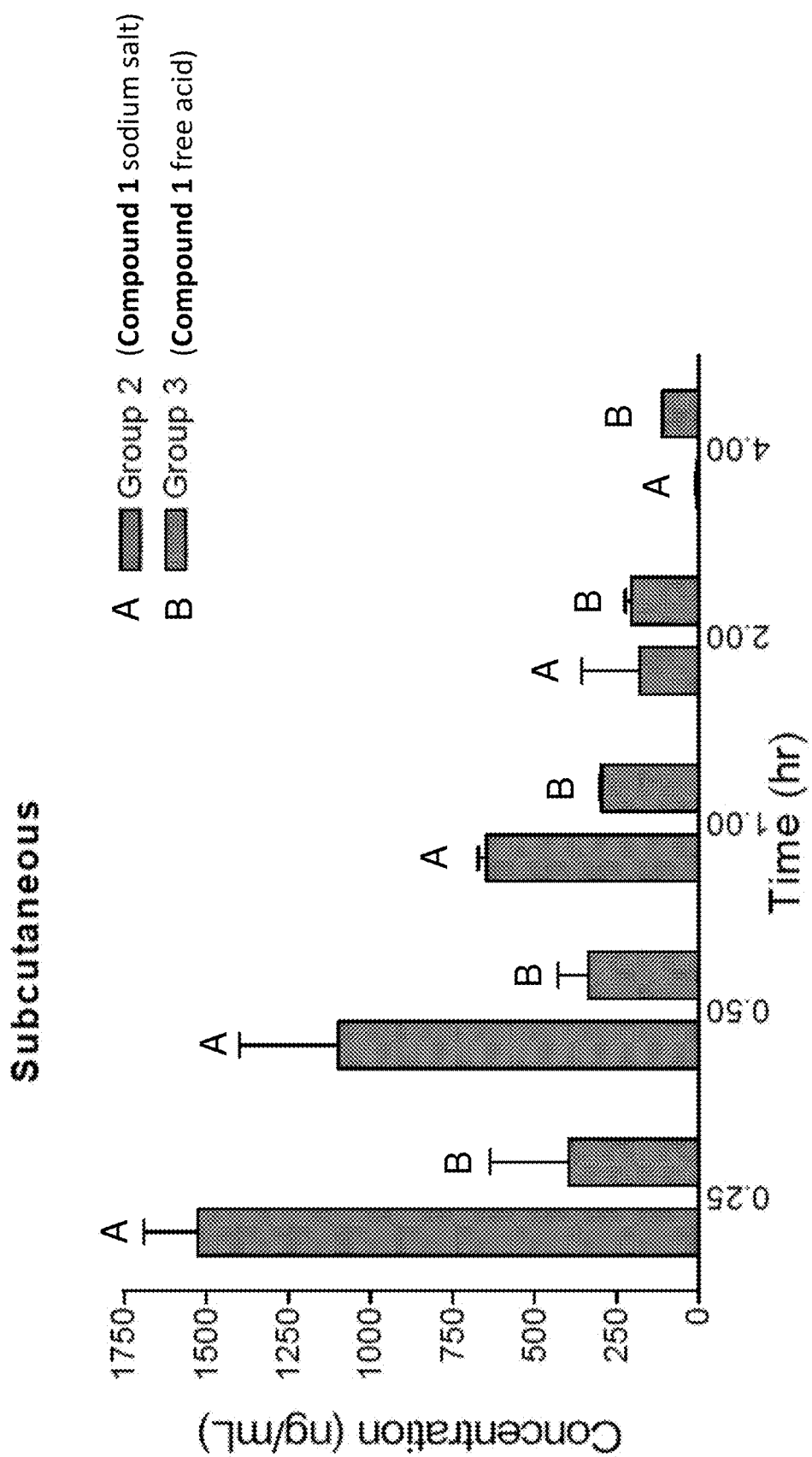
FIG. 4 illustrates changes in average plasma concentration of Compound 1 after subcutaneous administration in male New Zealand White rabbits. A: Compound 1 sodium salt; B: Compound 1 free acid.
Figure 5:
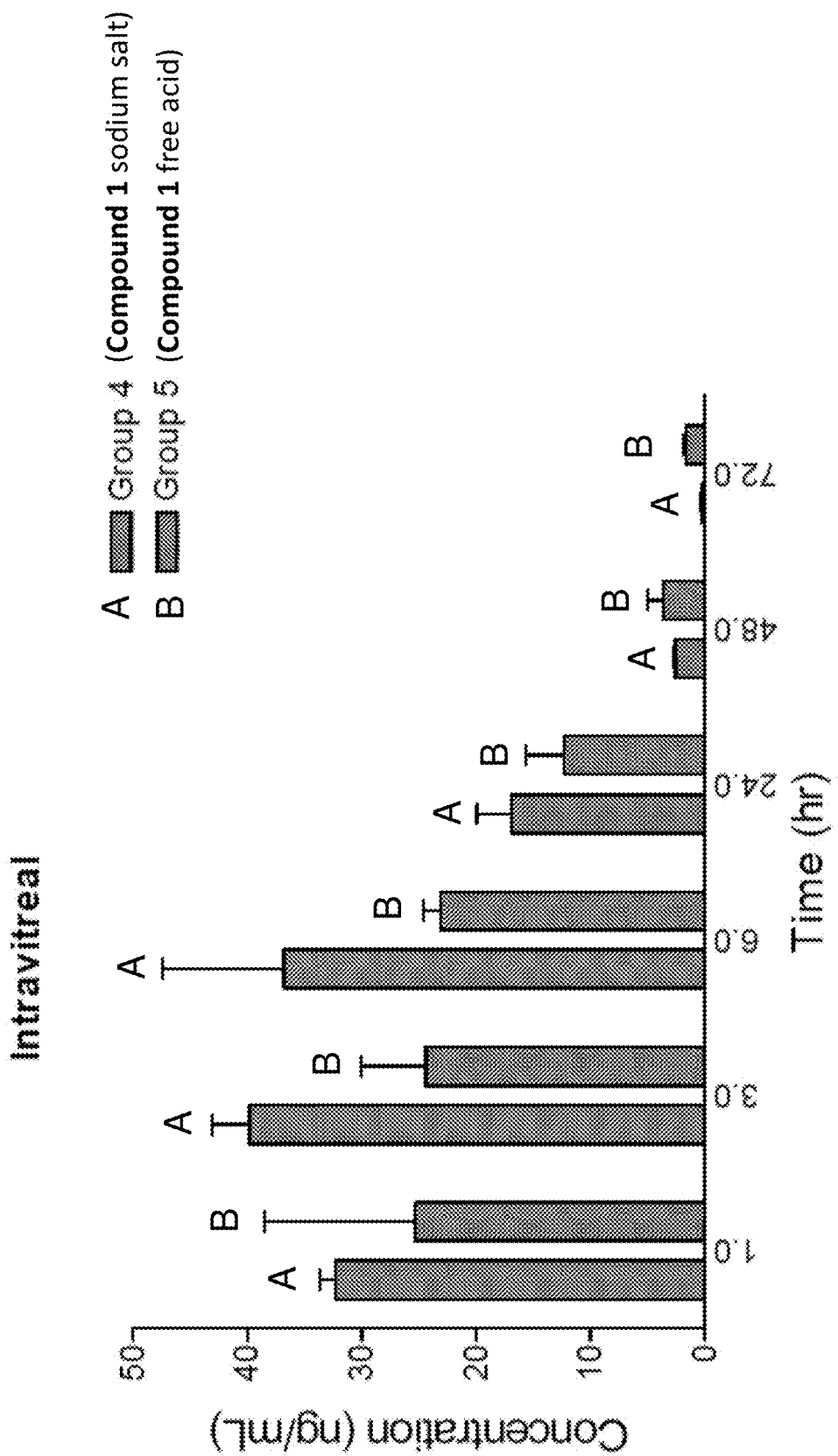
FIG. 5 illustrates changes in average plasma concentration of Compound 1 after intravitreal administration in male New Zealand White rabbits. A: Compound 1 sodium salt; B: Compound 1 free acid.
Figure 6:
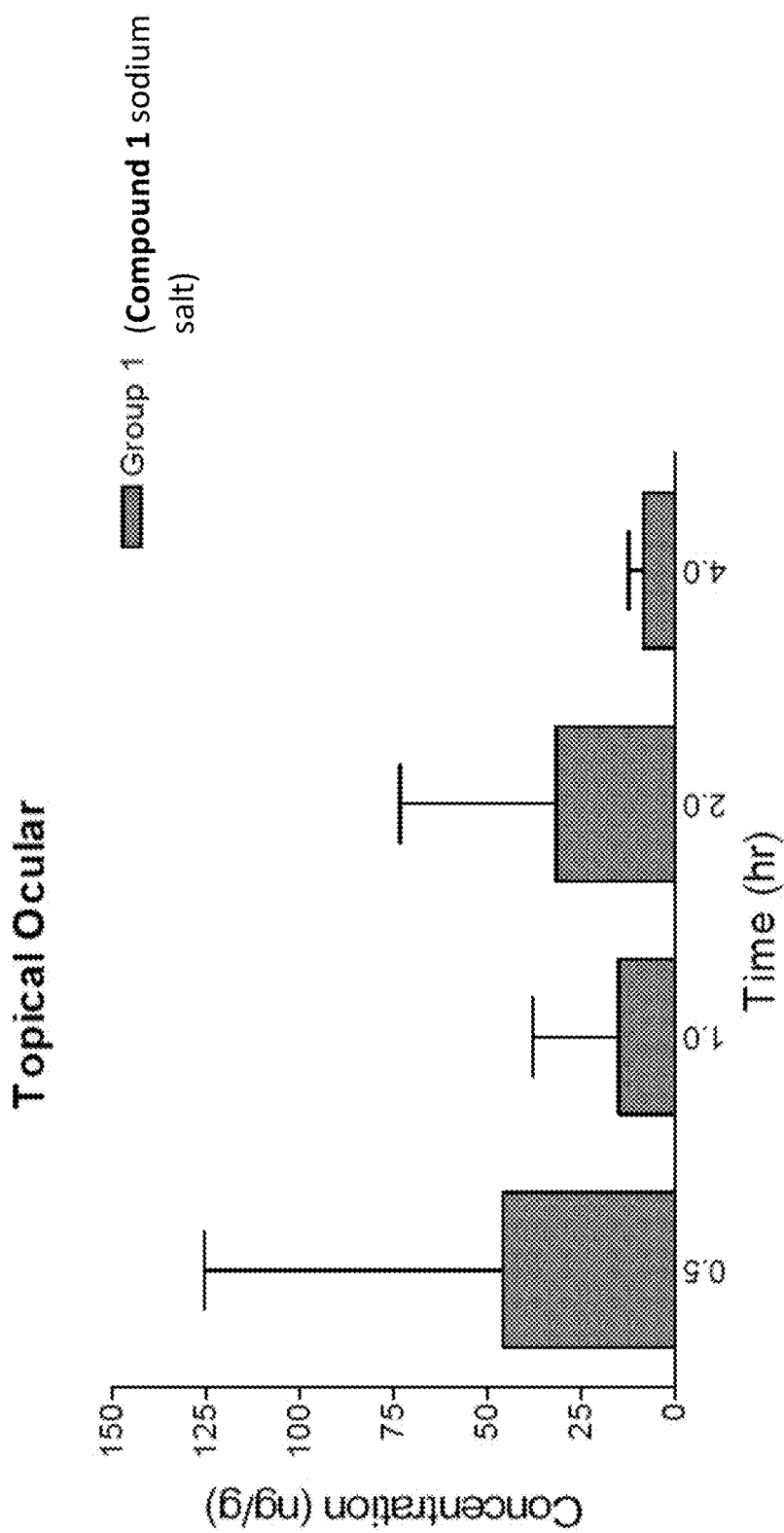
FIG. 6 illustrates changes in average aqueous humor concentrations after topical ocular administration of Compound 1 in male New Zealand White rabbits.
Figure 7:
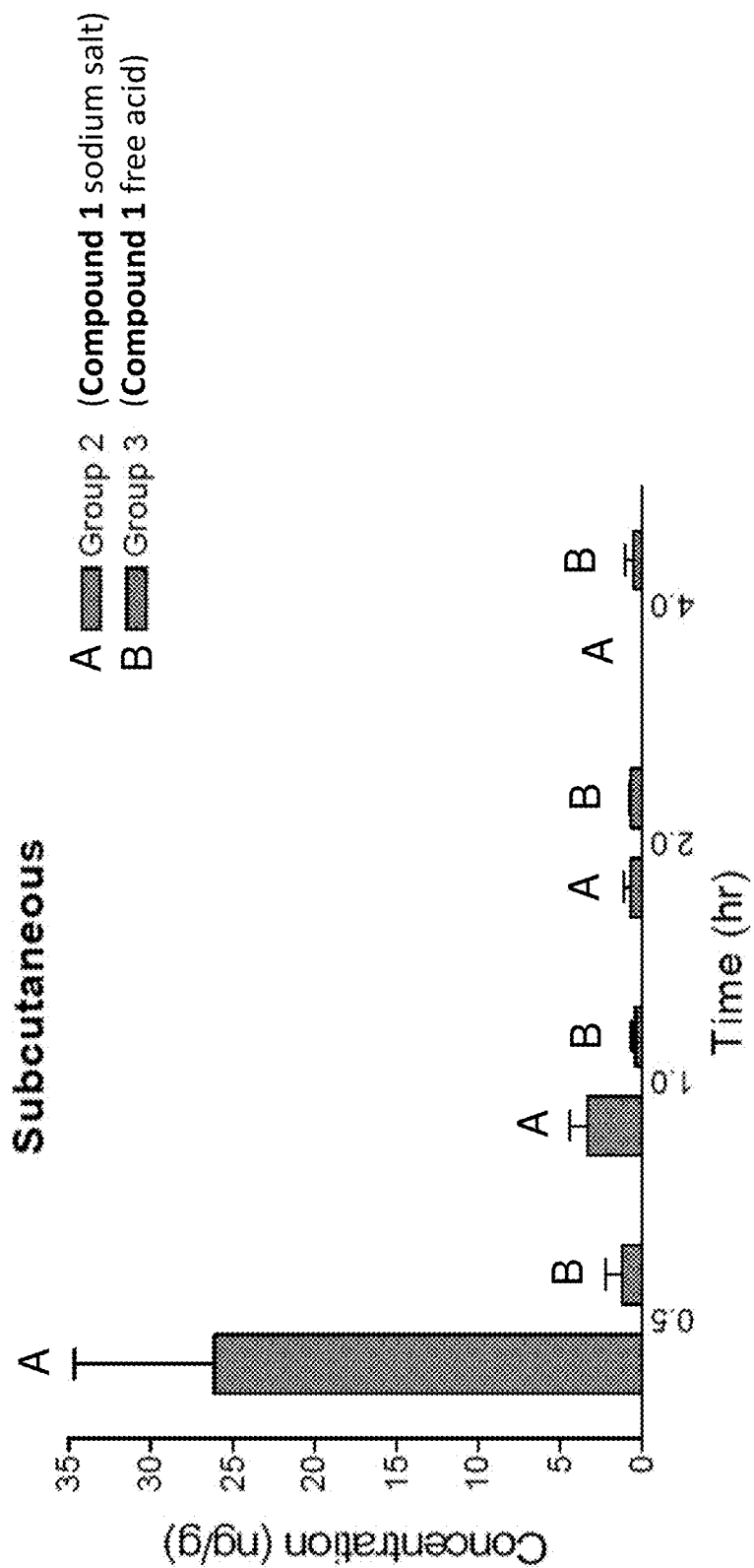
FIG. 7 illustrates changes in average aqueous humor concentrations after subcutaneous administration of Compound 1 in male New Zealand White rabbits. A: Compound 1 sodium salt; B: Compound 1 free acid.
Figure 8:
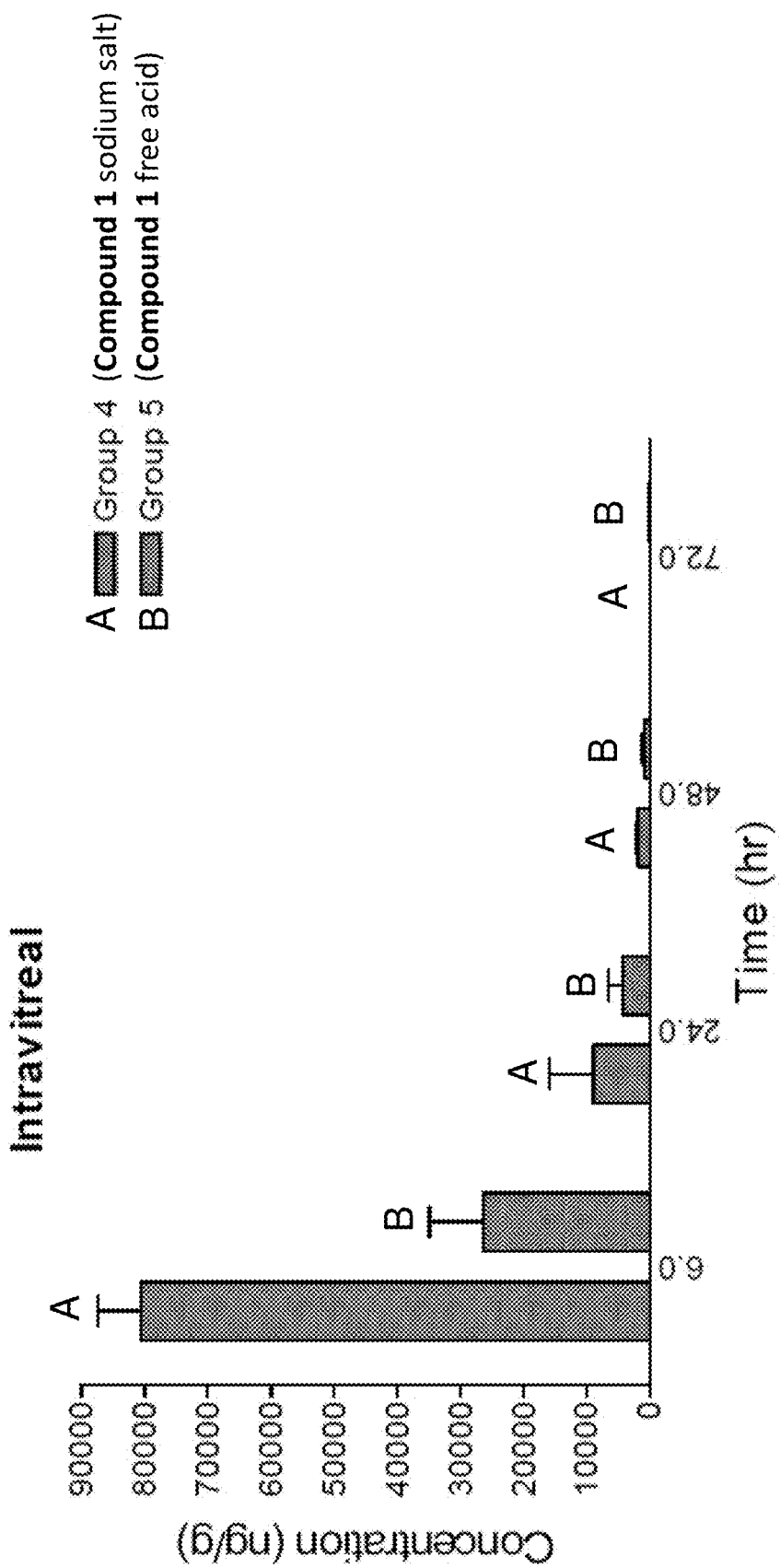
FIG. 8 illustrates changes in average aqueous humor concentrations after intravitreal administration of Compound 1 in male New Zealand White rabbits. A: Compound 1 sodium salt; B: Compound 1 free acid.
Figure 9:
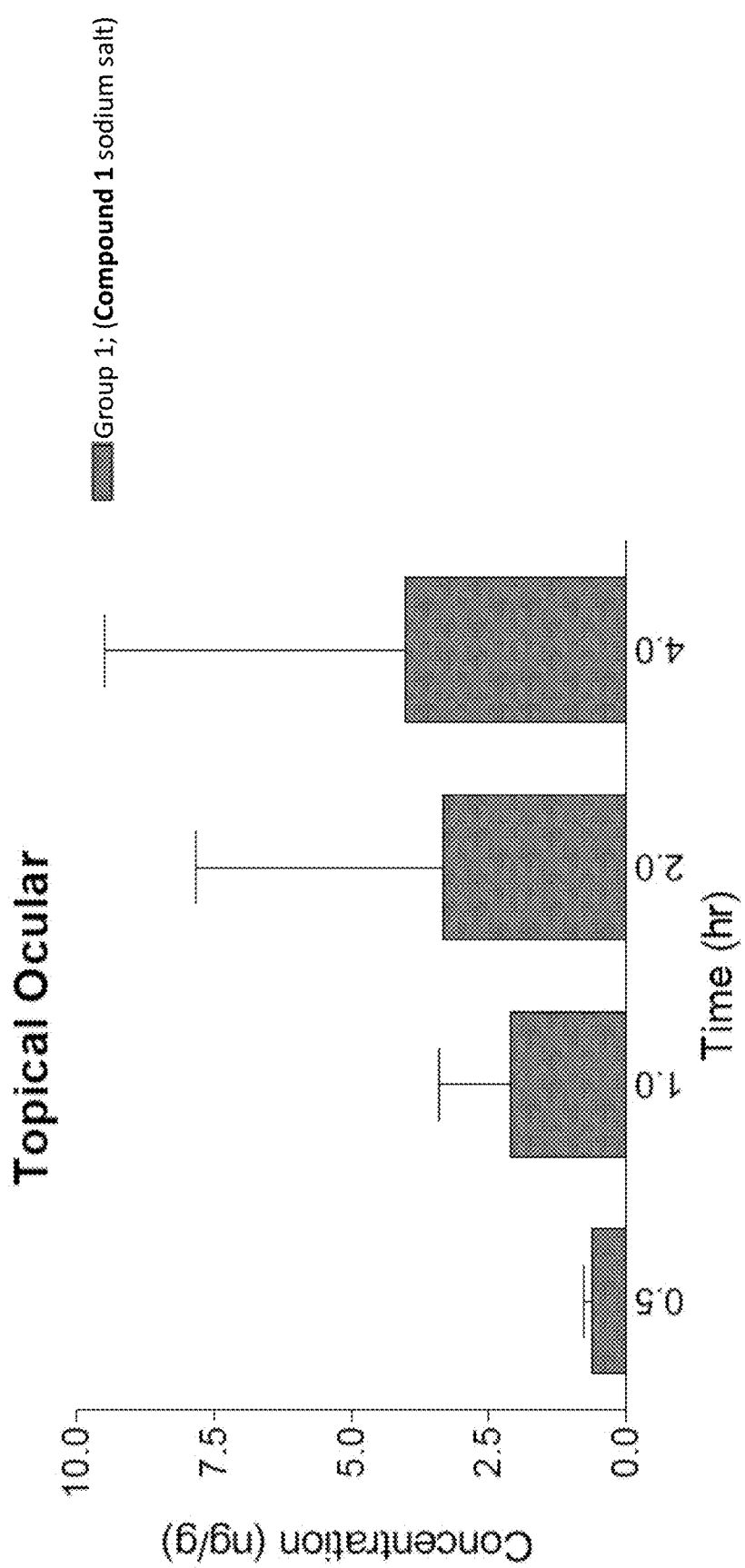
FIG. 9 illustrates average vitreous humor concentrations after topical ocular administration of Compound 1 in male New Zealand White rabbits.
Figure 10:
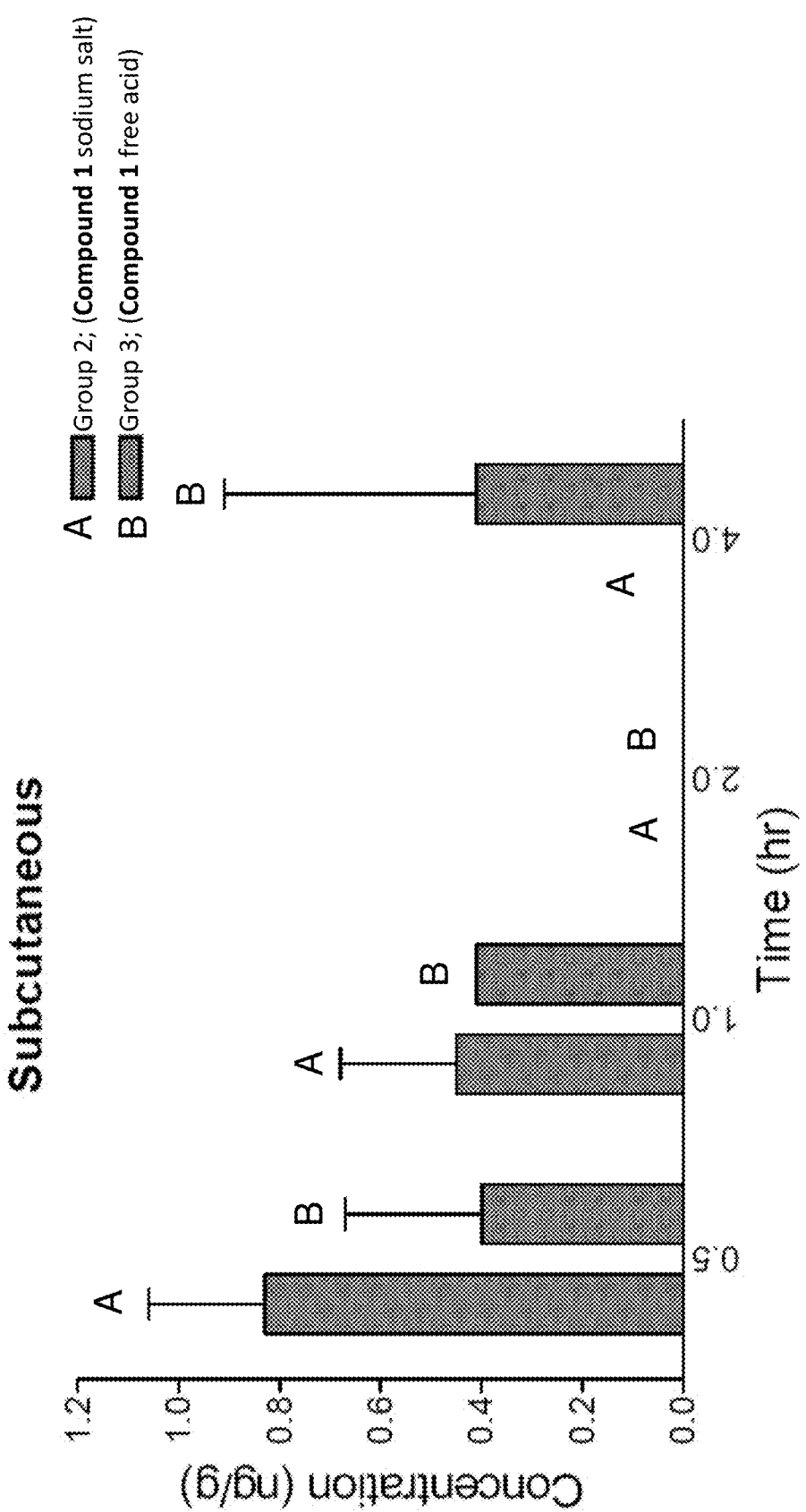
FIG. 10 illustrates average vitreous humor concentrations after subcutaneous administration of Compound 1 in male New Zealand White rabbits. A: Compound 1 sodium salt; B: Compound 1 free acid.
Figure 11:
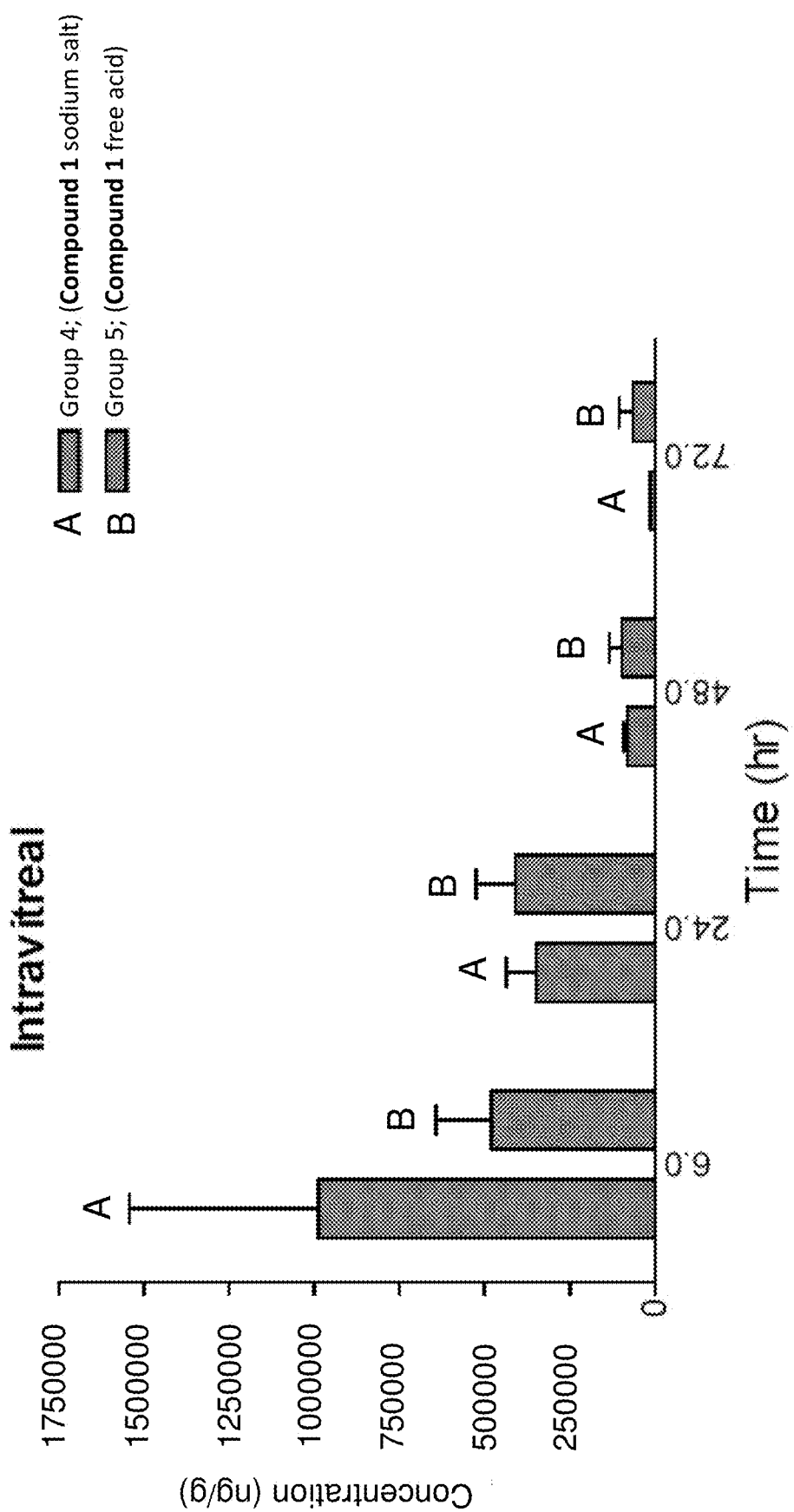
FIG. 11 illustrates average vitreous humor concentrations after intravitreal administration of Compound 1 in male New Zealand White rabbits. A: Compound 1 sodium salt; B: Compound 1 free acid.
Figure 12:
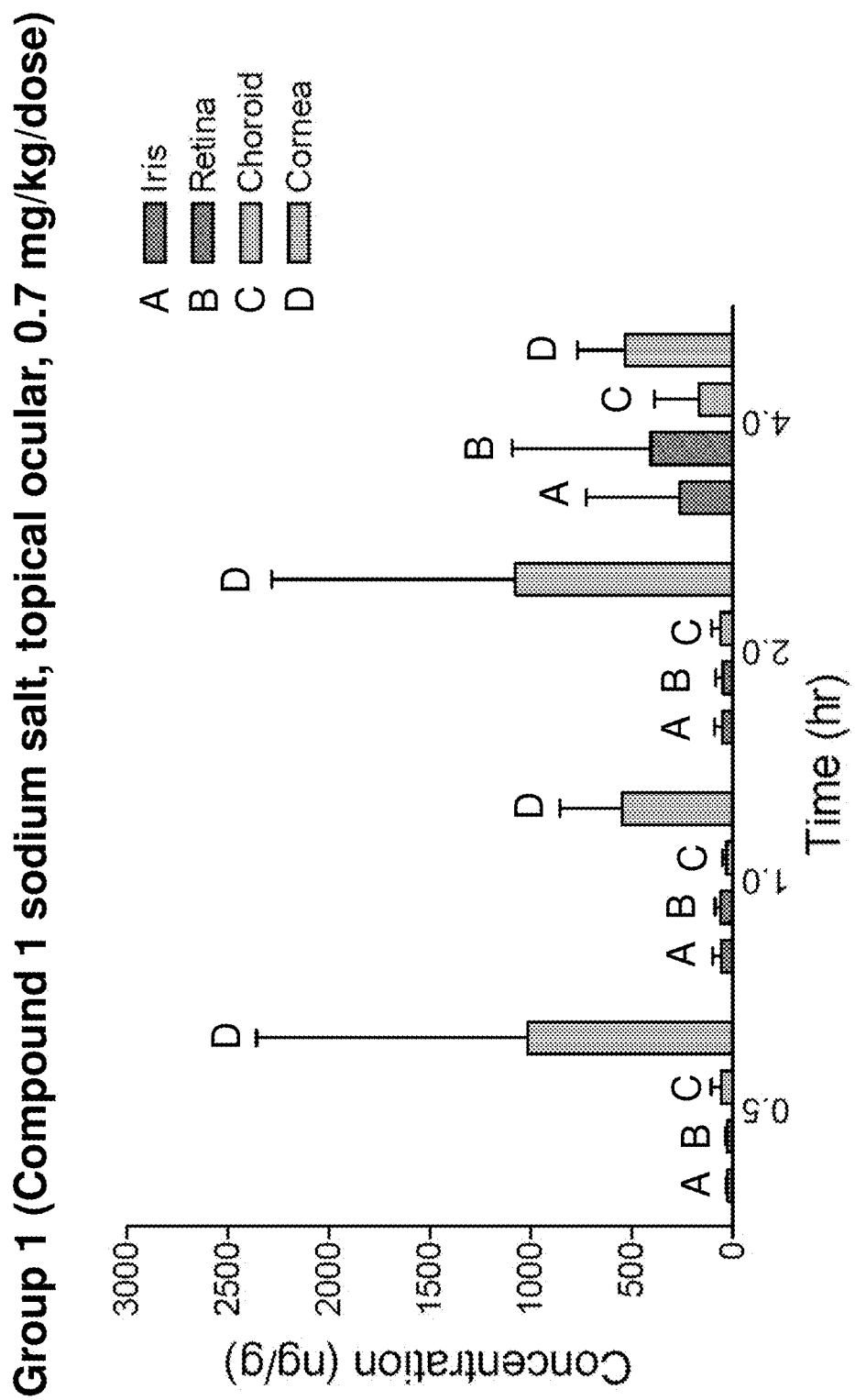
FIG. 12 illustrates average iris, retina, choroid, and cornea tissue concentrations after topical ocular administration of Compound 1 in male New Zealand White rabbits at 1.2 mg/eye (~0.7 mg/kg/dose). A: Iris; B: Retina; C: Choroid; D: Cornea.
Figure 13:
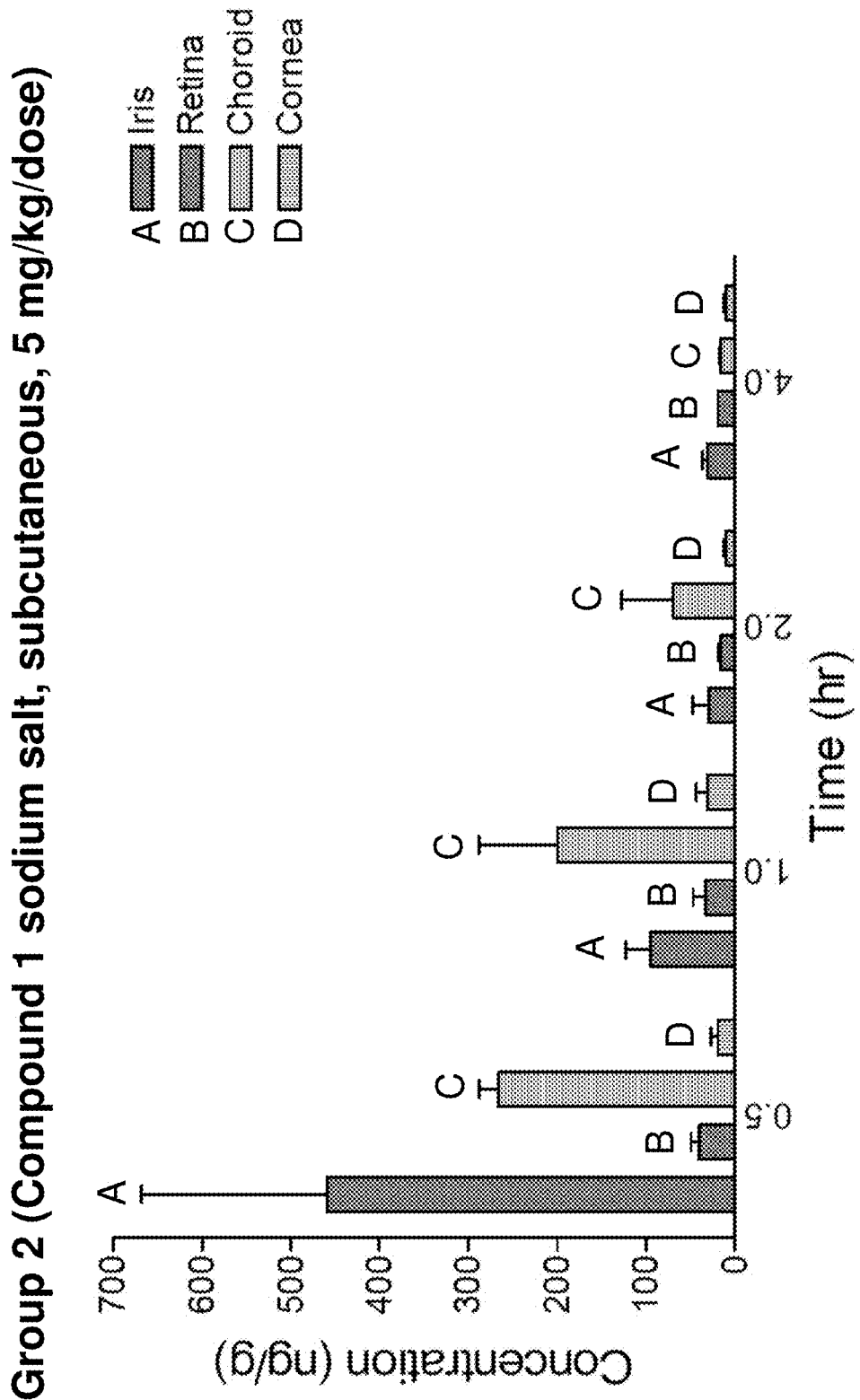
FIG. 13 illustrates individual and average iris, retina, choroid, and cornea tissue concentrations after subcutaneous administration of Compound 1 in male New Zealand White rabbits. A: Iris; B: Retina; C: Choroid; D: Cornea.
Figure 14:
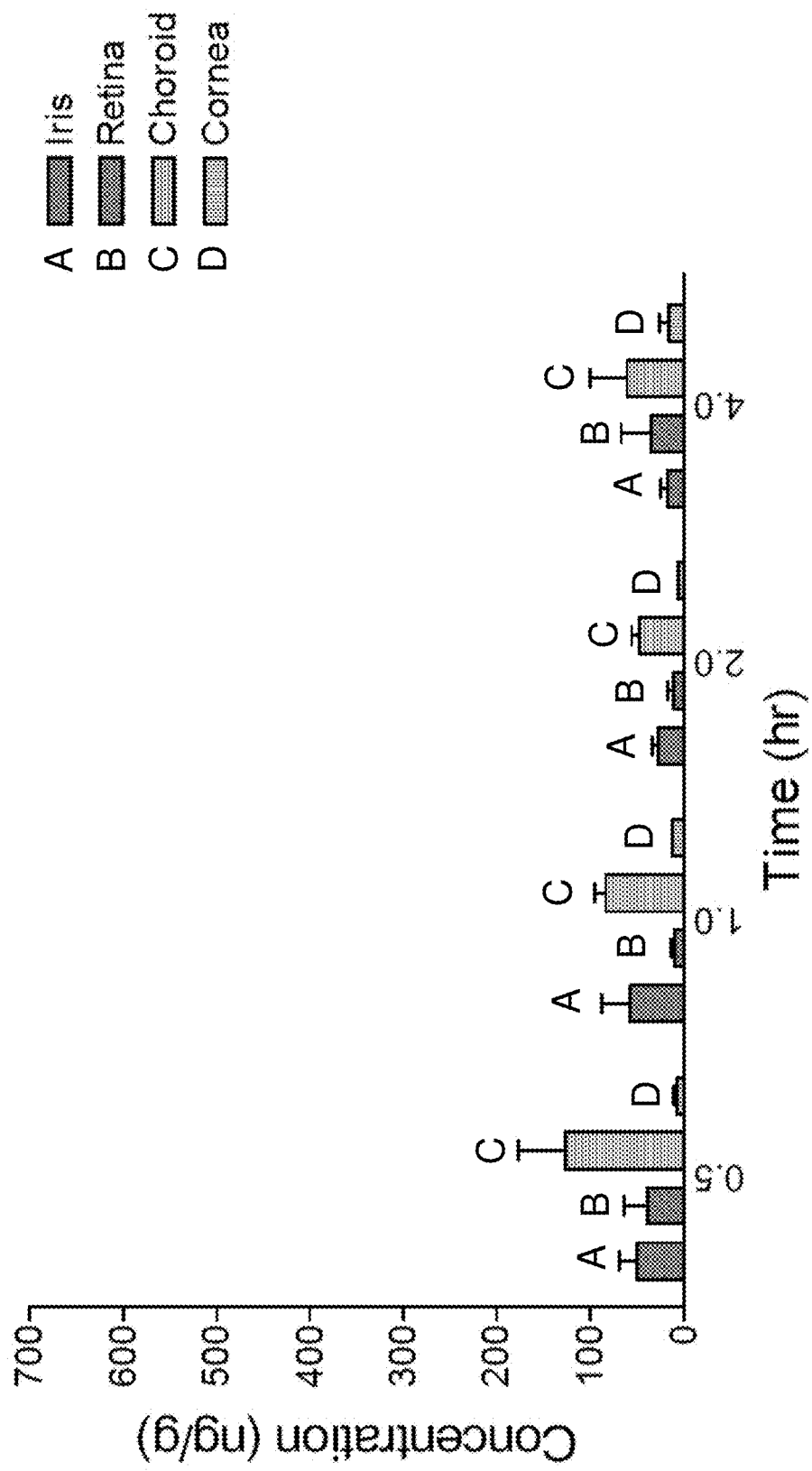
FIG. 14 illustrates individual and average iris, retina, choroid, and cornea tissue concentrations after subcutaneous administration of Compound 1 in male New Zealand White rabbits. A: Iris; B: Retina; C: Choroid; D: Cornea.
Figure 15:
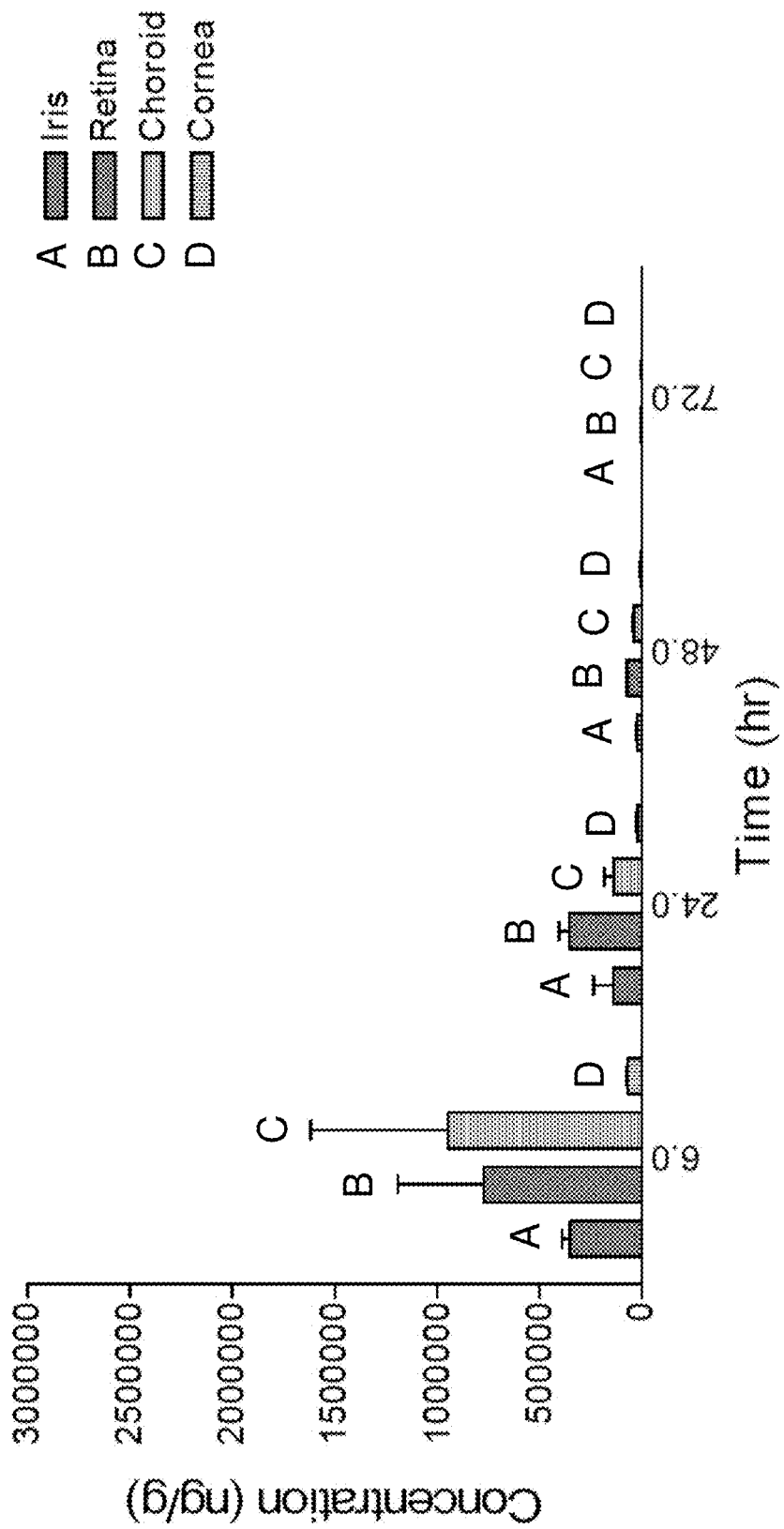
FIG. 15 illustrates average iris, retina, choroid, and cornea tissue concentrations after intravitreal administration of Compound 1 in male New Zealand White rabbits. A: Iris; B: Retina; C: Choroid; D: Cornea.
Figure 16:
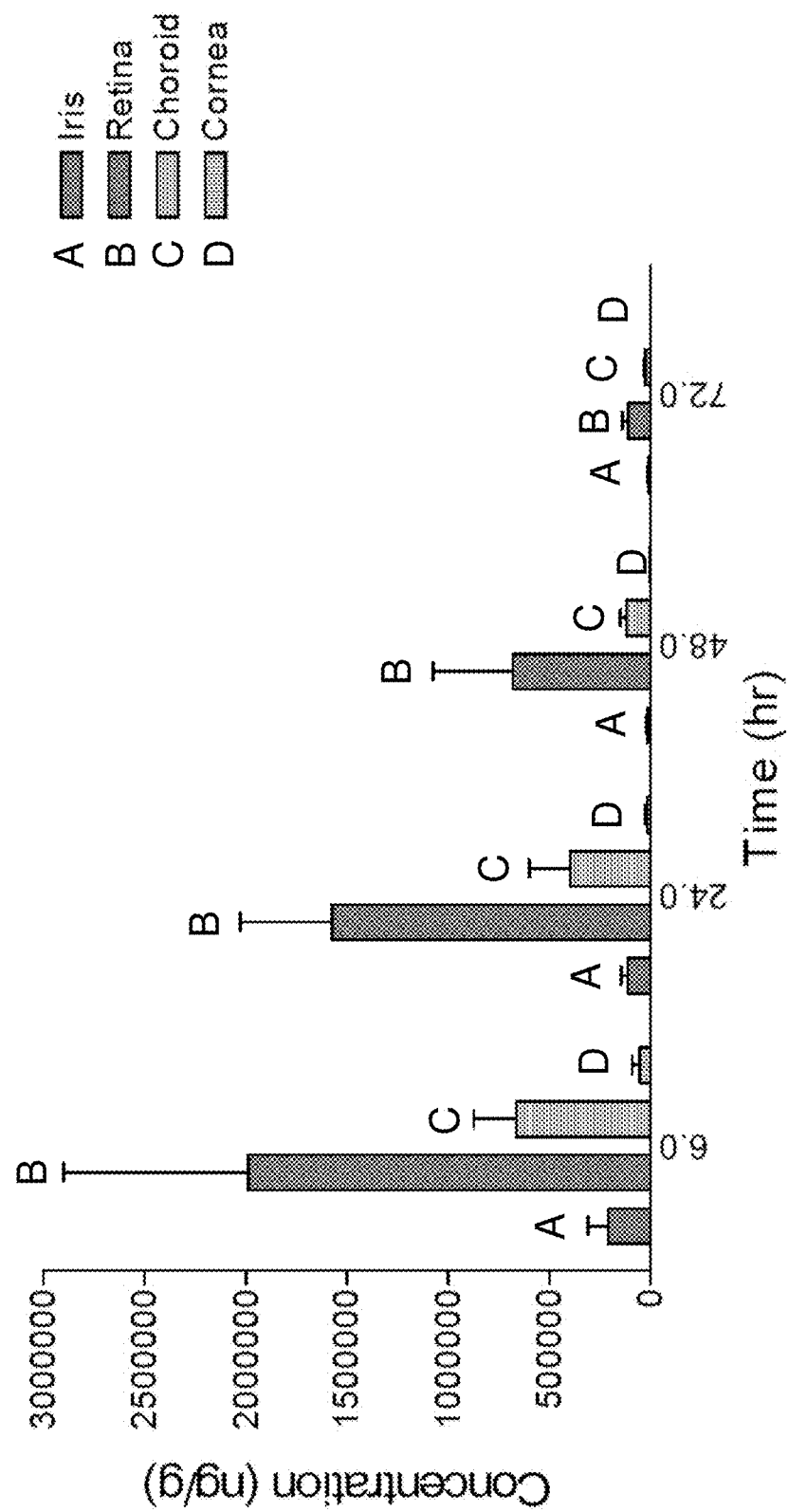
FIG. 16 illustrates average iris, retina, choroid, and cornea tissue concentrations after intravitreal administration of Compound 1 in male New Zealand White rabbits. A: Iris; B: Retina; C: Choroid; D: Cornea.

As seen in FIG. 3, topical ocular administration of the sodium salt of Compound 1 resulted in an increase in Compound 1 plasma concentration as measured at the 4 hour mark. As seen in FIG. 4, subcutaneous administration of the sodium salt of Compound 1 resulted in generally increased plasma concentrations as compared to the free acid up to one hour post-administration. As seen in FIG. 5, intravitreal administration of the sodium salt of Compound 1 resulted in slightly higher plasma concentrations as compared to the free acid up to twenty-four hours post-administration. As seen in FIG. 6, topical ocular administration of Compound 1 (sodium salt) resulted in aqueous humor concentrations of below 50 ng/g of Compound 1 over four hours. As seen in FIG. 7, subcutaneous administration of the sodium salt of Compound 1 resulted in increased aqueous humor concentrations as compared to the free acid at early time points. As seen in FIG. 8, intravitreal administration of the sodium salt of Compound 1 resulted in higher aqueous humor concentrations up to forty-eight hours post-administration as compared to the free acid. As seen in FIG. 9, topical ocular administration of Compound 1 (sodium salt) resulted in increased vitreous humor concentrations of Compound 1 over time. As seen in FIG. 10, subcutaneous administration of the sodium salt of Compound 1 resulted in increased vitreous humor concentrations at 0.5 hr and 1 hr post-dosing as compared to the free acid. As seen in FIG. 11, intravitreal administration of the sodium salt of Compound 1 resulted in a higher vitreous humor concentrations at 6 hr post-dosing as compared to the free acid. As seen in FIG. 12, when Compound 1 (sodium salt) was administered via topical ocular administration at 0.7 mg/kg/dose, concentrations were generally higher in the cornea as compared to the iris, retina, and choroid. As seen in FIG. 13, when Compound 1 (sodium salt) was administered subcutaneously at 5 mg/kg/dose, concentrations were generally higher in the iris and choroid as compared to the retina and cornea. As seen in FIG. 14, when Compound 1 (free acid) was administered subcutaneously at 5 mg/kg/dose, concentrations were generally higher in the iris and choroid as compared to the retina and cornea. As seen in FIG. 15, when Compound 1 (sodium salt) was administered intravitreally at 1.55 mg/kg, concentrations were generally higher in the retina and choroid as compared to the iris and cornea. As seen in FIG. 16, when Compound 1 (free acid) was administered intravitreally at 1.54 mg/kg, concentrations were generally higher in the retina and choroid as compared to the iris and cornea.

Systemic exposure of Compound 1, as measured in plasma, was confirmed by all routes and formulations. Mean plasma $C_{max}$ was approximately 3-fold higher following subcutaneous administration with a Compound 1 (sodium salt) solution compared to the subcutaneous administration of a Compound 1 (free acid) suspension, and approximately 2-fold higher following intravitreal administration with Compound 1 (sodium salt) solution compared to the intravitreal administration of a Compound 1 (free acid) suspension. Mean plasma $AUC_{last}$ was approximately 2-fold higher following subcutaneous administration with a Compound 1 (sodium salt) solution compared to the subcutaneous administration of a Compound 1 (free acid) suspension, whereas mean plasma $AUC_{last}$ was comparable between the two dose formulations following intravitreal administration. Mean plasma $T_{max}$ was observed 15 minutes postdose following subcutaneous administration with both formulations, 3 and 1 hours postdose following intravitreal administration with Compound 1 (sodium salt) and Compound 1 (free acid), respectively, and 4 hours post dose following ocular administration of Compound 1 (sodium salt).

Ocular tissue concentrations were generally higher from subcutaneous and intravitreal administration with a Compound 1 (sodium salt) solution compared to the Compound 1 (free acid) suspension. The rank order of exposure in aqueous and vitreous humor was intravitreal>>topical ocular>subcutaneous administration. Intravitreal administration of both test formulations resulted in higher concentrations in the iris, retina, choroid, and cornea relative to subcutaneous or ocular topical administration. The ocular tissue concentrations of Compound 1 in all ocular tissues persisted at 72 hours after dosing following intravitreal administration of both test formulations, with higher concentrations observed with the Compound 1 (free acid) suspension formulation relative to the Compound 1 (sodium salt) solution formulation.

TABLE 5 shows individual and average plasma concentrations (ng/mL) and pharmacokinetic parameters for Compound 1 (sodium salt) after topical ocular administration in male New Zealand White rabbits at 1.2 mg/eye (~0.7 mg/kg/dose) (Group 1).

TABLE 5

Topical; 15% HPβCD + 1% Dextrose in water

| Time point (hr) | Rabbit # | Conc. (ng/mL) | Average (ng/mL) | SD |
|---|---|---|---|---|
| 0.50 | 1 | 3.84 | 3.03 | 1.15 |
|  | 2 | 2.21 |  |  |
| 1.0 | 3 | 1.28 | 1.46 | 0.25 |
|  | 4 | 1.63 |  |  |
| 2.0 | 5 | 0.241 | 1.14 | 1.27 |
|  | 6 | 2.04 |  |  |
| 4.0 | 7 | 13.0 | 7.48 | 7.81 |
|  | 8 | 1.95 |  |  |

Pharmacokinetic Parameters

| | |
|---|---|
| $C_{max}$ (ng/mL) ± SE | 7.48 ± 5.53 |
| $t_{max}$ (hr) | 4.00 |
| $t_{1/2}$ (hr) | ND[1] |
| $MRT_{last}$ (hr) | 2.98 |
| $AUC_{last}$ (hr · ng/mL) ± SE | 11.8 ± 5.70 |
| $AUC_\infty$ (hr · ng/mL) | ND[1] |
| Dose Normalized Values[2] | |
| $AUC_{last}$ (hr · kg · ng/mL/mg) | 16.8 ± 8.15 |
| $AUC_\infty$ (hr · kg · ng/mL/mg) | ND[1] |

ND: Not Determined
[1]Not determined due to terminal log linear phase not observed
[2]Dose normalized by dividing the parameter by the total nominal dose of 0.7 mg/kg
HPβCD: 2-hydroxypropyl-β-cyclodextrin TABLE 6 shows the individual and average plasma concentrations (ng/mL) and pharmacokinetic parameters for Compound 1 (sodium salt) after subcutaneous administration in male New Zealand White Rabbits at 5 mg/kg/dose (Group 2).

TABLE 6

Subcutaneous; 15% HPβCD + 1% Dextrose in water (solution)

| Time point (hr) | Rabbit # | Conc. (ng/mL) | Average (ng/mL) | SD |
|---|---|---|---|---|
| 0.25 | 9 | 1640 | 1525 | 163 |
|  | 10 | 1410 |  |  |
| 0.50 | 9 | 883 | 1097 | 302 |
|  | 10 | 1310 |  |  |
| 1.0 | 11 | 628 | 646 | 25.5 |
|  | 12 | 664 |  |  |
| 2.0 | 13 | 55.5 | 180 | 176 |
|  | 14 | 305 |  |  |
| 4.0 | 15 | 7.98 | 7.76 | 0.32 |
|  | 16 | 7.53 |  |  |

Pharmacokinetic Parameters

| | |
|---|---|
| $C_{max}$ (ng/mL) ± SE | 1525 ± 115 |
| $t_{max}$ (hr) | 0.25 |
| $t_{1/2}$ (hr) | 0.47 |
| $MRT_{last}$ (hr) | 0.87 |
| $AUC_{last}$ (hr · ng/mL) ± SE | 1555 ± 195 |
| $AUC_\infty$ (hr · ng/mL) | 1560 |
| Dose Normalized Values[1] | |
| $AUC_{last}$ (hr · kg · ng/mL/mg) | 311 ± 38.9 |
| $AUC_\infty$ (hr · kg · ng/mL/mg) | 312 |

[1]Dose normalized by dividing the parameter by the total nominal dose of 5 mg/kg
Data points used for half-life determination are in bold.

TABLE 7 shows individual and average plasma concentrations (ng/ml) and pharmacokinetic parameters for Compound 1 (free acid) after subcutaneous administration in male New Zealand White rabbits at 5 mg/kg/dose (Group 3).

TABLE 7

Subcutaneous; 40 mM Phosphate Buffer pH 4.0 + 2.5% Dextrose in water (suspension)

| Time point (hr) | Rabbit # | Conc. (ng/mL) | Average (ng/mL) | SD |
|---|---|---|---|---|
| 0.25 | 17 | 225 | 395 | 240 |
|  | 18 | 565 |  |  |
| 0.50 | 17 | 272 | 337 | 91.2 |
|  | 18 | 401 |  |  |
| 1.0 | 19 | 300 | 295 | 7.78 |
|  | 20 | 289 |  |  |
| 2.0 | 21 | 194 | 206 | 16.3 |
|  | 22 | 217 |  |  |
| 4.0 | 23 | 111 | 110 | 2.12 |
|  | 24 | 108 |  |  |

Pharmacokinetic Parameters

| | |
|---|---|
| $C_{max}$ (ng/mL) ± SE | 395 ± 170 |
| $t_{max}$ (hr) | 0.25 |
| $t_{1/2}$ (hr) | 2.12 |
| $MRT_{last}$ (hr) | 1.58 |
| $AUC_{last}$ (hr · ng/mL) ± SE | 864 ± 69 |
| $AUC_\infty$ (hr · ng/mL) | 1198 |

Dose Normalized Values[1]

| | |
|---|---|
| $AUC_{last}$ (hr · kg · ng/mL/mg) | 173 ± 13.8 |
| $AUC_\infty$ (hr · kg · ng/mL/mg) | 240 |

[1]Dose normalized by dividing the parameter by the total nominal dose of 5 mg/kg
Data points used for half-life determination are in bold.

TABLE 8 shows individual and average plasma concentrations (ng/ml) and pharmacokinetic parameters for Compound 1 (sodium salt) after intravitreal administration in male New Zealand White rabbits at 2.5 mg/eye (~1.55 mg/kg) (Group 4).

TABLE 8

Intravitreal; 10% HPβCD + 2% Dextrose in water (solution)

| Time point (hr) | Rabbit # | Conc. (ng/mL) | Average (ng/mL) | SD |
|---|---|---|---|---|
| 1.0 | 25 | 33.2 | 32.3 | 1.34 |
|  | 26 | 31.3 |  |  |
| 3.0 | 27 | 37.5 | 39.8 | 3.25 |
|  | 28 | 42.1 |  |  |
| 6.0 | 29 | 29.3 | 36.8 | 10.6 |
|  | 30 | 44.3 |  |  |
| 24.0 | 31 | 19.0 | 16.9 | 3.04 |
|  | 32 | 14.7 |  |  |
| 48.0 | 25 | 2.70 | 2.58 | 0.18 |
|  | 26 | 2.45 |  |  |
| 72.0 | 27 | 0.215 | 0.27 | 0.08 |
|  | 28 | 0.333 |  |  |

Pharmacokinetic Parameters

| | |
|---|---|
| $C_{max}$ (ng/mL) ± SE | 39.8 ± 2.30 |
| $t_{max}$ (hr) | 3.00 |
| $t_{1/2}$ (hr) | 8.08 |
| $MRT_{last}$ (hr) | 15.1 |
| $AUC_{last}$ (hr · ng/mL) ± SE | 953 ± 91.1 |
| $AUC_\infty$ (hr · ng/mL) | 956 |

TABLE 8-continued

Intravitreal; 10% HPβCD + 2% Dextrose in water (solution)

| Time point (hr) | Rabbit # | Conc. (ng/mL) | Average (ng/mL) | SD |
|---|---|---|---|---|

Dose Normalized Values[1]

| | |
|---|---|
| $AUC_{last}$ (hr · kg · ng/mL/mg) | 615 ± 58.8 |
| $AUC_\infty$ (hr · kg · ng/mL/mg) | 617 |

[1]Dose normalized by dividing the parameter by the nominal dose of 1.55 mg/kg
Data points used for half-life determination are in bold.

TABLE 9 shows individual and average plasma concentrations (ng/ml) and pharmacokinetic parameters for Compound 1 (free acid) after intravitreal administration in male New Zealand White rabbits at 2.5 mg/eye (~1.54 mg/kg) (Group 5).

TABLE 9

Intravitreal; 40 mM Phosphate Buffer pH 4.0 + 2.5% Dextrose (suspension)

| Time point (hr) | Rabbit # | Conc. (ng/mL) | Average (ng/mL) | SD |
|---|---|---|---|---|
| 1.0 | 33 | 34.6 | 25.3 | 13.15 |
|  | 34 | 16.0 |  |  |
| 3.0 | 35 | 28.4 | 24.4 | 5.66 |
|  | 36 | 20.4 |  |  |
| 6.0 | 37 | 22.0 | 23.1 | 1.48 |
|  | 38 | 24.1 |  |  |
| 24.0 | 39 | 9.96 | 12.3 | 3.35 |
|  | 40 | 14.7 |  |  |
| 48.0 | 33 | 2.69 | 3.63 | 1.33 |
|  | 34 | 4.57 |  |  |
| 72.0 | 35 | 1.83 | 1.65 | 0.26 |
|  | 36 | 1.46 |  |  |

Pharmacokinetic Parameters

| | |
|---|---|
| $C_{max}$ (ng/mL) ± SE | 25.3 ± 9.30 |
| $t_{max}$ (hr) | 1.00 |
| $t_{1/2}$ (hr) | 16.5 |
| $MRT_{last}$ (hr) | 19.1 |
| $AUC_{last}$ (hr · ng/mL) ± SE | 707 ± 53.1 |
| $AUC_\infty$ (hr · ng/mL) | 746 |

Dose Normalized Values[1]

| | |
|---|---|
| $AUC_{last}$ (hr · kg · ng/mL/mg) | 459 ± 34.5 |
| $AUC_\infty$ (hr · kg · ng/mL/mg) | 484 |

[1]Dose normalized by dividing the parameter by the nominal dose of 1.54 mg/kg
Data points used for half-life determination are in bold.

TABLE 10 shows average plasma pharmacokinetic parameters for Compound 1 following topical ocular, subcutaneous, and intravitreal administration in male New Zealand White rabbits.

TABLE 10

| | PK parameters | | | | |
|---|---|---|---|---|---|
| | Topical ocular | Subcutaneous | | Intravitreal | |
| | Group | | | | |
| | 1 | 2 | 3 | 4 | 5 |
| | Salt form | | | | |
| | Compound 1 sodium salt | Compound 1 sodium salt | Compound 1 free acid | Compound 1 sodium salt | Compound 1 free acid |
| | Vehicle | | | | |
| | 15% HPβCD + 1% Dextrose in water | 15% HPβCD + 1% Dextrose in water | 40 mM Phosphate Buffer pH 4.0 + 2.5% Dextrose in water | 10% HPβCD + 2% Dextrose in water | 40 mM Phosphate Buffer pH 4.0 + 2.5% Dextrose |
| | Formulation | | | | |
| | Solution | Solution | Suspension | Solution | Suspension |
| | Dose (mg/kg/dose) | | | | |
| | 0.70 | 5 | 5 | 1.55 | 1.54 |
| $C_{max}$ (ng/mL) | 7.48 | 1525 | 395 | 39.8 | 25.3 |
| $t_{max}$ (hr) | 4.00 | 0.25 | 0.25 | 3.00 | 1.00 |
| $t_{1/2}$ (hr) | ND | 0.47 | 2.12 | 8.08 | 16.5 |
| $MRT_{last}$ (hr) | 2.98 | 0.87 | 1.58 | 15.1 | 19.1 |
| $AUC_{last}$ (hr · ng/mL) | 11.8 | 1555 | 864 | 953 | 707 |
| $AUC_\infty$ (hr · ng/mL) | ND | 1560 | 1198 | 956 | 746 |
| $AUC_{last}$ (hr · kg · ng/mL/mg)[1] | 16.8 | 311 | 173 | 615 | 459 |
| $AUC_\infty$ (hr · kg · ng/mL/mg)[1] | ND | 312 | 240 | 617 | 484 |

[1]Dose normalized by dividing the parameter by the nominal dose in mg/kg
ND: Not Determined TABLE 11 shows individual and average aqueous humor concentrations (ng/g) following topical ocular (Group 1), subcutaneous (Groups 2 and 3), and intravitreal (Groups 4 and 5) administration in male New Zealand White rabbits.

TABLE 11

| Group # | Time (hr) | Animal ID | Conc. (ng/mL) OD | Conc. (ng/mL) OS | Average Conc.[1] (ng/g) | SD (ng/g) |
|---|---|---|---|---|---|---|
| Group 1 | 0.5 | 1 | 3.44 | 1.78 | 45.8 | 79.6 |
| | | 2 | 12.8 | *165* | | |
| | 1.0 | 3 | 4.03 | 3.55 | 15.0 | 22.8 |
| | | 4 | 3.05 | *49.2* | | |
| | 2.0 | 5 | 2.46 | 14.5 | 31.6 | 41.7 |
| | | 6 | *93.5* | 15.8 | | |
| | 4.0 | 7 | 5.48 | 5.61 | 8.24 | 4.04 |
| | | 8 | 7.78 | 14.1 | | |
| Group 2 | 0.5 | 9 | 23.5 | 24.6 | 26.1 | 8.58 |
| | | 10 | 18.0 | 38.2 | | |
| | 1.0 | 11 | 4.51 | 1.84 | 3.30 | 1.11 |
| | | 12 | 3.22 | 3.63 | | |
| | 2.0 | 13 | 0.581 | 0.498 | 0.72 | 0.42 |
| | | 14 | 0.453 | *1.34* | | |
| | 4.0 | 15 | BLOQ | BLOQ | ND | ND |
| | | 16 | BLOQ | BLOQ | | |
| Group 3 | 0.5 | 17 | BLOQ | BLOQ | 1.21 | ND |
| | | 18 | 0.519 | 1.90 | | |
| | 1.0 | 19 | 0.485 | 0.684 | 0.41 | 0.21 |
| | | 20 | 0.229 | 0.257 | | |
| | 2.0 | 21 | 0.601 | BLOQ | 0.66 | 0.10 |
| | | 22 | *0.770* | 0.594 | | |
| | 4.0 | 23 | 0.209 | 0.229 | 0.51 | 0.50 |
| | | 24 | BLOQ | *1.08* | | |

TABLE 11-continued

| Group # | Time (hr) | Animal ID | Conc. (ng/mL) OD | Conc. (ng/mL) OS | Average Conc.[1] (ng/g) | SD (ng/g) |
|---|---|---|---|---|---|---|
| Group 4 | 6.0 | 29 | 90600 | 77100 | 80575 | 6881 |
| | | 30 | 75300 | 79300 | | |
| | 24 | 31 | 4700 | 5190 | 9000 | 6926 |
| | | 32 | *19300* | 6810 | | |
| | 48 | 25 | 2040 | 1510 | 1963 | 340 |
| | | 26 | 2330 | 1970 | | |
| | 72 | 27 | 23.2 | 16.1 | 34.5 | 17.4 |
| | | 28 | 49.7 | 49.0 | | |
| Group 5 | 6.0 | 37 | 34200 | 15700 | 26400 | 8547 |
| | | 38 | 23400 | 32300 | | |
| | 24 | 39 | 3890 | 6480 | 4270 | 2327 |
| | | 40 | 5540 | 1170 | | |
| | 48 | 33 | 476 | 632 | 915 | 424 |
| | | 34 | 1220 | 1330 | | |
| | 72 | 35 | 145 | 172 | 120 | 46.5 |
| | | 36 | 94.1 | 70.2 | | |

[1]Aqueous humor sample density of 1 g/mL is assumed
BLOQ: Below the limit of quantitation (0.2 ng/mL)
ND: Not Determined
Bold and italicized values are outliers based on Grubb's outlier test TABLE 12 shows individual and average vitreous humor concentrations (ng/g) following topical ocular (Group 1), subcutaneous (Groups 2 and 3), and intravitreal (Groups 4 and 5) administration in male New Zealand White rabbits.

TABLE 13 shows individual and average iris, retina, choroid, and cornea tissue concentrations (ng/g) for Compound 1 (sodium salt) after topical ocular administration in male New Zealand White rabbits at 1.2 mg/eye (~0.7 mg/kg/dose) (Group 1).

TABLE 14 shows individual and average iris, retina, choroid, and cornea tissue concentrations (ng/g) for Compound 1 (sodium salt) after subcutaneous administration in male New Zealand White rabbits at 5 mg/kg/dose (Group 2).

TABLE 15 shows individual and average iris, retina, choroid, and cornea tissue concentrations (ng/g) for Compound 1 (free acid) after subcutaneous administration in male New Zealand White rabbits at 5 mg/kg/dose (Group 3).

TABLE 16 shows individual and average iris, retina, choroid, and cornea tissue concentrations (ng/g) for Compound 1 (free acid) after subcutaneous administration in male New Zealand White rabbits at 5 mg/kg/dose (Group 3).

TABLE 17 shows individual and average iris, retina, choroid, and cornea tissue concentrations (ng/g) for Compound 1 (sodium salt) after intravitreal administration in male New Zealand White rabbits at 2.5 mg/eye (~1.55 mg/kg) (Group 4).

TABLE 18 shows individual and average iris, retina, choroid, and cornea tissue concentrations (ng/g) for Compound 1 (free acid) after intravitreal administration in male New Zealand White rabbits at 2.5 mg/eye (~1.54 mg/kg) (group 5).

TABLE 19 shows average ocular tissue peak concentrations for Compound 1 following topical ocular, subcutaneous and intravitreal administration in male New Zealand White rabbits.

TABLE 12

| Group # | Time (hr) | Animal ID | Conc. (ng/mL) OD | Conc. (ng/mL) OS | Average Conc[1]. (ng/g) | SD (ng/g) |
|---|---|---|---|---|---|---|
| Group 1 | 0.5 | 1 | *0.873* | 0.528 | 0.61 | 0.17 |
|  |  | 2 | 0.549 | 0.507 |  |  |
|  | 1.0 | 3 | 1.97 | 0.282 | 2.09 | 1.32 |
|  |  | 4 | 3.28 | 2.83 |  |  |
|  | 2.0 | 5 | 1.14 | *10.1* | 3.33 | 4.51 |
|  |  | 6 | 1.14 | 0.950 |  |  |
|  | 4.0 | 7 | 1.09 | 2.20 | 4.01 | 5.50 |
|  |  | 8 | 0.551 | *12.2* |  |  |
| Group 2 | 0.5 | 9 | 0.77 | 1.03 | 0.83 | 0.23 |
|  |  | 10 | 0.537 | 0.981 |  |  |
|  | 1.0 | 11 | 0.252 | 0.766 | 0.45 | 0.23 |
|  |  | 12 | 0.442 | 0.337 |  |  |
|  | 2.0 | 13 | BLOQ | BLOQ | ND | ND |
|  |  | 14 | BLOQ | BLOQ |  |  |
|  | 4.0 | 15 | BLOQ | BLOQ | ND | ND |
|  |  | 16 | BLOQ | BLOQ |  |  |
| Group 3 | 0.5 | 17 | BLOQ | 0.227 | 0.40 | 0.27 |
|  |  | 18 | 0.261 | *0.708* |  |  |
|  | 1.0 | 19 | 0.407 | BLOQ | 0.41 | ND |
|  |  | 20 | BLOQ | BLOQ |  |  |
|  | 2.0 | 21 | BLOQ | BLOQ | ND | ND |
|  |  | 22 | BLOQ | BLOQ |  |  |
|  | 4.0 | 23 | BLOQ | 0.408 | 0.41 | ND |
|  |  | 24 | BLOQ | BLOQ |  |  |
| Group 4 | 6.0 | 29 | 1450000 | 592000 | 988500 | 554214 |
|  |  | 30 | 1480000 | 432000 |  |  |
|  | 24 | 31 | 438000 | 295000 | 349500 | 85994 |
|  |  | 32 | 406000 | 259000 |  |  |
|  | 48 | 25 | 85200 | 82300 | 82000 | 9796 |
|  |  | 26 | 68600 | 91900 |  |  |
|  | 72 | 27 | 14500 | 13500 | 13450 | 1237 |
|  |  | 28 | 11700 | 14100 |  |  |
| Group 5 | 6.0 | 37 | 592000 | 625000 | 479750 | 163272 |
|  |  | 38 | 432000 | 270000 |  |  |
|  | 24 | 39 | 296000 | 528000 | 408750 | 117721 |
|  |  | 40 | 491000 | 320000 |  |  |
|  | 48 | 33 | 75900 | 148000 | 97800 | 35923 |
|  |  | 34 | 68300 | 99000 |  |  |
|  | 72 | 35 | 96500 | 101000 | 65350 | 40696 |
|  |  | 36 | 16200 | 47700 |  |  |

[1]Vitreous humor sample density of 1 g/mL is assumed
BLOQ: Below the limit of quantitation (0.2 ng/mL)
ND: Not Determined;
bold and italicized values are outliers based on Grubb's outlier test

TABLE 13

| Tissue | Time (hr) | Animal ID | Conc. (ng/mL) OD | Conc. (ng/mL) OS | Tissue Weight (g) OD | Tissue Weight (g) OS | Homogenate Vol. (mL) OD | Homogenate Vol. (mL) OS | Conc.[1] (ng/g) OD | Conc.[1] (ng/g) OS | Average (ng/g) | SD (ng/g) |
|---|---|---|---|---|---|---|---|---|---|---|---|---|
| Iris | 0.5 | 1 | 2.55 | 1.62 | 0.025 | 0.024 | 0.28 | 0.26 | 28.1 | 17.8 | 24.3 | 7.16 |
|  |  | 2 | 1.7 | 2.95 | 0.024 | 0.032 | 0.26 | 0.35 | 18.7 | 32.5 |  |  |
|  | 1 | 3 | 1.57 | 2.70 | 0.024 | 0.016 | 0.26 | 0.17 | 17.3 | 29.7 | 55.2 | 41.9 |
|  |  | 4 | 5.69 | 10.1 | 0.025 | 0.033 | 0.27 | 0.36 | 62.6 | 111 |  |  |
|  | 2 | 5 | 1.12 | 2.99 | 0.022 | 0.024 | 0.24 | 0.27 | 12.3 | 32.9 | 51.9 | 39.2 |
|  |  | 6 | 5.40 | 9.38 | 0.034 | 0.032 | 0.38 | 0.35 | 59.4 | 103 |  |  |
|  | 4 | 7 | 2.97 | 2.79 | 0.020 | 0.027 | 0.22 | 0.30 | 32.7 | 30.7 | 261 | 462 |
|  |  | 8 | 2.54 | 86.7 | 0.031 | 0.024 | 0.34 | 0.27 | 27.9 | *954* |  |  |
| Retina | 0.5 | 1 | 0.695 | 3.06 | 0.053 | 0.031 | 0.59 | 0.34 | 7.65 | 33.7 | 25.6 | 12.2 |
|  |  | 2 | 2.54 | 3.01 | 0.029 | 0.051 | 0.32 | 0.56 | 27.9 | 33.1 |  |  |
|  | 1 | 3 | 6.99 | 2.01 | 0.035 | 0.042 | 0.39 | 0.47 | 76.9 | 22.1 | 59.2 | 28.6 |
|  |  | 4 | 7.81 | 4.70 | 0.034 | 0.063 | 0.37 | 0.69 | 85.9 | 51.7 |  |  |
|  | 2 | 5 | 1.56 | 8.93 | 0.044 | 0.037 | 0.48 | 0.40 | 17.2 | 98.2 | 48.3 | 36.0 |
|  |  | 6 | 4.54 | 2.54 | 0.069 | 0.047 | 0.76 | 0.52 | 49.9 | 27.9 |  |  |
|  | 4 | 7 | 1.60 | 5.89 | 0.046 | 0.059 | 0.50 | 0.65 | 17.6 | 64.8 | 405 | 684 |
|  |  | 8 | 9.88 | 130 | 0.054 | 0.045 | 0.59 | 0.49 | 109 | *1430* |  |  |
| Choroid | 0.5 | 1 | 2.75 | 1.47 | 0.034 | 0.044 | 0.37 | 0.48 | 30.3 | 16.2 | 57.7 | 47.5 |
|  |  | 2 | 5.55 | 11.2 | 0.051 | 0.043 | 0.57 | 0.47 | 61.1 | 123 |  |  |
|  | 1 | 3 | 5.56 | 1.50 | 0.050 | 0.047 | 0.55 | 0.52 | 61.2 | 16.5 | 32.2 | 20.4 |
|  |  | 4 | 2.89 | 1.77 | 0.037 | 0.067 | 0.40 | 0.74 | 31.8 | 19.5 |  |  |
|  | 2 | 5 | 1.19 | 3.99 | 0.050 | 0.060 | 0.55 | 0.66 | 13.1 | 43.9 | 59.2 | 43.0 |
|  |  | 6 | 10.5 | 5.86 | 0.054 | 0.027 | 0.59 | 0.30 | 116 | 64.5 |  |  |
|  | 4 | 7 | 2.53 | 7.37 | 0.039 | 0.034 | 0.43 | 0.38 | 27.8 | 81.1 | 165 | 224 |
|  |  | 8 | 4.74 | 45.4 | 0.036 | 0.035 | 0.39 | 0.38 | 52.1 | *499* |  |  |
| Cornea | 0.5 | 1 | 21.8 | 38.8 | 0.079 | 0.073 | 0.87 | 0.81 | 240 | 427 | 1015 | 1342 |
|  |  | 2 | 33.6 | 275 | 0.066 | 0.068 | 0.73 | 0.75 | 370 | *3025* |  |  |
|  | 1 | 3 | 87.2 | 43.8 | 0.068 | 0.076 | 0.74 | 0.83 | 959 | 482 | 548 | 307 |
|  |  | 4 | 19.9 | 48.4 | 0.065 | 0.067 | 0.72 | 0.73 | 219 | 532 |  |  |
|  | 2 | 5 | 20.9 | 25.4 | 0.070 | 0.073 | 0.77 | 0.81 | 230 | 279 | 1073 | 1210 |
|  |  | 6 | 87.8 | 256 | 0.068 | 0.073 | 0.75 | 0.81 | 966 | 2816 |  |  |
|  | 4 | 7 | 44.8 | 37.0 | 0.084 | 0.081 | 0.93 | 0.90 | 493 | 407 | 534 | 233 |
|  |  | 8 | 32.9 | 79.4 | 0.075 | 0.074 | 0.83 | 0.82 | 362 | 873 |  |  |

[1] Tissue sample density 1 g/mL is assumed;
BLOQ: Below the limit of quantitation (0.5 ng/mL);
ND: Not Determined;
bold and italicized values are outliers based on Grubb's outlier test.

TABLE 14

| Tissue | Time (hr) | Animal ID | Conc. (ng/mL) OD | Conc. (ng/mL) OS | Tissue Weight (g) OD | Tissue Weight (g) OS | Homogenate Vol. (mL) OD | Homogenate Vol. (mL) OS | Conc.[1] (ng/g) OD | Conc.[1] (ng/g) OS | Average (ng/g) | SD (ng/g) |
|---|---|---|---|---|---|---|---|---|---|---|---|---|
| Iris | 0.5 | 9 | 27.7 | 29.2 | 0.020 | 0.028 | 0.22 | 0.31 | 305 | 321 | 459 | 209 |
|  |  | 10 | 41.3 | 68.8 | 0.029 | 0.026 | 0.32 | 0.29 | 454 | 757 |  |  |
|  | 1 | 11 | 11.4 | 8.87 | 0.020 | 0.022 | 0.21 | 0.24 | 125 | 97.6 | 94.7 | 28.5 |
|  |  | 12 | 9.02 | 5.13 | 0.026 | 0.036 | 0.28 | 0.40 | 99.2 | 56.4 |  |  |
|  | 2 | 13 | 4.76 | 3.07 | 0.018 | 0.022 | 0.19 | 0.25 | 52.4 | 33.8 | 29.7 | 17.4 |
|  |  | 14 | 1.79 | 1.18 | 0.019 | 0.023 | 0.21 | 0.26 | 19.7 | 13.0 |  |  |
|  | 4 | 15 | 2.12 | BLOQ | 0.020 | 0.021 | 0.22 | 0.23 | *23.3* | ND | 30.4 | 6.13 |
|  |  | 16 | 3.07 | 3.10 | 0.017 | 0.030 | 0.18 | 0.33 | 33.8 | 34.1 |  |  |
| Retina | 0.5 | 9 | 2.77 | 4.36 | 0.038 | 0.040 | 0.41 | 0.44 | 30.5 | 48.0 | 40.5 | 9.23 |
|  |  | 10 | 3.17 | 4.43 | 0.049 | 0.059 | 0.54 | 0.65 | 34.9 | 48.7 |  |  |
|  | 1 | 11 | 2.04 | 3.93 | 0.043 | 0.064 | 0.48 | 0.70 | 22.4 | 43.2 | 32.6 | 14.3 |
|  |  | 12 | 1.66 | 4.22 | 0.040 | 0.059 | 0.44 | 0.65 | 18.3 | 46.4 |  |  |
|  | 2 | 13 | 1.36 | 1.62 | 0.046 | 0.062 | 0.50 | 0.68 | 15.0 | 17.8 | 16.4 | ND |
|  |  | 14 | BLOQ | BLOQ | 0.048 | 0.077 | 0.53 | 0.85 | ND | ND |  |  |
|  | 4 | 15 | BLOQ | BLOQ | 0.061 | 0.059 | 0.67 | 0.65 | ND | ND | 19.7 | ND |
|  |  | 16 | 1.79 | BLOQ | 0.037 | 0.049 | 0.41 | 0.54 | 19.7 | ND |  |  |
| Choroid | 0.5 | 9 | 24.0 | 25.6 | 0.030 | 0.037 | 0.33 | 0.40 | 264 | 282 | 266 | 21.8 |
|  |  | 10 | 25.6 | 21.4 | 0.027 | 0.029 | 0.30 | 0.31 | 282 | 235 |  |  |
|  | 1 | 11 | 29.1 | 13.1 | 0.047 | 0.057 | 0.51 | 0.63 | 320 | 144 | 200 | 88 |
|  |  | 12 | 19.2 | 11.4 | 0.034 | 0.066 | 0.38 | 0.72 | 211 | 125 |  |  |
|  | 2 | 13 | 13.5 | 7.03 | 0.039 | 0.040 | 0.43 | 0.44 | 149 | 77.3 | 68.8 | 58.7 |
|  |  | 14 | 2.32 | 2.15 | 0.022 | 0.047 | 0.24 | 0.52 | 25.5 | 23.7 |  |  |
|  | 4 | 15 | 1.70 | 1.22 | 0.040 | 0.037 | 0.44 | 0.41 | 18.7 | 13.4 | 15.5 | 2.58 |
|  |  | 16 | 1.50 | 1.22 | 0.048 | 0.040 | 0.53 | 0.44 | 16.5 | 13.4 |  |  |
| Cornea | 0.5 | 9 | 0.883 | 2.46 | 0.062 | 0.065 | 0.68 | 0.71 | 9.71 | 27.1 | 19.4 | 7.22 |
|  |  | 10 | 1.77 | 1.94 | 0.068 | 0.063 | 0.75 | 0.69 | 19.5 | 21.3 |  |  |
|  | 1 | 11 | 2.37 | 4.52 | 0.063 | 0.065 | 0.69 | 0.72 | 26.1 | *49.7* | 31.1 | 12.4 |
|  |  | 12 | 2.13 | 2.30 | 0.074 | 0.073 | 0.81 | 0.80 | 23.4 | 25.3 |  |  |

TABLE 14-continued

| Tissue | Time (hr) | Animal ID | Conc. (ng/mL) OD | Conc. (ng/mL) OS | Tissue Weight (g) OD | Tissue Weight (g) OS | Homogenate Vol. (mL) OD | Homogenate Vol. (mL) OS | Conc.[1] (ng/g) OD | Conc.[1] (ng/g) OS | Average (ng/g) | SD (ng/g) |
|---|---|---|---|---|---|---|---|---|---|---|---|---|
| | 2 | 13 | 1.06 | 0.998 | 0.063 | 0.073 | 0.69 | 0.80 | 11.7 | 11.0 | 9.45 | 3.26 |
| | | 14 | 0.518 | BLOQ | 0.070 | 0.064 | 0.77 | 0.70 | *5.70* | ND | | |
| | 4 | 15 | 0.752 | 0.784 | 0.064 | 0.064 | 0.70 | 0.71 | 8.27 | 8.62 | 10.1 | 2.58 |
| | | 16 | 0.873 | 1.26 | 0.070 | 0.074 | 0.77 | 0.81 | 9.60 | 13.9 | | |

[1]Tissue sample density of 1 g/mL is assumed
BLOQ: Below the limit of quantitation (0.5 ng/mL)
ND: Not Determined;
bold and italicized values are outliers based on Grubb's outlier test

TABLE 15

| Tissue | Time (hr) | Animal ID | Conc. (ng/mL) OD | Conc. (ng/mL) OS | Tissue Weight (g) OD | Tissue Weight (g) OS | Homogenate Vol. (mL) OD | Homogenate Vol. (mL) OS | Conc.[1] (ng/g) OD | Conc.[1] (ng/g) OS | Average (ng/g) | SD (ng/g) |
|---|---|---|---|---|---|---|---|---|---|---|---|---|
| Iris | 0.5 | 17 | 7.1 | 4.27 | 0.032 | 0.017 | 0.36 | 0.19 | 78.1 | 47.0 | 50.3 | 19.0 |
| | | 18 | 3.39 | 3.54 | 0.041 | 0.024 | 0.45 | 0.26 | 37.3 | 38.9 | | |
| | 1 | 19 | 4.35 | 4.33 | 0.045 | 0.020 | 0.49 | 0.22 | 47.9 | 47.6 | 58.0 | 30.1 |
| | | 20 | 9.29 | 3.12 | 0.034 | 0.018 | 0.38 | 0.19 | 102 | 34.3 | | |
| | 2 | 21 | 2.77 | 2.68 | 0.033 | 0.017 | 0.37 | 0.19 | 30.5 | 29.5 | 27.6 | 6.23 |
| | | 22 | 2.91 | 1.67 | 0.044 | 0.023 | 0.48 | 0.25 | 32.0 | *18.4* | | |
| | 4 | 23 | 2.41 | 1.54 | 0.015 | 0.077 | 0.17 | 0.85 | 26.5 | 16.9 | 17.5 | 7.27 |
| | | 24 | 1.63 | 0.794 | 0.028 | 0.041 | 0.30 | 0.46 | 17.9 | 8.73 | | |
| Retina | 0.5 | 17 | 6.72 | 3.33 | 0.030 | 0.053 | 0.33 | 0.58 | 73.9 | 36.6 | 38.7 | 25.6 |
| | | 18 | 2.87 | 1.16 | 0.030 | 0.074 | 0.33 | 0.81 | 31.6 | 12.8 | | |
| | 1 | 19 | 0.942 | 0.63 | 0.035 | 0.071 | 0.38 | 0.79 | 10.4 | 6.93 | 10.2 | 3.19 |
| | | 20 | BLOQ | 1.21 | 0.042 | 0.047 | 0.47 | 0.52 | ND | 13.3 | | |
| | 2 | 21 | 0.574 | 0.63 | 0.050 | 0.046 | 0.56 | 0.51 | 6.31 | 6.93 | 10.5 | 6.73 |
| | | 22 | BLOQ | 1.66 | 0.028 | 0.043 | 0.30 | 0.47 | ND | *18.3* | | |
| | 4 | 23 | BLOQ | 1.18 | 0.043 | 0.044 | 0.47 | 0.48 | ND | 13.0 | 35.3 | ND |
| | | 24 | BLOQ | 5.24 | 0.046 | 0.072 | 0.51 | 0.80 | ND | 57.6 | | |
| Choroid | 0.5 | 17 | 7.83 | 7.55 | 0.020 | 0.029 | 0.22 | 0.32 | 86.1 | 83.1 | 127 | 50.2 |
| | | 18 | 16.7 | 14.0 | 0.024 | 0.054 | 0.27 | 0.59 | 184 | 154 | | |
| | 1 | 19 | 6.04 | 8.01 | 0.036 | 0.042 | 0.40 | 0.46 | 66.4 | 88.1 | 83.3 | 12.2 |
| | | 20 | 8.65 | 7.60 | 0.033 | 0.036 | 0.37 | 0.40 | 95.2 | 83.6 | | |
| | 2 | 21 | 3.32 | 4.84 | 0.036 | 0.034 | 0.39 | 0.37 | 36.5 | 53.2 | 47.7 | 8.17 |
| | | 22 | 4.26 | 4.94 | 0.046 | 0.031 | 0.50 | 0.34 | 46.9 | 54.3 | | |
| | 4 | 23 | 4.82 | 2.12 | 0.030 | 0.023 | 0.33 | 0.25 | 53.0 | 23.3 | 61.0 | 39.5 |
| | | 24 | 4.65 | 10.6 | 0.034 | 0.078 | 0.37 | 0.85 | 51.2 | 117 | | |
| Cornea | 0.5 | 17 | BLOQ | BLOQ | 0.064 | 0.063 | 0.70 | 0.70 | ND | ND | 7.96 | ND |
| | | 18 | 0.55 | 0.897 | 0.077 | 0.066 | 0.84 | 0.72 | 6.05 | 9.87 | | |
| | 1 | 19 | BLOQ | BLOQ | 0.065 | 0.058 | 0.72 | 0.64 | ND | ND | 12.2 | ND |
| | | 20 | 1.11 | BLOQ | 0.065 | 0.067 | 0.72 | 0.74 | 12.2 | ND | | |
| | 2 | 21 | 0.514 | BLOQ | 0.073 | 0.066 | 0.80 | 0.73 | 5.65 | ND | 5.65 | ND |
| | | 22 | BLOQ | BLOQ | 0.076 | 0.065 | 0.84 | 0.72 | ND | ND | | |
| | 4 | 23 | 0.942 | BLOQ | 0.066 | 0.011 | 0.72 | 0.12 | 10.4 | ND | 15.8 | 10.3 |
| | | 24 | 0.847 | 2.51 | 0.068 | 0.062 | 0.75 | 0.68 | 9.32 | *27.6* | | |

[1]Tissue sample density of 1 g/mL is assumed
BLOQ: Below the limit of quantitation (0.5 ng/mL)
ND: Not Determined;
bold and italicized values are outliers based on Grubb's outlier test

TABLE 16

| Tissue | Time (hr) | Animal ID | Conc. (ng/mL) OD | Conc. (ng/mL) OS | Tissue Weight (g) OD | Tissue Weight (g) OS | Homogenate Vol. (mL) OD | Homogenate Vol. (mL) OS | Conc.[1] (ng/g) OD | Conc.[1] (ng/g) OS | Average (ng/g) | SD (ng/g) |
|---|---|---|---|---|---|---|---|---|---|---|---|---|
| Iris | 0.5 | 17 | 7.1 | 4.27 | 0.032 | 0.017 | 0.36 | 0.19 | 78.1 | 47.0 | 50.3 | 19.0 |
| | | 18 | 3.39 | 3.54 | 0.041 | 0.024 | 0.45 | 0.26 | 37.3 | 38.9 | | |
| | 1 | 19 | 4.35 | 4.33 | 0.045 | 0.020 | 0.49 | 0.22 | 47.9 | 47.6 | 58.0 | 30.1 |
| | | 20 | 9.29 | 3.12 | 0.034 | 0.018 | 0.38 | 0.19 | 102 | 34.3 | | |
| | 2 | 21 | 2.77 | 2.68 | 0.033 | 0.017 | 0.37 | 0.19 | 30.5 | 29.5 | 27.6 | 6.23 |
| | | 22 | 2.91 | 1.67 | 0.044 | 0.023 | 0.48 | 0.25 | 32.0 | *18.4* | | |
| | 4 | 23 | 2.41 | 1.54 | 0.015 | 0.077 | 0.17 | 0.85 | 26.5 | 16.9 | 17.5 | 7.27 |
| | | 24 | 1.63 | 0.794 | 0.028 | 0.041 | 0.30 | 0.46 | 17.9 | 8.73 | | |
| Retina | 0.5 | 17 | 6.72 | 3.33 | 0.030 | 0.053 | 0.33 | 0.58 | 73.9 | 36.6 | 38.7 | 25.6 |
| | | 18 | 2.87 | 1.16 | 0.030 | 0.074 | 0.33 | 0.81 | 31.6 | 12.8 | | |

TABLE 16-continued

| Tissue | Time (hr) | Animal ID | Conc. (ng/mL) OD | Conc. (ng/mL) OS | Tissue Weight (g) OD | Tissue Weight (g) OS | Homogenate Vol. (mL) OD | Homogenate Vol. (mL) OS | Conc.[1] (ng/g) OD | Conc.[1] (ng/g) OS | Average (ng/g) | SD (ng/g) |
|---|---|---|---|---|---|---|---|---|---|---|---|---|
|  | 1 | 19 | 0.942 | 0.63 | 0.035 | 0.071 | 0.38 | 0.79 | 10.4 | 6.93 | 10.2 | 3.19 |
|  |  | 20 | BLOQ | 1.21 | 0.042 | 0.047 | 0.47 | 0.52 | ND | 13.3 |  |  |
|  | 2 | 21 | 0.574 | 0.63 | 0.050 | 0.046 | 0.56 | 0.51 | 6.31 | 6.93 | 10.5 | 6.73 |
|  |  | 22 | BLOQ | 1.66 | 0.028 | 0.043 | 0.30 | 0.47 | ND | *18.3* |  |  |
|  | 4 | 23 | BLOQ | 1.18 | 0.043 | 0.044 | 0.47 | 0.48 | ND | 13.0 | 35.3 | ND |
|  |  | 24 | BLOQ | 5.24 | 0.046 | 0.072 | 0.51 | 0.80 | ND | 57.6 |  |  |
| Choroid | 0.5 | 17 | 7.83 | 7.55 | 0.020 | 0.029 | 0.22 | 0.32 | 86.1 | 83.1 | 127 | 50.2 |
|  |  | 18 | 16.7 | 14.0 | 0.024 | 0.054 | 0.27 | 0.59 | 184 | 154 |  |  |
|  | 1 | 19 | 6.04 | 8.01 | 0.036 | 0.042 | 0.40 | 0.46 | 66.4 | 88.1 | 83.3 | 12.2 |
|  |  | 20 | 8.65 | 7.60 | 0.033 | 0.036 | 0.37 | 0.40 | 95.2 | 83.6 |  |  |
|  | 2 | 21 | 3.32 | 4.84 | 0.036 | 0.034 | 0.39 | 0.37 | 36.5 | 53.2 | 47.7 | 8.17 |
|  |  | 22 | 4.26 | 4.94 | 0.046 | 0.031 | 0.50 | 0.34 | 46.9 | 54.3 |  |  |
|  | 4 | 23 | 4.82 | 2.12 | 0.030 | 0.023 | 0.33 | 0.25 | 53.0 | 23.3 | 61.0 | 39.5 |
|  |  | 24 | 4.65 | 10.6 | 0.034 | 0.078 | 0.37 | 0.85 | 51.2 | 117 |  |  |
| Cornea | 0.5 | 17 | BLOQ | BLOQ | 0.064 | 0.063 | 0.70 | 0.70 | ND | ND | 7.96 | ND |
|  |  | 18 | 0.55 | 0.897 | 0.077 | 0.066 | 0.84 | 0.72 | 6.05 | 9.87 |  |  |
|  | 1 | 19 | BLOQ | BLOQ | 0.065 | 0.058 | 0.72 | 0.64 | ND | ND | 12.2 | ND |
|  |  | 20 | 1.11 | BLOQ | 0.065 | 0.067 | 0.72 | 0.74 | 12.2 | ND |  |  |
|  | 2 | 21 | 0.514 | BLOQ | 0.073 | 0.066 | 0.80 | 0.73 | 5.65 | ND | 5.65 | ND |
|  |  | 22 | BLOQ | BLOQ | 0.076 | 0.065 | 0.84 | 0.72 | ND | ND |  |  |
|  | 4 | 23 | 0.942 | BLOQ | 0.066 | 0.011 | 0.72 | 0.12 | 10.4 | ND | 15.8 | 10.3 |
|  |  | 24 | 0.847 | 2.51 | 0.068 | 0.062 | 0.75 | 0.68 | 9.32 | *27.6* |  |  |

[1] Tissue sample density of 1 g/mL is assumed
BLOQ: Below the limit of quantitation (0.5 ng/mL)
ND: Not Determined;
bold and italicized values are outliers based on Grubb's outlier test

TABLE 17

| Tissue | Time (hr) | Animal ID | Conc. (ng/mL) OD | Conc. (ng/mL) OS | Tissue Weight (g) OD | Tissue Weight (g) OS | Homogenate Vol. (mL) OD | Homogenate Vol. (mL) OS | Conc.[1] (ng/g) OD | Conc.[1] (ng/g) OS | Avg. (ng/g) | SD (ng/g) |
|---|---|---|---|---|---|---|---|---|---|---|---|---|
| Iris | 6.0 | 29 | 35500 | 34000 | 0.027 | 0.017 | 0.29 | 0.19 | 390500 | 374000 | 351725 | 38024 |
|  |  | 30 | 27800 | 30600 | 0.023 | 0.022 | 0.25 | 0.24 | 305800 | 336600 |  |  |
|  | 24 | 31 | 6890 | 7610 | 0.044 | 0.047 | 0.48 | 0.52 | 75790 | 83710 | 141350 | 97709 |
|  |  | 32 | 11000 | 25900 | 0.030 | 0.035 | 0.33 | 0.39 | 121000 | 284900 |  |  |
|  | 48 | 25 | 2380 | 1960 | 0.025 | 0.035 | 0.27 | 0.39 | 26180 | 21560 | 24585 | 4778 |
|  |  | 26 | 1820 | 2780 | 0.027 | 0.028 | 0.30 | 0.31 | 20020 | 30580 |  |  |
|  | 72 | 27 | 169 | 225 | 0.027 | 0.024 | 0.30 | 0.26 | 1859 | 2475 | 1550 | 789 |
|  |  | 28 | 110 | 59.5 | 0.025 | 0.025 | 0.28 | 0.27 | 1210 | 655 |  |  |
| Retina | 6.0 | 29 | 39200 | 41100 | 0.043 | 0.053 | 0.47 | 0.58 | 431200 | 452100 | 774400 | 418169 |
|  |  | 30 | 119000 | 82300 | 0.042 | 0.040 | 0.46 | 0.44 | 1309000 | 905300 |  |  |
|  | 24 | 31 | 29200 | 28000 | 0.052 | 0.041 | 0.57 | 0.45 | 321200 | 308000 | 355850 | 48612 |
|  |  | 32 | 35200 | 3700 | 0.059 | 0.078 | 0.65 | 0.86 | 387200 | 407000 |  |  |
|  | 48 | 25 | 6490 | 6030 | 0.058 | 0.048 | 0.63 | 0.53 | 71390 | 66330 | 72628 | 6090 |
|  |  | 26 | 7360 | 6530 | 0.055 | 0.081 | 0.60 | 0.89 | 80960 | 71830 |  |  |
|  | 72 | 27 | 750 | 370 | 0.048 | 0.046 | 0.52 | 0.50 | 8250 | 4070 | 6056 | 1786 |
|  |  | 28 | 598 | 484 | 0.042 | 0.053 | 0.46 | 0.58 | 6578 | 5324 |  |  |
| Choroid | 6.0 | 29 | 164000 | 105000 | 0.031 | 0.031 | 0.34 | 0.34 | 1804000 | 1155000 | 947375 | 671486 |
|  |  | 30 | 31500 | 44000 | 0.035 | 0.049 | 0.38 | 0.54 | 346500 | 484000 |  |  |
|  | 24 | 31 | 11800 | 9890 | 0.034 | 0.030 | 0.37 | 0.33 | 129800 | 108790 | 138848 | 43289 |
|  |  | 32 | 18400 | 10400 | 0.032 | 0.027 | 0.36 | 0.30 | 202400 | 114400 |  |  |
|  | 48 | 25 | 3480 | 3740 | 0.038 | 0.037 | 0.41 | 0.41 | 38280 | 41140 | 38638 | 5866 |
|  |  | 26 | 4040 | 2790 | 0.059 | 0.054 | 0.65 | 0.59 | 44440 | 30690 |  |  |
|  | 72 | 27 | 107 | 282 | 0.028 | 0.050 | 0.31 | 0.55 | 1177 | 3102 | 2723 | 1039 |
|  |  | 28 | 311 | 290 | 0.028 | 0.040 | 0.30 | 0.44 | 3421 | 3190 |  |  |
| Cornea | 6.0 | 29 | 6300 | 6940 | 0.062 | 0.060 | 0.68 | 0.66 | 69300 | 76340 | 71445 | 4484 |
|  |  | 30 | 6710 | 6030 | 0.078 | 0.080 | 0.86 | 0.88 | 73810 | 66330 |  |  |
|  | 24 | 31 | 2180 | 1560 | 0.073 | 0.082 | 0.80 | 0.90 | 23980 | 17160 | 23678 | 6419 |
|  |  | 32 | 2940 | 1930 | 0.075 | 0.083 | 0.82 | 0.91 | 32340 | 21230 |  |  |
|  | 48 | 25 | 1050 | 662 | 0.071 | 0.070 | 0.78 | 0.77 | 11550 | 7282 | 7527 | 2801 |
|  |  | 26 | 538 | 487 | 0.072 | 0.076 | 0.79 | 0.83 | 5918 | 5357 |  |  |
|  | 72 | 27 | 18.0 | 20.1 | 0.068 | 0.065 | 0.75 | 0.71 | 198 | 221 | 421 | 244 |
|  |  | 28 | 56.9 | 58.1 | 0.066 | 0.070 | 0.72 | 0.77 | 626 | 639 |  |  |

[1] Tissue sample density of 1 g/mL is assumed
BLOQ: Below the limit of quantitation (0.5 ng/mL)
ND: Not Determined;
bold and italicized values are outliers based on Grubb's outlier test

TABLE 18

| Tissue | Time (hr) | Animal ID | Conc. (ng/mL) OD | Conc. (ng/mL) OS | Tissue Weight (g) OD | Tissue Weight (g) OS | Homogenate Vol. (mL) OD | Homogenate Vol. (mL) OS | Conc.[1] (ng/g) OD | Conc.[1] (ng/g) OS | Avg. (ng/g) | SD (ng/g) |
|---|---|---|---|---|---|---|---|---|---|---|---|---|
| Iris | 6.0 | 37 | 18500 | 13800 | 0.028 | 0.027 | 0.30 | 0.29 | 203500 | 151800 | 210650 | 99417 |
|  |  | 38 | 32100 | 12200 | 0.024 | 0.029 | 0.27 | 0.32 | 353100 | 134200 |  |  |
|  | 24 | 39 | 7670 | 14100 | 0.028 | 0.032 | 0.30 | 0.36 | 84370 | 155100 | 112668 | 32535 |
|  |  | 40 | 11000 | 8200 | 0.033 | 0.031 | 0.36 | 0.34 | 121000 | 90200 |  |  |
|  | 48 | 33 | 1010 | 1950 | 0.035 | 0.029 | 0.39 | 0.32 | 11110 | 21450 | 16775 | 5934 |
|  |  | 34 | 1110 | 2030 | 0.023 | 0.029 | 0.25 | 0.32 | 12210 | 22330 |  |  |
|  | 72 | 35 | 279 | 1800 | 0.031 | 0.038 | 0.34 | 0.42 | 3069 | 19800 | 10313 | 8202 |
|  |  | 36 | 351 | 1320 | 0.033 | 0.031 | 0.36 | 0.34 | 3861 | 14520 |  |  |
| Retina | 6.0 | 37 | 146000 | 154000 | 0.060 | 0.041 | 0.66 | 0.45 | 1606000 | 1694000 | 1988250 | 910606 |
|  |  | 38 | 303000 | 120000 | 0.107 | 0.045 | 1.18 | 0.50 | *3333000* | 1320000 |  |  |
|  | 24 | 39 | 130000 | 98900 | 0.068 | 0.063 | 0.75 | 0.70 | 1430000 | 1087900 | 1572725 | 455441 |
|  |  | 40 | 145000 | 198000 | 0.077 | 0.078 | 0.84 | 0.85 | 1595000 | 2178000 |  |  |
|  | 48 | 33 | 66700 | 14000 | 0.053 | 0.045 | 0.58 | 0.50 | 733700 | 154000 | 679800 | 394530 |
|  |  | 34 | 65500 | 101000 | 0.068 | 0.068 | 0.74 | 0.74 | 720500 | 1111000 |  |  |
|  | 72 | 35 | 9890 | 10800 | 0.047 | 0.048 | 0.52 | 0.52 | 108790 | 118800 | 109065 | 31421 |
|  |  | 36 | 6070 | 12900 | 0.056 | 0.055 | 0.62 | 0.61 | 66770 | 141900 |  |  |
| Choroid | 6.0 | 37 | 32800 | 63400 | 0.061 | 0.042 | 0.67 | 0.46 | 360800 | 697400 | 663575 | 208925 |
|  |  | 38 | 75400 | 69700 | 0.096 | 0.066 | 1.05 | 0.73 | 829400 | 766700 |  |  |
|  | 24 | 39 | 15200 | 28400 | 0.017 | 0.032 | 0.19 | 0.35 | 167200 | 312400 | 397650 | 201714 |
|  |  | 40 | 57500 | 43500 | 0.042 | 0.044 | 0.46 | 0.48 | 632500 | 478500 |  |  |
|  | 48 | 33 | 9940 | 9320 | 0.047 | 0.044 | 0.51 | 0.48 | 109340 | 102520 | 120010 | 28663 |
|  |  | 34 | 9580 | 14800 | 0.042 | 0.031 | 0.46 | 0.34 | 105380 | *162800* |  |  |
|  | 72 | 35 | 2180 | 2660 | 0.039 | 0.035 | 0.43 | 0.39 | 23980 | 29260 | 27555 | 3751 |
|  |  | 36 | 2270 | 2910 | 0.041 | 0.036 | 0.45 | 0.40 | 24970 | 32010 |  |  |
| Cornea | 6.0 | 37 | 7910 | 3140 | 0.063 | 0.063 | 0.69 | 0.69 | 87010 | 34540 | 54560 | 36663 |
|  |  | 38 | 7610 | 1180 | 0.055 | 0.053 | 0.60 | 0.58 | 83710 | 12980 |  |  |
|  | 24 | 39 | 1520 | 1190 | 0.069 | 0.075 | 0.76 | 0.83 | 16720 | 13090 | 17270 | 7296 |
|  |  | 40 | 2520 | 1050 | 0.085 | 0.081 | 0.93 | 0.89 | 27720 | 11550 |  |  |
|  | 48 | 33 | 437 | 293 | 0.072 | 0.077 | 0.80 | 0.85 | 4807 | 3223 | 4634 | 1278 |
|  |  | 34 | 384 | 571 | 0.073 | 0.073 | 0.80 | 0.80 | 4224 | 6281 |  |  |
|  | 72 | 35 | 37.7 | 117 | 0.085 | 0.076 | 0.93 | 0.83 | 415 | 1287 | 762 | 397 |
|  |  | 36 | 77.2 | 45.3 | 0.069 | 0.067 | 0.76 | 0.74 | 849 | 498 |  |  |

[1]Tissue sample density of 1 g/mL is assumed
BLOQ: Below the limit of quantitation (0.5 ng/mL)
ND: Not Determined;
bold and italicized values are outliers based on Grubb's outlier test.

TABLE 19

| | Dose Route | | | | |
|---|---|---|---|---|---|
| | Topical ocular | Subcutaneous | | Intravitreal | |
| | Group | | | | |
| | 1 | 2 | 3 | 4 | 5 |
| | Salt form | | | | |
| | Compound 1 sodium salt | Compound 1 sodium salt | Compound 1 free acid | Compound 1 sodium salt | Compound 1 free acid |
| | Vehicle | | | | |
| | 15% HPβCD + 1% Dextrose in water | 15% HPβCD + 1% Dextrose in water | 40 mM Phosphate Buffer pH 4.0 + 2.5% Dextrose in water | 10% HPβCD + 2% Dextrose in water | 40 mM Phosphate Buffer pH 4.0 + 2.5% Dextrose |
| | Formulation | | | | |
| | Solution | Solution | Suspension | Solution | Suspension |
| | Dose (mg/kg/dose) | | | | |
| | 0.70 | 5 | 5 | 1.55 | 1.54 |
| Tissue | Average Peak Concentration (ng/g) | | | | |
| Aqueous Humor | 45.8 | 26.1 | 1.21 | 80575 | 26400 |
| Vitreous Humor | 0.61 | 0.83 | 0.40 | 988500 | 479750 |
| Iris | 24.3 | 459 | 50.3 | 351725 | 210650 |

TABLE 19-continued

| | | Dose Route | | |
|---|---|---|---|---|
| Topical ocular | Subcutaneous | | Intravitreal | |
| | | Group | | |
| 1 | 2 | 3 | 4 | 5 |
| | | Salt form | | |
| Compound 1 sodium salt | Compound 1 sodium salt | Compound 1 free acid | Compound 1 sodium salt | Compound 1 free acid |
| | | Vehicle | | |
| 15% HPβCD + 1% Dextrose in water | 15% HPβCD + 1% Dextrose in water | 40 mM Phosphate Buffer pH 4.0 + 2.5% Dextrose in water | 10% HPβCD + 2% Dextrose in water | 40 mM Phosphate Buffer pH 4.0 + 2.5% Dextrose |
| | | Formulation | | |
| Solution | Solution | Suspension | Solution | Suspension |
| | | Dose (mg/kg/dose) | | |
| 0.70 | 5 | 5 | 1.55 | 1.54 |

| Tissue | Average Peak Concentration (ng/g) | | | | |
|---|---|---|---|---|---|
| Retina | 25.6 | 40.5 | 38.7 | 774400 | 1988250 |
| Choroid | 57.7 | 266 | 127 | 947375 | 663575 |
| Cornea | 1015 | 19.4 | 7.96 | 71445 | 54560 |

Example 3. Tolerability and Effect on Intraocular Pressure of Compound 1 (Sodium Salt) Following Repeated Topical and Subcutaneous Administration To measure the tolerability and effect of Compound 1 (sodium salt) on intraocular pressure following repeated topical and subcutaneous administration, normotensive New Zealand White rabbits were treated with Compound 1 (sodium salt).

Prior to treatment initiation, selection of animals for the study was based on a visual appraisal of good clinical condition and body weight specifications. All animals were healthy at the time of animal selection. Animals selected for use in this study were as uniform in age and weight as possible. The animals were housed in individual cages within the same room during the study. No other species were housed in the same room. The room was well ventilated (greater than 10 air changes per hour) with at least 60% fresh air. A 12-hour light/12-hour dark photoperiod was maintained, except when rooms were illuminated during the dark cycle to accommodate necessary study procedures. Animals had ad libitum access to species specific chow. Chlorinated, municipal tap water was made available ad libitum to each animal via water bottles. All study animals were acclimated to their designated housing for 16 days prior to study start. All animals were weighed prior to the start of the procedures and ranged from 2.88 to 3.44 kilograms at study start.

Vehicle 1 (15% HPβCD, 1% Dextrose) was prepared by introducing 15 g of HPβCD into a glass container, adding 80 mL of deionized water to the container, and mixing the contents by vortex until the HPβCD powder was fully dissolved. 2 mL of 50% dextrose solution was then added to the container, the volume was brought to 100 mL with deionized water to create a 15% HPβCD and 1% dextrose solution, and the contents were mixed by vortex. The resulting solution was sterile filtered through a 0.2 μm filter into 14 separate sterile bottles of sufficient volume for daily vehicle control dosing and preparation of Compound 1 dosing solutions, and stored refrigerated at 2-8° C.

A first batch of Vehicle 2 (15% HPβCD, 2% Dextrose) was prepared by introducing 1.5 g of HPβCD into a glass container, adding 8 mL of deionized water to the container, and mixing by vortex the contents until the HPβCD powder was fully dissolved. 0.4 mL of 50% dextrose solution was then added to the container, the volume was brought up to 10 mL with deionized water to create a 15% HPβCD and 2% dextrose solution, and the contents were mixed by vortex. The resulting solution was sterile filtered through a 0.2 μm filter into a sterile bottle and stored refrigerated at 2-8° C.

A second batch of Vehicle 2 (15% HPβCD, 2% Dextrose), was prepared by introducing 0.75 g of HPβCD into a glass container, adding 4 mL of deionized water to the container, and mixing by vortex the contents until the HPβCD powder was fully dissolved. 0.2 mL of 50% dextrose solution was then added to the container, the volume was brought to 5 mL with deionized water to create a 15% HPβCD and 2% dextrose solution, and the contents were mixed by vortex. The resulting solution was sterile filtered through a 0.2 μm filter into a sterile bottle and stored refrigerated at 2-8° C. Compound 1 (sodium salt) dosing solutions were prepared fresh once daily for each day of dosing.

A 15 mg/mL Compound 1 (sodium salt) solution was prepared by introducing Compound 1 (sodium salt) into glass containers, adding Vehicle 2 at a volume to create a 15 mg/mL Compound 1 (sodium salt) solution, and mixing by vortex and/or sonicating the contents until the Compound 1 (sodium salt) powder was fully dissolved and a clear solution was formed. The pH was confirmed to be between 6.5-7 using pH indicator strips. The solution was then sterile filtered through a 0.2 μm filter into a sterile bottle and stored refrigerated at 2-8° C.

A 40 mg/mL Compound 1 (sodium salt) solution was prepared by introducing Compound 1 (sodium salt) into glass containers pre-calibrated to ~95% of the final formulation volume, then adding Vehicle 1 to reach ~90% of the final formulation volume, and mixing by vortex and/or sonicating the contents until the Compound 1 (sodium salt) powder was fully dissolved and a clear solution was formed. The volume was brought to the calibration mark and then to the final formulation volume with additional Vehicle 1 to create a 40 mg/mL Compound 1 (sodium salt) solution. If necessary, the solution was further sonicated. The pH was confirmed to be between 7-7.5 using pH indicator strips. The solution was sterile filtered through a 0.2 μm filter into a sterile bottle and stored refrigerated at 2-8° C.

All dosing solutions were allowed to come to room temperature before dosing. A 0.2 mL aliquot of each formulation was collected prior to dosing each day, snap frozen on dry ice, and stored frozen at −60 to −80° C. for potential future analysis.

Prior to placement on study, each animal underwent an ophthalmic examination (slitlamp biomicroscopy and indirect ophthalmoscopy). Ocular findings were scored according to a modified McDonald-Shadduck Scoring System and recorded on a standardized data sheet. The acceptance criteria for placement on study were scores of "0" for all variables.

Animals were acclimated 1 to 2 times per day to the intraocular pressure (IOP) measurement procedures prior to initiation of the study to determine baseline IOP levels. IOP acclimation was performed in the two weeks prior to study start for a total of 5 days. Animals with unacceptable IOP values were excluded from the study. Prior to taking all IOP measurements, 1 to 2 drops of a 0.5% proparacaine solution were applied to the eye as a topical anesthetic. OP measurements were performed with a pneumotonometer.

Test and control formulations were administered to the animals once or twice daily topically into both eyes or subcutaneously starting on Day 1 according to TABLE 20 and TABLE 21 below. PM dosing, where applicable, was performed ~8 hours after AM dosing.

TABLE 20

| Group | Treatment | Dose | Vehicle | Dose route | Compound 1 (sodium salt) concentration |
|---|---|---|---|---|---|
| 1 | Vehicle 1 | N/A | 15% HPβCD, 1% Dextrose | Topical BID for 7 days (OU) | N/A |
| 2 | Compound 1 (sodium salt) | 0.45 mg/eye | 15% HPβCD, 2% Dextrose | Topical BID for 7 days (OU) | 15 mg/mL |
| 3 | Compound 1 (sodium salt) | 1.2 mg/eye | 15% HPβCD, 1% Dextrose | Topical BID for 7 days (OU) | 40 mg/mL |
| 4 | Compound 1 (sodium salt) | 1.2 mg/eye | 15% HPβCD, 1% Dextrose | Topical QD for 7 days (OU) | 40 mg/mL |
| 5 | Compound 1 (sodium salt) | 10 mg/kg | 15% HPβCD, 1% Dextrose | SC BID for 7 days | 40 mg/mL |

OU: both eyes
BID: twice daily (BID dose groups received only AM dosing on Day 7)
QD: once daily
HPβCD: Hydroxy Propyl Beta Cyclodextrin

TABLE 21

| Group | N | Dose Volume | Clinical ophthalmic examination time points | Intraocular pressure measurement time points |
|---|---|---|---|---|
| 1 | 5 | 30 μL/eye | Baseline (prior to first dose) and Days 1, 4, and 8 | Acclimation, baseline (prior to first dose) |
| 2 | 5 | 30 μL/eye | | |
| 3 | 5 | 30 μL/eye | | |
| 4 | 5 | 30 μL/eye | | AM/PM, Day 1 |
| 5 | 5 | 0.25 mL/kg | | AM/PM, Day 2 |
| | | | | AM, Day 3 |
| | | | | AM, Day 4 |
| | | | | AM, Day 5 |
| | | | | AM, Day 6 |
| | | | | AM, Day 7 |
| | | | | AM/PM, Day 8 |

Animals were observed within their cages once daily throughout the study period. Each animal was observed for changes in general appearance and behavior, and was weighed prior to the study initiation. General health observations were recorded daily beginning on Day 1 and continuing throughout the course of the study.

Ophthalmic examination (slit-lamp biomicroscopy only) was performed at baseline (prior to the start of dosing) and on Days 1, 4, and 8. Ocular findings were scored according to a modified McDonald-Shadduck Scoring System. A slit lamp was used to observe conjunctival discharge, conjunctival congestion, conjunctival congestion, the cornea, the surface area of cornea involvement, pannus, pupillary response, aqueous flare, cellular flare, iris involvement, and the lens. An indirect ophthalmoscope was used to observe the vitreous, vitreal hemorrhage, retinal detachment, retinal hemorrhage, and choroidal/retinal inflammation. Animals were prepared for observation by using a solution (atropine, tropicamide, or phenylephrine) to dilate the pupils.

Conjunctival discharge was defined as a whitish gray precipitate from the eye. Scoring was as follows.
 0=Normal, no discharge.
 1=Discharge above normal and present on the inner portion of the eye but not on the lids or hairs of the eyelids.
 2=Discharge is abundant, easily observed and has collected on the lids and hairs of the eyelids.
 3=Discharge has been flowing over the eyelids so as to wet the hairs substantially on the skin around the eye.

Conjunctival congestion causes the blood vessels of the eye to become enlarged. Scoring was as follows.
 0=Normal, may appear blanched to reddish pink without perilimbal injection (except at the 12:00 and 6:00 positions) with vessels of the palpebral and bulbar conjunctiva easily observed.

1=A flushed, reddish color predominantly confined to the palpebral; conjunctiva with some perilimbal injection but primarily confined to the lower and upper parts of the eye from the 4:00 to the 7:00 and 11:00 to 1:00 positions.

2=Bright red color of the palpebral conjunctiva with accompanying perilimbal injection covering at least 75% of the circumference of the perilimbal region.

3=Dark, beefy red color with congestion of both the bulbar and palpebral conjunctiva along with pronounced perilimbal injection and the presence of petechial on the conjunctiva. The petechial generally predominates along the nictitating membrane and upper palpebral conjunctiva.

Conjunctival swelling, defined as swelling of the conjunctiva, was scored as follows.

0=Normal or no swelling of the conjunctival tissue.

1=Swelling above normal without eversion of the eyelids (easily discerned by noting upper and lower eyelids are positioned as in the normal eye); swelling generally starts in the lower cul-de-sac near the inner canthus.

2=Swelling with misalignment of the normal approximation of the lower and upper eyelids; primarily confined to the upper eyelid so that in the initial stages, the misapproximation of the eyelids begins by partial eversion of the upper eyelid. In this state the swelling is confined generally to the upper eyelid with some swelling in the lower cul-de-sac.

3=Swelling definite with partial eversion of the upper and lower eyelids essentially equivalent. This can be easily observed by looking at the animal head-on and noting the position of the eyelids; if the eye margins do not meet, eversion has occurred.

4=Eversion of the upper eyelid is pronounced with less pronounced eversion of the lower eyelid. It is difficult to retract the lids and observe the perilimbal region.

Iris involvement was observed by checking the iris for hyperemia of the blood vessels. Scoring was as follows.

0=Normal iris without any hyperemia of the blood vessels.

1=Some loss of transparency. Only the epithelium and/or the anterior half of the stroma are involved. The underlying structures are clearly visible although some cloudiness may be readily apparent.

2=Involvement of the entire thickness of the stroma. With diffuse illumination, the underlying structures are just barely visible (can still observe flare, iris, pupil response, and lens).

3=Involvement of the entire thickness of the stroma. With diffuse illumination, the underlying structures cannot be seen.

The surface area of cornea involvement was observed by checking the eye for cloudiness in the stromal region. Scoring was as follows.

0=Normal.
1=1-25% area of stromal cloudiness.
2=26-50% area of stromal cloudiness.
3=51-75% area of stromal cloudiness.
4=76-100% area of stromal cloudiness.

Pannus was observed by checking for vascularization of the cornea. Scoring was as follows.

0=No pannus (vascularization of the cornea).
1=Vascularization present but vessels have not invaded the entire cornea circumference.
2=Vessels have invaded 2 mm or more around entire corneal surface.

Pupillary response was observed by checking for any blockage or a sluggish response in the pupillary region. Scoring was as follows.

0=Normal pupil response.
1=Sluggish or incomplete pupil response.
2=No pupil response.
3=No pupil response due to pharmacological blockage.

Aqueous flare was observed through the breakdown of the blood-aqueous barrier. Scoring was as follows.

0=None.
1=1+.
2=2+.
3=3+.
4=4+ (fibrin).

Cellular flare was observed through cellular observation in the anterior chamber. Scoring was as follows.

0=None.
1=1+.
2=2+.
3=3+.
4=4+.

The lens was observed for any cataracts. Scoring was as follows.

0=Lens clear.
1=Anterior (cortical/capsular).
2=Nuclear.
3=Posterior.
4=Equatorial.

The vitreous was observed for any abnormalities. Scoring was as follows.

0=Clear vitreous.
1=Few scattered opacities, fundus unimpaired.
2=Moderate scattered opacities.
3=Many opacities, marked blurring of fundus details.
4=Dense opacities, no fundus view.

The vitreous was observed for any hemorrhage. Scoring was as follows.

0=Normal.
1=1-25%.
2=26-50%.
3=51-75%.
4=76-100%.

During a retinal detachment, bleeding from small retinal blood vessels may cloud the interior of the eye, which is normally filled with vitreous fluid. Retinal detachment scoring was as follows.

0=None.
1=Rhegmatogenous (retinal detachment occurs when subretinal fluid accumulates in the potential space between the neurosensory retina and the underlying retinal pigment epithelium).
2=Exudative (occurs due to inflammation, injury, or vascular abnormalities that result in fluid accumulating underneath the retina without the presence of a hole, tear, or break).
3=Tractional (occurs when fibrous or fibrovascular tissue, caused by an injury, inflammation, or neovascularization that pulls the sensory retina from the retinal pigment epithelium).

Retinal hemorrhage was observed through abnormal bleeding of the blood vessels in the retina. Scoring was as follows.

0=Normal.
1=1-25%.
2=26-50%.
3=51-75%.
4=76-100%.

Choroidal/retinal inflammation was observed through inflammation of the retina and/or choroid. Scoring was as follows.

0=None.
1=Mild.
2=Moderate.
3=Severe.

IOP measurements were performed twice (AM and PM) at baseline (prior to the start of dosing), twice (AM and PM) on Days 1 and 7, and once daily (AM) on Days 2-6 and Day 8. Prior to taking all IOP measurements, 1 to 2 drops of a 0.5% proparacaine solution were applied to the eye as a topical anesthetic. IOP measurements were performed with a pneumotonometer. AM IOP measurements were performed 2 hours after AM dosing; the only exceptions were Day 8 AM measurements, which were performed 24 hours after the final dose. PM IOP measurements were performed ~5 hours (baseline and Day 1) or ~4 hours (Day 7) after AM IOP measurements, prior to PM dosing, with at least 15 minutes elapsing between anesthetic application for PM IOP measurements and PM dosing. The final round of slit-lamp examinations was performed on Day 8.

All animals exhibited normal health and activity throughout the study. All animals had no ocular anomalies during the baseline pre-screening examination. On Day 1, mild conjunctival congestion (scores=1) was observed across groups as follows: one animal in Group 1 (third eyelid of the left eye only); all five animals in Group 2 (both eyes (OU) in one animal, left (OS) or right eye (OD) only in the remaining four animals); one animal also exhibited mild conjunctival swelling (OS); two animals in Group 3 (both OS); one animal in Group 4 (OS); three animals in Group 5 (one OS, one OU with only the third eyelid affected in one eye).

On Day 4, mild conjunctival congestion (scores=1) was found in the following groups: two animals in Group 2 (one OU, one OD); two animals in Group 3 (one OU, one OD); one animal in Group 4 (OU, third eyelid only); none in Groups 1 and 5.

No ocular anomalies were observed on Day 8.

Figure 17:
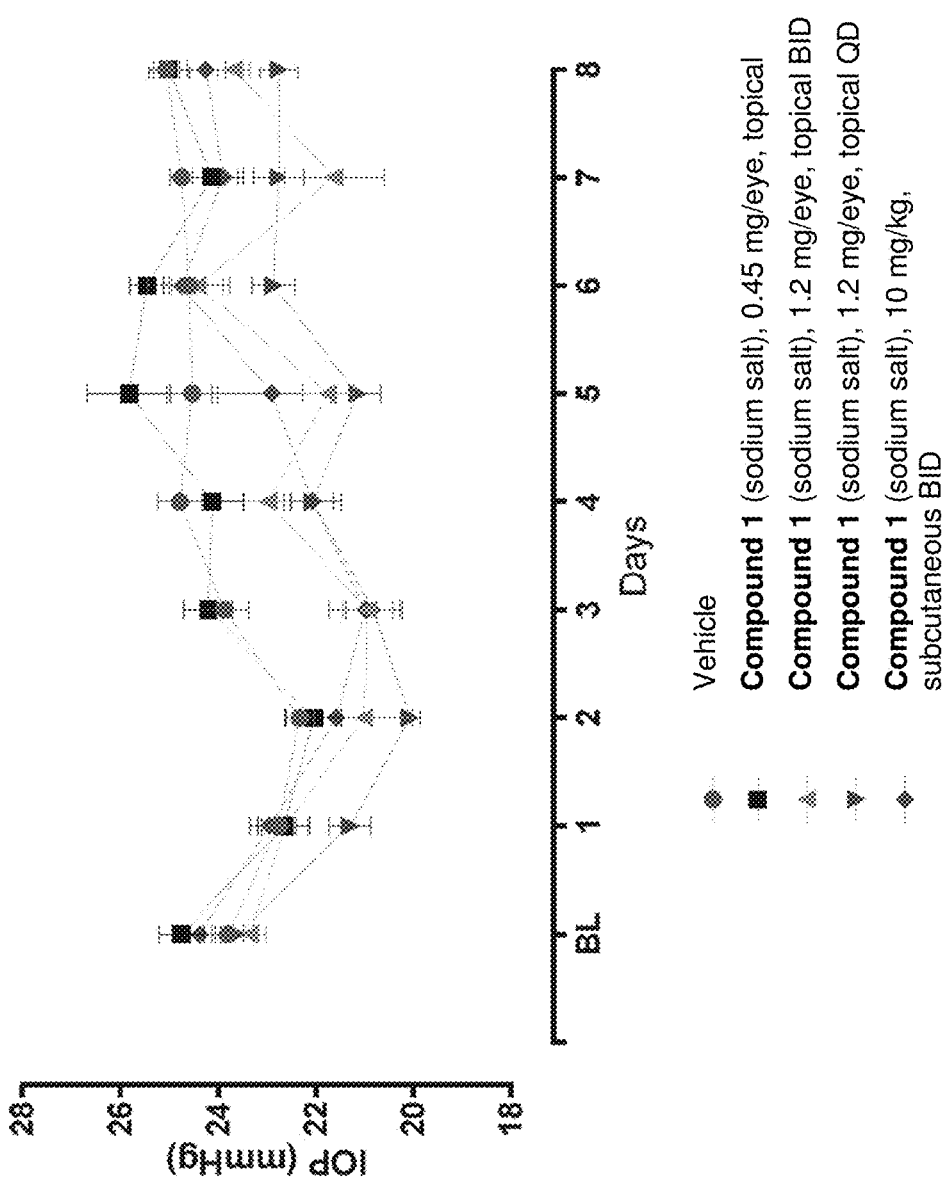
FIG. 17 illustrates the raw data intraocular pressure (IOP) values recorded after AM dosing of Compound 1 in New Zealand White rabbits over 8 days.
Figure 18:
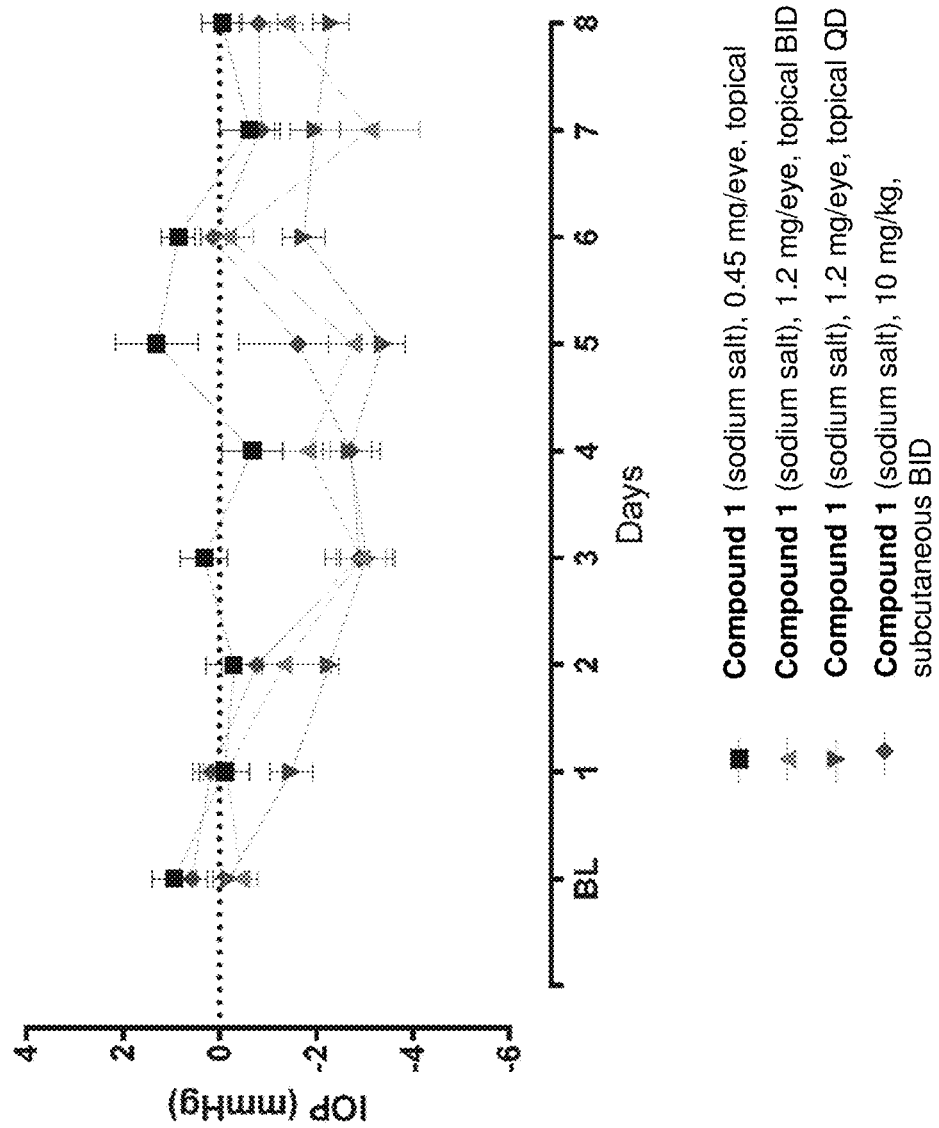
FIG. 18 illustrates intraocular pressure (IOP) differences from a vehicle control group after AM dosing of Compound 1 in New Zealand White rabbits over 8 days.
Figure 19:
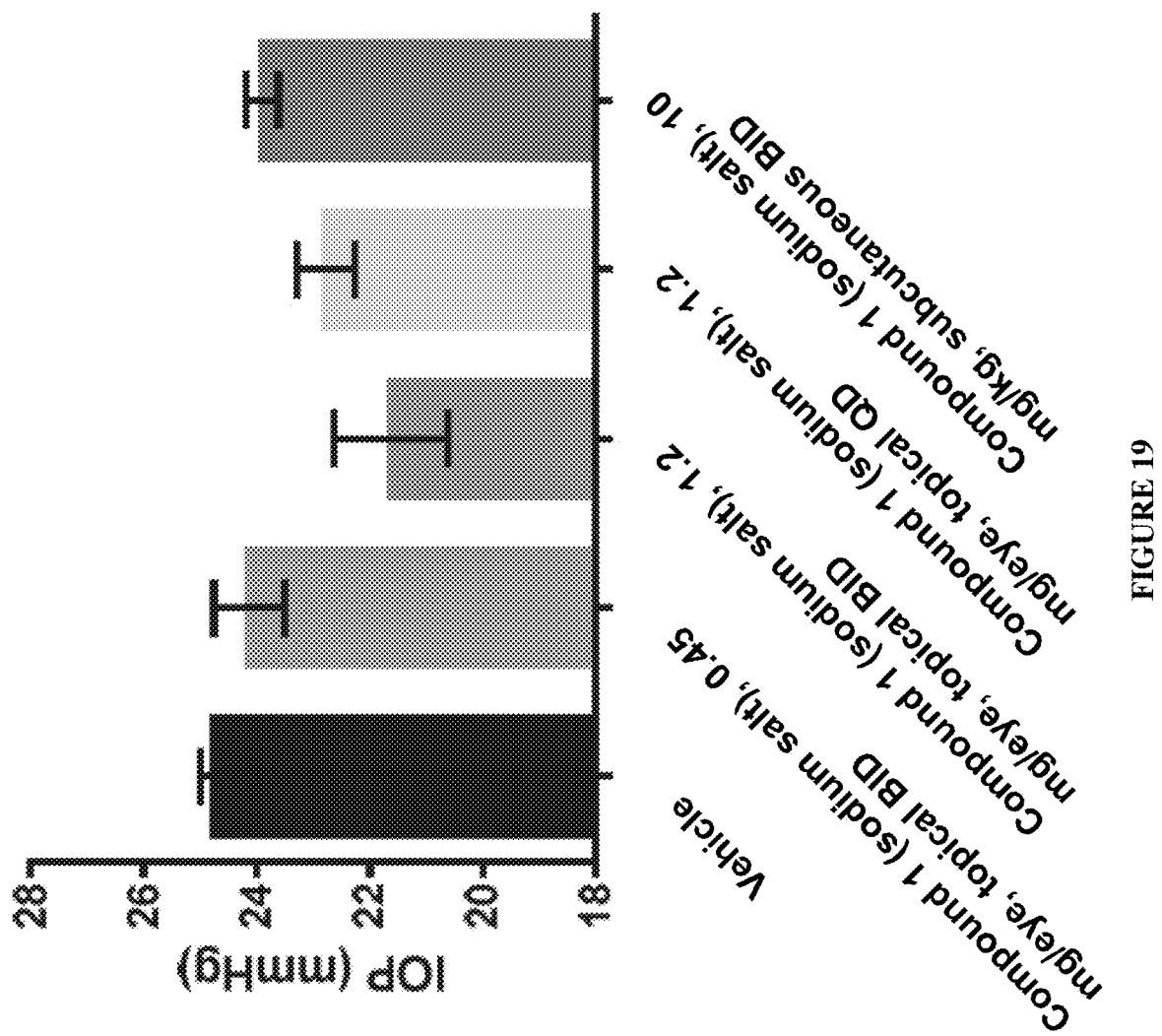
FIG. 19 illustrates the raw data intraocular pressure (IOP) values recorded after AM dosing of Compound 1 in New Zealand White rabbits on Day 7.
Figure 20:
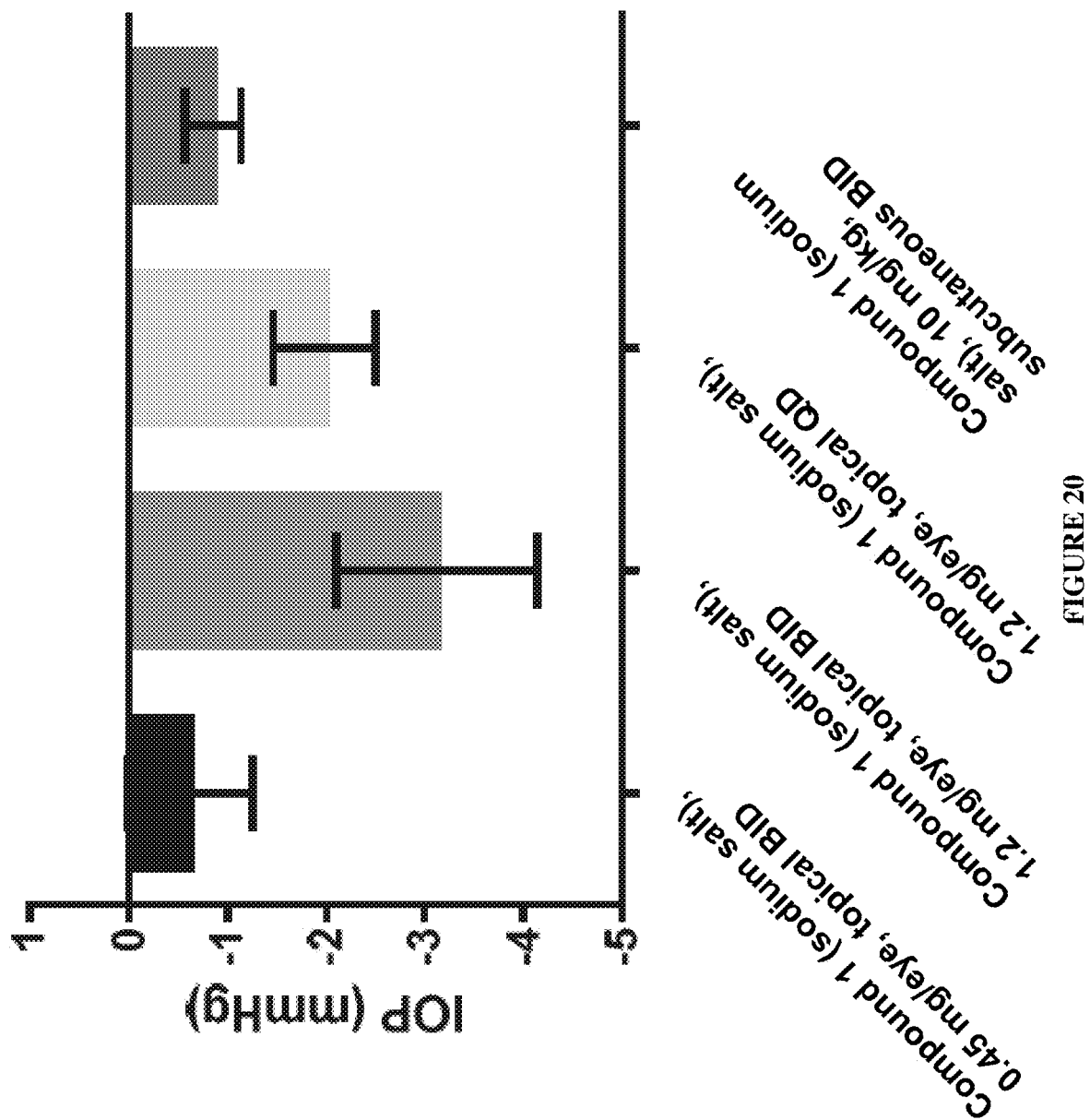
FIG. 20 illustrates intraocular pressure (IOP) differences from a vehicle control group after AM dosing of Compound 1 in New Zealand White rabbits on Day 7.
Figure 21:
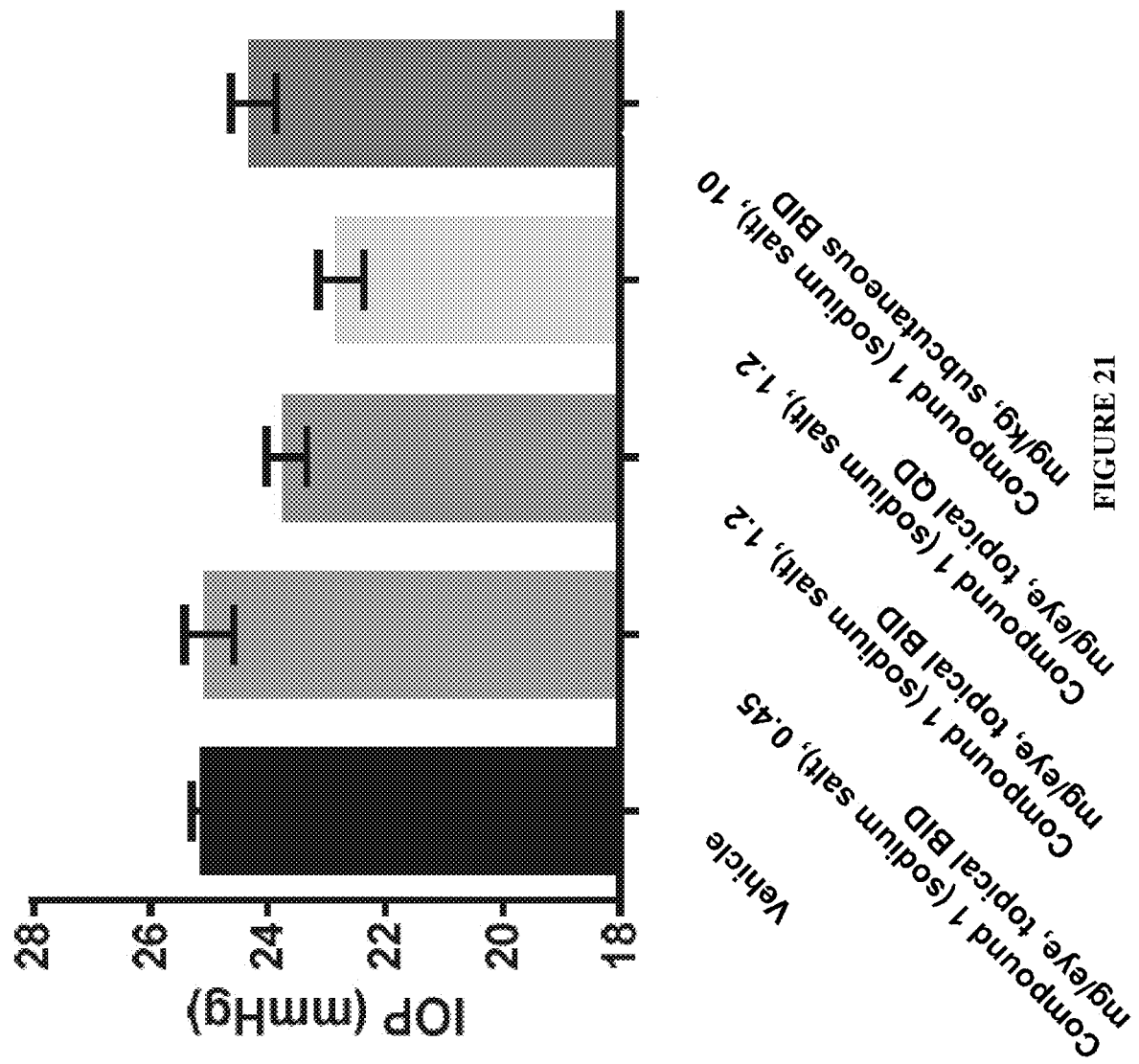
FIG. 21 illustrates the raw data intraocular pressure (IOP) values recorded after AM dosing of Compound 1 in New Zealand White rabbits on Day 8.
Figure 22:
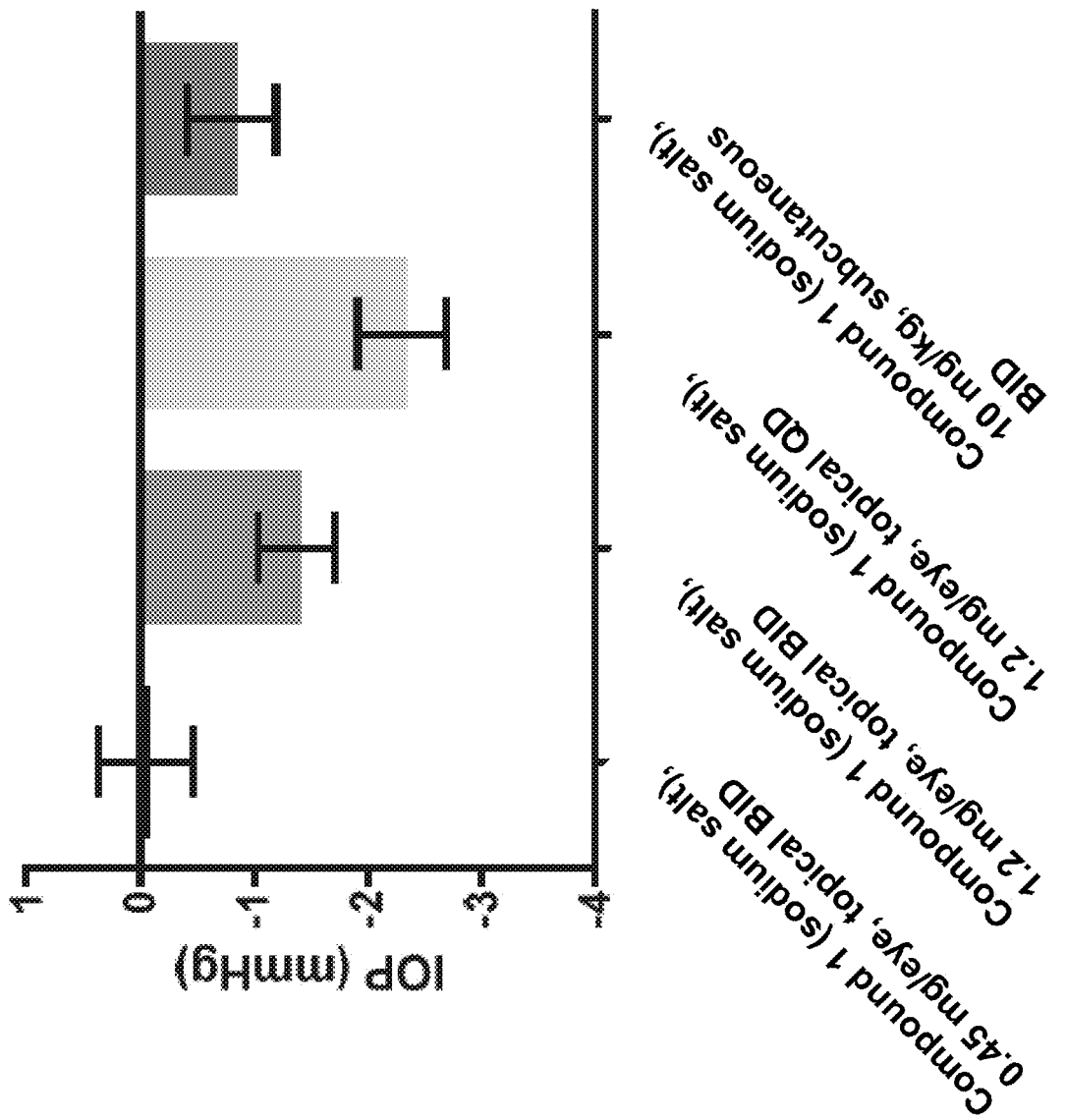
FIG. 22 illustrates intraocular pressure (IOP) differences from a vehicle control group after AM dosing of Compound 1 in New Zealand White rabbits on Day 8.

Over the course of dosing, lower IOP values compared to Group 1 (Vehicle) were found in Groups 3 (1.2 mg/eye topical Compound 1 (sodium salt), BID) and 4 (1.2 mg/eye topical Compound 1 (sodium salt), QD), but not Group 2 (0.45 mg/eye topical Compound 1 (sodium salt), BID). FIG. 17 shows the raw IOP values for vehicle control (Group 1) and the four test Groups 2-5. FIG. 18 shows the differences in IOP from vehicle control, over the course of the 8 days. Group 1 is represented by circles, Group 2 by squares, Group 3 by triangles pointing up, Group 4 by triangles pointing down, and Group 5 by diamonds. Lower IOP values compared to Group 1 were also seen in the early part of the study in Group 5 (10 mg/kg subcutaneous Compound 1 (sodium salt), BID), but the difference decreased towards the end of the study (FIG. 17 and FIG. 18). The apparent reduction in intraocular pressure values in Groups 3 and 4 persisted on Day 7, the last day of dosing as shown in FIG. 19 (raw IOP measurements) and FIG. 20 (decrease in IOP from vehicle control), and Day 8, 24 hours after the end of dosing as shown in FIG. 21 (raw IOP measurements) and FIG. 22 (decrease in IOP from vehicle control)). Intraocular pressure measurements are shown in TABLES 22-25, below.

Topically administered Compound 1 (sodium salt) was observed to reduce intraocular pressure at the 1.2 mg/eye dose, whether dosed QD or BID. Reduction in IOP values was slightly more consistent compared to vehicle control with 10 mg/kg subcutaneous Compound 1 (sodium salt). No adverse effects of the test article on general health were observed during the study. Mild conjunctival congestion observed in some animals appeared to be unrelated to the test article, as the incidence rate was highest in the group receiving the lowest topical dose, and the incidence rate decreased rather than increased with repeated dosing.

TABLE 22

| Group | Animal ID | Acclimation (Day −10, AM) | | Acclimation (Day −10, PM) | | Acclimation (Day −9, AM) | | Acclimation (Day −9, PM) | | Acclimation (Day −8, AM) | | Acclimation (Day −8, PM) | |
|---|---|---|---|---|---|---|---|---|---|---|---|---|---|
| | | OD | OS | OD | OS | OD | OS | OD | OS | OD | OS | OD | OS |
| 1 | A | 19.0 | 21.8 | 23.5 | 23.3 | 22.0 | 22.5 | 24.5 | 23.0 | 23.8 | 24.2 | 24.8 | 26.2 |
| | B | 23.3 | 24.2 | 25.5 | 24.7 | 24.8 | 25.2 | 25.2 | 25.7 | 24.3 | 23.5 | 26.7 | 25.8 |
| | C | 20.0 | 19.8 | 22.2 | 21.5 | 22.8 | 22.5 | 22.8 | 23.2 | 22.0 | 23.3 | 24.5 | 25.0 |
| | D | 23.7 | 24.3 | 24.8 | 24.5 | 24.3 | 24.3 | 25.3 | 25.2 | 23.2 | 24.3 | 26.2 | 27.3 |
| | E | 22.3 | 23.2 | 24.3 | 24.5 | 23.3 | 23.8 | 24.2 | 23.8 | 22.7 | 23.7 | 23.5 | 24.7 |
| | Average | 21.7 | 22.7 | 24.1 | 23.7 | 23.4 | 23.7 | 24.4 | 24.2 | 23.2 | 23.8 | 25.1 | 25.8 |
| | Std Dev | 2.1 | 1.9 | 1.3 | 1.3 | 1.1 | 1.2 | 1.0 | 1.2 | 0.9 | 0.4 | 1.3 | 1.0 |
| 2 | F | 24.0 | 24.3 | 25.2 | 25.0 | 24.3 | 24.8 | 25.0 | 25.0 | 20.8 | 22.0 | 26.2 | 25.3 |
| | G | 21.0 | 22.3 | 24.5 | 24.8 | 24.5 | 24.5 | 25.7 | 25.8 | 24.7 | 24.5 | 26.0 | 26.5 |
| | H | 23.3 | 23.7 | 24.5 | 24.7 | 23.2 | 24.5 | 26.2 | 26.0 | 24.7 | 25.2 | 28.2 | 28.7 |
| | I | 21.5 | 22.3 | 23.2 | 23.0 | 22.5 | 23.3 | 23.8 | 24.3 | 18.7 | 22.0 | 23.7 | 23.5 |
| | J | 22.2 | 24.0 | 25.2 | 25.7 | 24.3 | 24.7 | 27.3 | 28.0 | 24.7 | 25.8 | 27.7 | 27.0 |
| | Average | 22.4 | 23.3 | 24.5 | 24.6 | 23.8 | 24.4 | 25.6 | 25.8 | 22.7 | 23.9 | 26.4 | 26.2 |
| | Std Dev | 1.2 | 1.0 | 0.8 | 1.0 | 0.9 | 0.6 | 1.3 | 1.4 | 2.8 | 1.8 | 1.8 | 1.9 |
| 3 | K | 21.5 | 22.7 | 24.5 | 24.2 | 20.3 | 20.7 | 23.7 | 24.7 | 18.3 | 20.0 | 24.7 | 25.8 |
| | L | 19.3 | 20.8 | 22.8 | 23.0 | 21.8 | 22.3 | 22.8 | 22.3 | 20.2 | 20.3 | 23.2 | 24.0 |
| | M | 20.3 | 21.2 | 23.8 | 24.2 | 23.3 | 24.0 | 25.0 | 24.7 | 23.8 | 23.2 | 24.7 | 25.8 |
| | N | 20.8 | 21.3 | 24.2 | 25.0 | 22.3 | 23.3 | 24.8 | 24.7 | 23.2 | 24.5 | 24.3 | 24.5 |
| | O | 22.2 | 23.3 | 23.5 | 23.8 | 23.8 | 24.0 | 25.2 | 25.0 | 23.5 | 24.0 | 24.3 | 25.2 |
| | Average | 20.8 | 21.9 | 23.8 | 24.0 | 22.3 | 22.9 | 24.3 | 24.3 | 21.8 | 22.4 | 24.2 | 25.1 |
| | Std Dev | 1.1 | 1.1 | 0.7 | 0.7 | 1.4 | 1.4 | 1.0 | 1.1 | 2.4 | 2.1 | 0.6 | 0.8 |
| 4 | P | 22.5 | 23.0 | 25.3 | 23.8 | 23.7 | 21.0 | 24.8 | 24.8 | 22.0 | 22.0 | 23.5 | 24.0 |
| | Q | 21.8 | 21.5 | 24.5 | 23.2 | 24.2 | 23.3 | 25.8 | 24.5 | 24.0 | 23.8 | 27.5 | 27.2 |
| | R | 20.8 | 20.7 | 25.0 | 24.3 | 21.5 | 21.0 | 26.2 | 25.0 | 22.0 | 20.7 | 25.0 | 25.5 |
| | S | 20.8 | 21.2 | 24.0 | 23.3 | 21.7 | 22.8 | 24.3 | 23.5 | 22.0 | 22.5 | 25.3 | 24.3 |
| | T | 19.0 | 20.3 | 24.5 | 25.2 | 20.3 | 23.2 | 24.2 | 25.0 | 21.3 | 24.0 | 24.5 | 25.3 |
| | Average | 21.0 | 21.3 | 24.7 | 24.0 | 22.3 | 22.3 | 25.1 | 24.6 | 22.3 | 22.6 | 25.2 | 25.3 |
| | Std Dev | 1.3 | 1.0 | 0.5 | 0.8 | 1.6 | 1.2 | 0.9 | 0.6 | 1.0 | 1.4 | 1.5 | 1.3 |

TABLE 22-continued

| Group | Animal ID | Acclimation (Day −10, AM) | | Acclimation (Day −10, PM) | | Acclimation (Day −9, AM) | | Acclimation (Day −9, PM) | | Acclimation (Day −8, AM) | | Acclimation (Day −8, PM) | |
|---|---|---|---|---|---|---|---|---|---|---|---|---|---|
| | | OD | OS | OD | OS | OD | OS | OD | OS | OD | OS | OD | OS |
| 5 | U | 22.7 | 22.0 | 24.8 | 24.8 | 23.7 | 24.0 | 25.2 | 25.2 | 23.5 | 23.7 | 26.0 | 25.0 |
| | V | 23.3 | 23.8 | 25.5 | 24.0 | 22.3 | 23.2 | 25.0 | 24.7 | 22.5 | 21.2 | 25.3 | 24.3 |
| | W | 23.2 | 23.2 | 24.7 | 24.5 | 24.0 | 23.7 | 25.3 | 25.2 | 22.7 | 23.7 | 25.2 | 25.8 |
| | X | 23.3 | 23.5 | 25.7 | 24.5 | 24.0 | 24.5 | 24.8 | 25.5 | 23.7 | 24.7 | 25.3 | 25.7 |
| | Y | 21.5 | 21.8 | 23.7 | 23.7 | 20.7 | 20.7 | 23.0 | 23.8 | 20.7 | 21.2 | 24.7 | 25.8 |
| Average | | 22.8 | 22.9 | 24.9 | 24.3 | 22.9 | 23.2 | 24.7 | 24.9 | 22.6 | 22.9 | 25.3 | 25.3 |
| Std Dev | | 0.8 | 0.9 | 0.8 | 0.4 | 1.4 | 1.5 | 0.9 | 0.7 | 1.2 | 1.6 | 0.5 | 0.7 |

OD: Right eye;
OS: left eye

TABLE 23

| Group | Animal ID | Acclimation (Day −7, AM) | | Acclimation (Day −7, PM) | | Acclimation (Day −2, AM) | | Baseline (Day −1, AM) | | Baseline (Day −1, PM) | |
|---|---|---|---|---|---|---|---|---|---|---|---|
| | | OD | OS | OD | OS | OD | OS | OD | OS | OD | OS |
| 1 | A | 24.2 | 25.2 | 22.3 | 24.0 | 24.0 | 24.7 | 21.3 | 22.7 | 22.8 | 24.7 |
| | B | 24.8 | 24.0 | 26.3 | 26.0 | 24.7 | 24.7 | 24.2 | 24.5 | 25.7 | 24.8 |
| | C | 18.8 | 18.7 | 24.8 | 24.7 | 23.3 | 23.7 | 24.5 | 24.2 | 24.2 | 23.5 |
| | D | 22.7 | 23.0 | 25.0 | 25.2 | 24.3 | 25.0 | 23.8 | 24.2 | 24.5 | 26.3 |
| | E | 23.3 | 23.7 | 24.7 | 24.5 | 23.0 | 23.7 | 24.7 | 24.0 | 24.7 | 25.5 |
| Average | | 22.8 | 22.9 | 24.6 | 24.9 | 23.9 | 24.3 | 23.7 | 23.9 | 24.4 | 25.0 |
| Std Dev | | 2.3 | 2.5 | 1.4 | 0.8 | 0.7 | 0.6 | 1.4 | 0.7 | 1.0 | 1.1 |
| 2 | F | 23.2 | 23.5 | 25.5 | 24.8 | 24.2 | 24.5 | 26.2 | 23.2 | 25.7 | 26.2 |
| | G | 24.8 | 25.2 | 26.3 | 24.7 | 25.0 | 25.0 | 24.3 | 24.8 | 24.8 | 25.3 |
| | H | 25.8 | 26.0 | 26.5 | 26.8 | 25.0 | 25.5 | 26.5 | 26.8 | 27.7 | 28.2 |
| | I | 20.7 | 22.2 | 25.0 | 24.3 | 23.5 | 24.5 | 22.5 | 23.7 | 23.3 | 23.7 |
| | J | 23.7 | 24.8 | 26.5 | 27.8 | 25.0 | 25.5 | 24.2 | 25.3 | 27.7 | 28.0 |
| Average | | 23.6 | 24.3 | 26.0 | 25.7 | 24.5 | 25.0 | 24.7 | 24.8 | 25.8 | 26.3 |
| Std Dev | | 2.0 | 1.5 | 0.7 | 1.5 | 0.7 | 0.5 | 1.6 | 1.4 | 1.9 | 1.9 |
| 3 | K | 22.3 | 23.0 | 23.8 | 24.2 | 23.5 | 23.8 | 24.3 | 24.2 | 24.0 | 23.3 |
| | L | 19.8 | 19.8 | 23.7 | 24.3 | 21.5 | 21.0 | 21.7 | 23.0 | 24.8 | 24.7 |
| | M | 21.8 | 21.8 | 24.2 | 24.0 | 23.5 | 24.3 | 22.7 | 23.0 | 24.3 | 25.2 |
| | N | 24.2 | 24.5 | 23.7 | 24.0 | 22.3 | 23.5 | 22.5 | 22.8 | 24.3 | 25.5 |
| | O | 24.5 | 23.8 | 26.2 | 25.3 | 23.2 | 23.0 | 24.7 | 24.7 | 26.2 | 27.3 |
| Average | | 22.5 | 22.6 | 24.3 | 24.4 | 22.8 | 23.1 | 23.2 | 23.5 | 24.7 | 25.2 |
| Std Dev | | 1.9 | 1.8 | 1.1 | 0.6 | 0.9 | 1.3 | 1.3 | 0.8 | 0.9 | 1.5 |
| 4 | P | 23.3 | 22.0 | 25.0 | 22.7 | 23.5 | 23.5 | 24.0 | 23.8 | 23.3 | 22.8 |
| | Q | 22.8 | 22.5 | 25.8 | 24.3 | 24.8 | 24.5 | 24.5 | 24.8 | 24.5 | 25.2 |
| | R | 19.0 | 18.7 | 25.3 | 24.2 | 23.5 | 23.8 | 23.3 | 22.5 | 24.0 | 24.2 |
| | S | 23.7 | 22.7 | 25.0 | 25.7 | 22.7 | 24.0 | 21.5 | 23.8 | 25.2 | 25.5 |
| | T | 19.7 | 22.0 | 24.8 | 25.2 | 23.3 | 24.3 | 23.2 | 24.8 | 23.5 | 24.3 |
| Average | | 21.7 | 21.6 | 25.2 | 24.4 | 23.6 | 24.0 | 23.3 | 23.9 | 24.1 | 24.4 |
| Std Dev | | 2.2 | 1.6 | 0.4 | 1.1 | 0.8 | 0.4 | 1.1 | 0.9 | 0.8 | 1.0 |
| 5 | U | 21.3 | 23.0 | 26.7 | 24.3 | 22.8 | 22.7 | 25.5 | 24.2 | 24.2 | 25.5 |
| | V | 23.0 | 23.2 | 26.7 | 26.7 | 24.2 | 25.2 | 23.8 | 24.0 | 25.2 | 26.3 |
| | W | 21.5 | 23.0 | 24.2 | 25.0 | 21.3 | 21.8 | 23.5 | 23.8 | 25.5 | 24.7 |
| | X | 24.2 | 25.0 | 25.0 | 26.5 | 24.8 | 25.0 | 26.2 | 25.8 | 25.8 | 26.2 |
| | Y | 20.7 | 20.2 | 23.0 | 23.3 | 24.8 | 24.8 | 23.8 | 23.3 | 26.5 | 26.3 |
| Average | | 22.1 | 22.9 | 25.1 | 25.2 | 23.6 | 23.9 | 24.6 | 24.2 | 25.4 | 25.8 |
| Std Dev | | 1.4 | 1.7 | 1.6 | 1.4 | 1.5 | 1.5 | 1.2 | 0.9 | 0.9 | 0.7 |

OD: Right eye;
OS: left eye

TABLE 24

| Group | Animal ID | Day 1, AM | | Day 1, PM | | Day 2, AM | | Day 3, AM | | Day 4, AM | | Day 5, AM | |
|---|---|---|---|---|---|---|---|---|---|---|---|---|---|
| | | OD | OS | OD | OS | OD | OS | OD | OS | OD | OS | OD | OS |
| 1 | A | 20.7 | 21.5 | 20.7 | 22.7 | 21.2 | 22.3 | 20.8 | 24.0 | 22.0 | 23.7 | 26.0 | 28.2 |
| | B | 24.7 | 23.3 | 24.2 | 24.5 | 23.8 | 23.5 | 25.8 | 26.2 | 27.3 | 26.3 | 25.0 | 24.8 |
| | C | 23.2 | 21.8 | 25.3 | 24.3 | 22.0 | 22.5 | 24.8 | 24.5 | 24.3 | 25.0 | 24.5 | 23.8 |
| | D | 23.0 | 23.0 | 22.2 | 23.3 | 21.2 | 23.3 | 22.3 | 23.0 | 24.5 | 25.2 | 23.3 | 24.2 |
| | E | 23.5 | 23.0 | 24.2 | 24.2 | 21.3 | 22.3 | 23.7 | 23.7 | 24.8 | 24.8 | 23.0 | 22.5 |

TABLE 24-continued

| Group | Animal ID | Day 1, AM OD | Day 1, AM OS | Day 1, PM OD | Day 1, PM OS | Day 2, AM OD | Day 2, AM OS | Day 3, AM OD | Day 3, AM OS | Day 4, AM OD | Day 4, AM OS | Day 5, AM OD | Day 5, AM OS |
|---|---|---|---|---|---|---|---|---|---|---|---|---|---|
| | Average | 23.0 | 22.5 | 23.3 | 23.8 | 21.9 | 22.8 | 23.5 | 24.3 | 24.6 | 25.0 | 24.4 | 24.7 |
| | Std Dev | 1.5 | 0.8 | 1.9 | 0.8 | 1.1 | 0.6 | 2.0 | 1.2 | 1.9 | 1.0 | 1.2 | 2.1 |
| 2 | F | 20.3 | 20.7 | 24.8 | 24.8 | 22.0 | 21.8 | 25.0 | 25.3 | 23.8 | 23.0 | 28.8 | 28.8 |
| | G | 23.7 | 23.3 | 24.8 | 24.2 | 22.7 | 22.3 | 24.2 | 23.5 | 22.0 | 22.7 | 22.8 | 25.0 |
| | H | 24.0 | 25.2 | 29.5 | 28.8 | 25.0 | 24.3 | 26.0 | 26.0 | 26.7 | 26.3 | 28.0 | 28.0 |
| | I | 20.7 | 23.3 | 22.0 | 25.3 | 18.3 | 20.8 | 20.8 | 23.0 | 21.3 | 23.5 | 20.7 | 24.2 |
| | J | 21.7 | 23.8 | 26.2 | 27.2 | 21.7 | 21.5 | 23.8 | 24.5 | 25.7 | 26.2 | 25.7 | 26.3 |
| | Average | 22.1 | 23.3 | 25.5 | 26.1 | 21.9 | 22.2 | 24.0 | 24.5 | 23.9 | 24.3 | 25.2 | 26.5 |
| | Std Dev | 1.7 | 1.6 | 2.7 | 1.9 | 2.4 | 1.3 | 1.9 | 1.2 | 2.3 | 1.8 | 3.4 | 2.0 |
| 3 | K | 23.2 | 23.8 | 23.8 | 24.5 | 17.5 | 19.3 | 19.2 | 20.0 | 23.2 | 23.3 | 21.5 | 22.3 |
| | L | 20.7 | 23.0 | 22.7 | 23.7 | 18.5 | 20.2 | 20.0 | 20.8 | 19.8 | 21.7 | 18.8 | 19.8 |
| | M | 24.0 | 24.7 | 24.7 | 26.8 | 24.3 | 24.0 | 23.0 | 22.7 | 23.8 | 24.2 | 22.3 | 23.5 |
| | N | 20.2 | 21.5 | 25.2 | 25.0 | 18.2 | 18.2 | 19.2 | 19.3 | 24.8 | 24.5 | 21.2 | 20.7 |
| | O | 22.2 | 23.0 | 24.3 | 24.5 | 25.5 | 24.5 | 22.2 | 23.0 | 22.2 | 22.3 | 23.7 | 23.7 |
| | Average | 22.0 | 23.2 | 24.1 | 24.9 | 20.8 | 21.2 | 20.7 | 21.2 | 22.8 | 23.2 | 21.5 | 22.0 |
| | Std Dev | 1.6 | 1.2 | 1.0 | 1.2 | 3.8 | 2.8 | 1.8 | 1.6 | 1.9 | 1.2 | 1.8 | 1.7 |
| 4 | P | 23.2 | 22.0 | 21.3 | 20.8 | 20.5 | 21.0 | 21.8 | 20.0 | 21.5 | 21.8 | 23.8 | 22.7 |
| | Q | 22.0 | 23.3 | 24.0 | 23.3 | 19.8 | 19.7 | 23.5 | 23.5 | 22.8 | 23.2 | 20.8 | 21.7 |
| | R | 20.7 | 19.2 | 23.3 | 22.5 | 20.0 | 19.3 | 21.0 | 19.5 | 20.8 | 20.0 | 20.5 | 18.7 |
| | S | 20.2 | 21.3 | 22.8 | 23.8 | 19.3 | 19.7 | 18.5 | 21.2 | 22.2 | 24.3 | 19.7 | 22.0 |
| | T | 19.8 | 21.2 | 24.2 | 25.5 | 20.3 | 21.0 | 19.0 | 20.3 | 20.7 | 23.5 | 20.3 | 21.2 |
| | Average | 21.2 | 21.4 | 23.1 | 23.2 | 20.0 | 20.1 | 20.8 | 20.9 | 21.6 | 22.6 | 21.0 | 21.2 |
| | Std Dev | 1.4 | 1.5 | 1.1 | 1.7 | 0.5 | 0.8 | 2.1 | 1.6 | 0.9 | 1.7 | 1.6 | 1.5 |
| 5 | U | 21.5 | 24.3 | 24.3 | 20.5 | 17.7 | 18.7 | 16.8 | 17.5 | 20.0 | 18.7 | 21.5 | 20.7 |
| | V | 22.2 | 22.8 | 22.7 | 22.8 | 20.2 | 21.2 | 20.2 | 21.5 | 21.2 | 22.2 | 14.0 | 21.0 |
| | W | 21.5 | 21.8 | 26.2 | 27.2 | 21.5 | 21.7 | 20.3 | 21.5 | 24.7 | 24.7 | 23.7 | 23.2 |
| | X | 23.8 | 24.2 | 24.0 | 26.3 | 25.3 | 24.0 | 22.8 | 22.2 | 22.5 | 23.3 | 26.7 | 25.8 |
| | Y | 22.7 | 24.7 | 19.3 | 21.0 | 22.7 | 22.8 | 23.3 | 23.7 | 21.2 | 22.2 | 26.3 | 26.2 |
| | Average | 22.3 | 23.6 | 23.3 | 23.6 | 21.5 | 21.7 | 20.7 | 21.3 | 21.9 | 22.2 | 22.4 | 23.4 |
| | Std Dev | 1.0 | 1.2 | 2.5 | 3.0 | 2.9 | 2.0 | 2.6 | 2.3 | 1.8 | 2.2 | 5.2 | 2.6 |

OD: Right eye;
OS: left eye

TABLE 25

| Group | Animal ID | Day 6, AM OD | Day 6, AM OS | Day 7, AM OD | Day 7, AM OS | Day 7, PM OD | Day 7, PM OS | Day 8, AM OD | Day 8, AM OS |
|---|---|---|---|---|---|---|---|---|---|
| 1 | A | 26.8 | 26.8 | 23.3 | 24.8 | 22.5 | 24.3 | 25.7 | 26.2 |
| | B | 26.2 | 26.0 | 24.8 | 24.8 | 25.3 | 25.5 | 25.5 | 25.5 |
| | C | 23.8 | 25.2 | 24.3 | 24.0 | 24.3 | 23.2 | 24.0 | 24.2 |
| | D | 24.0 | 17.7 | 24.7 | 25.7 | 24.7 | 25.5 | 24.0 | 24.5 |
| | E | 24.5 | 25.0 | 25.0 | 25.2 | 24.7 | 24.5 | 25.7 | 25.3 |
| | Average | 25.1 | 24.1 | 24.4 | 25.1 | 24.2 | 24.6 | 25.0 | 25.1 |
| | Std Dev | 1.4 | 3.7 | 0.7 | 0.7 | 1.0 | 0.9 | 0.9 | 0.8 |
| 2 | F | 26.8 | 26.5 | 24.2 | 24.2 | 24.8 | 24.2 | 25.8 | 25.8 |
| | G | 25.5 | 24.7 | 23.5 | 23.3 | 25.2 | 25.3 | 25.7 | 25.7 |
| | H | 27.0 | 26.2 | 26.3 | 26.5 | 27.2 | 28.0 | 26.2 | 26.5 |
| | I | 23.7 | 25.0 | 19.8 | 22.7 | 22.2 | 24.7 | 23.2 | 24.7 |
| | J | 24.5 | 24.7 | 24.8 | 26.0 | 26.0 | 26.0 | 23.5 | 23.0 |
| | Average | 25.5 | 25.4 | 23.7 | 24.5 | 25.1 | 25.6 | 24.9 | 25.1 |
| | Std Dev | 1.4 | 0.9 | 2.4 | 1.7 | 1.9 | 1.5 | 1.4 | 1.4 |
| 3 | K | 24.3 | 25.3 | 16.5 | 18.8 | 23.5 | 24.7 | 22.3 | 23.7 |
| | L | 23.3 | 24.5 | 18.3 | 19.2 | 24.3 | 23.8 | 22.7 | 23.0 |
| | M | 26.8 | 27.3 | 25.8 | 24.7 | 26.7 | 25.2 | 25.2 | 25.2 |
| | N | 22.3 | 22.2 | 23.5 | 24.2 | 22.0 | 22.2 | 24.5 | 24.3 |
| | O | 24.2 | 24.2 | 22.7 | 22.0 | 23.8 | 23.8 | 22.5 | 23.5 |
| | Average | 24.2 | 24.7 | 21.3 | 22.0 | 23.7 | 24.2 | 23.4 | 23.9 |
| | Std Dev | 1.7 | 1.9 | 3.7 | 3.1 | 1.0 | 1.6 | 1.3 | 0.8 |
| 4 | P | 23.2 | 22.2 | 23.2 | 24.5 | 24.3 | 22.8 | 22.8 | 22.7 |
| | Q | 24.7 | 24.5 | 23.8 | 23.7 | 26.0 | 26.0 | 24.7 | 24.2 |
| | R | 22.2 | 21.7 | 20.2 | 20.0 | 24.7 | 23.7 | 21.2 | 20.7 |
| | S | 22.2 | 23.5 | 23.0 | 23.8 | 22.7 | 23.5 | 22.3 | 23.5 |
| | T | 20.3 | 24.2 | 22.5 | 25.2 | 25.0 | 26.0 | 22.3 | 23.2 |
| | Average | 22.5 | 23.2 | 22.6 | 23.0 | 24.6 | 24.7 | 22.7 | 22.8 |
| | Std Dev | 1.6 | 1.2 | 1.4 | 2.0 | 1.2 | 1.2 | 1.3 | 1.3 |
| 5 | U | 24.8 | 24.7 | 22.7 | 24.0 | 22.7 | 23.5 | 22.8 | 22.0 |
| | V | 23.8 | 24.0 | 23.3 | 24.0 | 24.5 | 24.5 | 25.2 | 24.8 |
| | W | 25.5 | 25.7 | 23.5 | 23.7 | 25.5 | 24.3 | 24.0 | 24.2 |
| | X | 25.2 | 25.8 | 24.7 | 22.7 | 25.5 | 25.3 | 26.0 | 25.5 |
| | Y | 23.2 | 24.7 | 25.2 | 25.2 | 22.3 | 24.3 | 24.3 | 23.7 |
| | Average | 24.5 | 25.0 | 23.9 | 23.9 | 24.1 | 24.3 | 24.5 | 24.0 |
| | Std Dev | 1.0 | 0.8 | 1.0 | 0.9 | 1.5 | 0.7 | 1.2 | 1.3 |

OD: Right eye;
OS: left eye

EMBODIMENTS

The following non-limiting embodiments provide illustrative examples of the invention, but do not limit the scope of the invention.

Embodiment 1. A method for reducing intraocular pressure in a subject in need thereof, the method comprising administering to the subject a therapeutically-effective amount of a Tie-2 activator, wherein the administration reduces the intraocular pressure by about 0.1 mmHg to about 9 mmHg compared to absence of administration.

Embodiment 2. The method of embodiment 1, wherein the Tie-2 activator binds a phosphatase.

Embodiment 3. The method of any one of embodiments 1-2, wherein the Tie-2 activator inhibits a phosphatase.

Embodiment 4. The method of any one of embodiments 1-3, wherein the Tie-2 activator binds HPTP-β.

Embodiment 5. The method of any one of embodiments 1-4, wherein the Tie-2 activator inhibits HPTP-β.

Embodiment 6. The method of any one of embodiments 1-5, wherein the Tie-2 activator is a phosphate mimetic.

Embodiment 7. The method of any one of embodiments 1-6, wherein the Tie-2 activator is a compound of the formula:

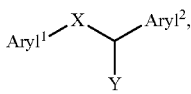

wherein:
Aryl¹ is an aryl group which is substituted or unsubstituted; Aryl² is an aryl group which is substituted or unsubstituted; X is alkylene, alkenylene, alkynylene, an ether linkage, an amine linkage, an amide linkage, an ester linkage, a thioether linkage, a carbamate linkage, a carbonate linkage, a sulfone linkage, any of which is substituted or unsubstituted, or a chemical bond; and Y is H, aryl, heteroaryl, NH(aryl), NH(heteroaryl), NHSO₂R$^g$, or NHCOR$^g$, any of which is substituted or unsubstituted, or

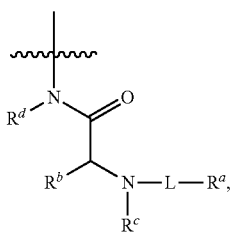

wherein:
L² is alkylene, alkenylene, or alkynylene, any of which is substituted or unsubstituted, or together with the nitrogen atom to which L² is bound forms an amide linkage, a carbamate linkage, or a sulfonamide linkage, or a chemical bond, or together with any of R$^a$, R$^b$, R$^c$, and R$^d$ forms a ring that is substituted or unsubstituted;
R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L², R$^b$, R$^c$, and R$^d$ forms a ring that is substituted or unsubstituted;
R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L², R$^b$, R$^c$, and R$^d$ forms a ring that is substituted or unsubstituted;
R$^c$ is H or alkyl which is substituted or unsubstituted, or together with any of L², R$^a$, R$^b$, and R$^d$ forms a ring that is substituted or unsubstituted;
R$^d$ is H or alkyl which is substituted or unsubstituted, or together with any of L², R$^a$, R$^b$, and R$^c$ forms a ring that is substituted or unsubstituted; and
R$^g$ is H, alkyl, alkenyl, alkynyl, aryl, arylalkyl, heterocyclyl, heterocyclylalkyl, heteroaryl, or heteroarylalkyl, any of which is substituted or unsubstituted,
or a pharmaceutically-acceptable salt, tautomer, or zwitterion thereof.

Embodiment 8. The method of embodiment 7, wherein:
Aryl¹ is substituted or unsubstituted phenyl;
Aryl² is substituted or unsubstituted heteroaryl; and
X is alkylene.

Embodiment 9. The method of any one of embodiments 7-8, wherein:
Aryl¹ is substituted phenyl;
Aryl² is substituted heteroaryl; and
X is methylene.

Embodiment 10. The method of embodiment 1, wherein the compound that activates Tie-2 is a compound of the formula:

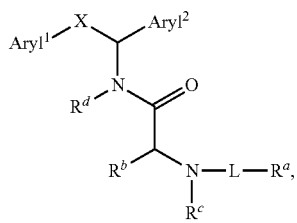

wherein
Aryl¹ is para-substituted phenyl;
Aryl² is substituted heteroaryl;
X is methylene;
L² is alkylene, alkenylene, or alkynylene, any of which is substituted or unsubstituted, or together with the nitrogen atom to which L² is bound forms an amide linkage, a carbamate linkage, or a sulfonamide linkage, or a chemical bond;
R$^a$ is H, alkyl, alkenyl, alkynyl, aryl, arylalkyl, heterocyclyl, heterocyclylalkyl, heteroaryl, or heteroarylalkyl, any of which is substituted or unsubstituted;
R$^b$ is H, alkyl, alkenyl, alkynyl, aryl, arylalkyl, heterocyclyl, heterocyclylalkyl, heteroaryl, or heteroarylalkyl, any of which is substituted or unsubstituted;
R$^c$ is H or alkyl which is substituted or unsubstituted; and
R$^d$ is H or alkyl which is substituted or unsubstituted.

Embodiment 11. The method of embodiment 10, wherein:
Aryl¹ is para-substituted phenyl;
Aryl² is a substituted thiazole moiety;
X is methylene;
L² together with the nitrogen atom to which L² is bound forms a carbamate linkage;
R$^a$ is alkyl, which is substituted or unsubstituted;
R$^b$ is arylalkyl, which is substituted or unsubstituted;
R$^c$ is H; and
R$^d$ is H.

Embodiment 12. The method of any one of embodiments 7-11, wherein Aryl 2 is:

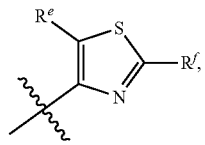

wherein:
R$^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and
R$^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment 13. The method of embodiment 12, wherein:
$R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and
$R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment 14. The method of any one of embodiments 12-13, wherein:
$R^e$ is H, OH, F, Cl, Br, I, alkyl, or an alkoxy group, any of which is substituted or unsubstituted; and
$R^f$ is alkyl, aryl, heterocyclyl, or heteroaryl, any of which is substituted or unsubstituted.

Embodiment 15. The method of any one of embodiments 12-14, wherein:
Aryl¹ is 4-phenylsulfamic acid;
$R^a$ is alkyl, which is substituted or unsubstituted;
$R^b$ is arylalkyl, which is substituted or unsubstituted;
$R^e$ is H; and
$R^f$ is heteroaryl.

Embodiment 16. The method of any one of embodiments 1-15, wherein the compound or Tie-2 activator is:

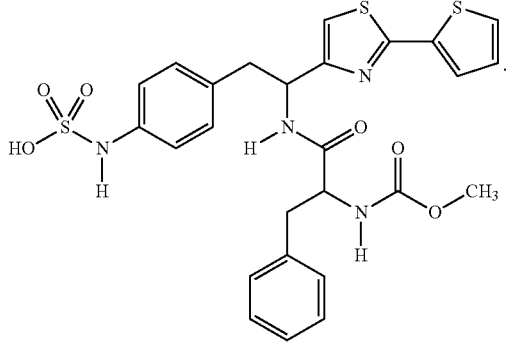 [SMILES: COC(=O)NC(Cc1ccccc1)C(=O)NC(Cc1ccc(NS(=O)(=O)O)cc1)c1csc(-c2cccs2)n1]

Embodiment 17. The method of any one of embodiments 1-15, wherein the compound or Tie-2 activator is:

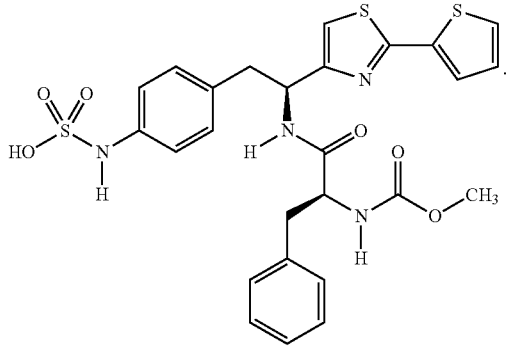 [SMILES: COC(=O)N[C@@H](Cc1ccccc1)C(=O)N[C@@H](Cc1ccc(NS(=O)(=O)O)cc1)c1csc(-c2cccs2)n1]

Embodiment 18. The method of any one of embodiments 12-14, wherein:
Aryl¹ is 4-phenylsulfamic acid;
$R^a$ is alkyl, which is substituted or unsubstituted;
$R^b$ is arylalkyl, which is substituted or unsubstituted;
$R^e$ is H; and
$R^f$ is alkyl.

Embodiment 19. The method of any one of embodiments 1-14 and 18, wherein the compound or Tie-2 activator is:

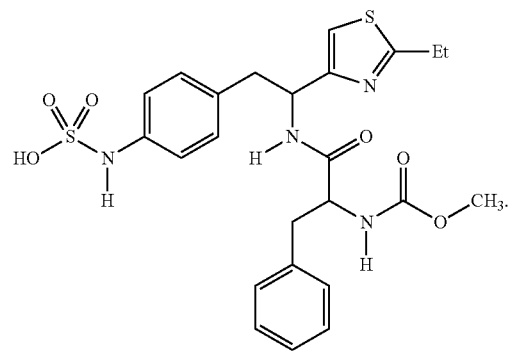 [SMILES: CCc1nc(C(Cc2ccc(NS(=O)(=O)O)cc2)NC(=O)C(Cc2ccccc2)NC(=O)OC)cs1]

Embodiment 20. The method of any one of embodiments 1-14 and 18, wherein the compound or Tie-2 activator is:

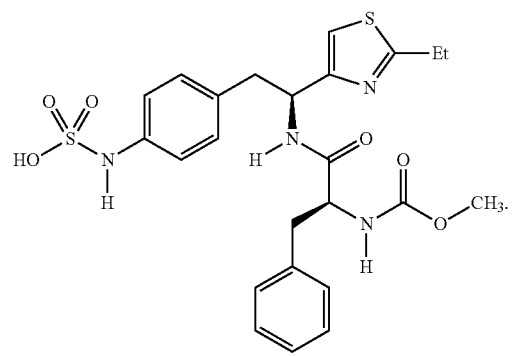 [SMILES: CCc1nc([C@H](Cc2ccc(NS(=O)(=O)O)cc2)NC(=O)[C@H](Cc2ccccc2)NC(=O)OC)cs1]

Embodiment 21. The method of any one of embodiments 7-11, wherein Aryl 2 is:

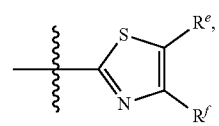

wherein:
$R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment 22. The method of embodiment 21, wherein:
$R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and
$R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment 23. The method of any one of embodiments 21-22, wherein:
$R^e$ is H, OH, F, Cl, Br, I, alkyl, or an alkoxy group, any of which is substituted or unsubstituted; and
$R^f$ is alkyl, aryl, heterocyclyl, or heteroaryl, any of which is substituted or unsubstituted.

Embodiment 24. The method of embodiment 21, wherein:
$Aryl^1$ is 4-phenylsulfamic acid;
$R^a$ is alkyl, which is substituted or unsubstituted;
$R^b$ is arylalkyl, which is substituted or unsubstituted;
$R^e$ is H; and
$R^f$ is heteroaryl.

Embodiment 25. The method of any one of embodiments 1-11 and 21-24, wherein the compound or Tie-2 activator is:

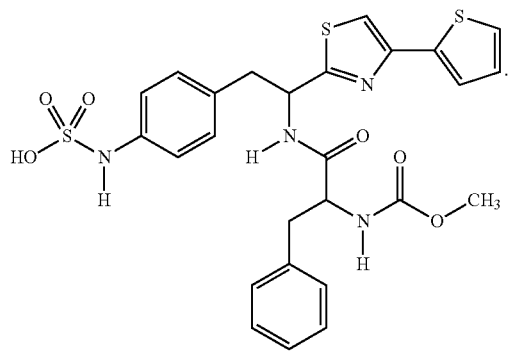 [SMILES: COC(=O)NC(Cc1ccccc1)C(=O)NC(Cc1ccc(NS(=O)(=O)O)cc1)c1nc(-c2cccs2)cs1]

Embodiment 26. The method of any one of embodiments 1-11 and 21-24, wherein the compound or Tie-2 activator is:

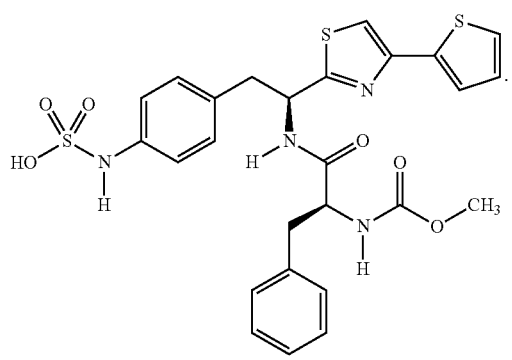 [SMILES: COC(=O)N[C@@H](Cc1ccccc1)C(=O)N[C@@H](Cc1ccc(NS(=O)(=O)O)cc1)c1nc(-c2cccs2)cs1]

Embodiment 27. The method of any one of embodiments 1-26, wherein the therapeutically-effective amount is from about 1 mg to about 100 mg.

Embodiment 28. The method of any one of embodiments 1-27, wherein the therapeutically-effective amount is from about 0.5 mg to about 30 mg.

Embodiment 29. The method of any one of embodiments 1-28, wherein the therapeutically-effective amount is about 15 mg.

Embodiment 30. The method of any one of embodiments 1-28, wherein the therapeutically-effective amount is about 22.5 mg.

Embodiment 31. The method of any one of embodiments 1-28, wherein the therapeutically-effective amount is about 30 mg.

Embodiment 32. The method of any one of embodiments 1-31, wherein the administration is to an eye of the subject.

Embodiment 33. The method of any one of embodiments 1-32, wherein the administration is intravitreal.

Embodiment 34. The method of any one of embodiments 1-31, wherein the administration is subcutaneous.

Embodiment 35. The method of any one of embodiments 1-32, wherein the administration is topical.

Embodiment 36. The method of any one of embodiments 1-32 and 35 wherein the administration is topical to an eye of the subject.

Embodiment 37. The method of any one of embodiments 1-32, 35, and 36 wherein the Tie-2 activator, or a pharmaceutically-acceptable salt thereof, is formulated as a drop.

Embodiment 38. The method of any one of embodiments 1-32 and 35-37 wherein the Tie-2 activator, or a pharmaceutically-acceptable salt thereof, is formulated as a drop, wherein the drop is administered to an eye of the subject.

Embodiment 39. The method of any one of embodiments 1-38, wherein the subject is a human.

Embodiment 40. The method of any one of embodiments 1-39, wherein the intraocular pressure is reduced by at least about 2 mmHg.

Embodiment 41. The method of any one of embodiments 1-40, wherein the subject has glaucoma, wherein the intraocular pressure is associated with glaucoma.

Embodiment 42. The method of any one of embodiments 1-41, wherein the intraocular pressure is ocular hypertension.

Embodiment 43. The method of embodiment 42, wherein the subject has glaucoma, wherein the ocular hypertension is associated with glaucoma.

Embodiment 44. A method for treating glaucoma in a subject in need thereof, the method comprising administering to the subject a therapeutically-effective amount of a Tie-2 activator, wherein the administration reduces intraocular pressure by about 0.1 mmHg to about 9 mmHg compared to absence of administration.

Embodiment 45. The method of embodiment 44, wherein the Tie-2 activator binds a phosphatase.

Embodiment 46. The method of any one of embodiments 44-45, wherein the Tie-2 activator inhibits a phosphatase.

Embodiment 47. The method of any one of embodiments 44-46, wherein the Tie-2 activator binds HPTP-β.

Embodiment 48. The method of any one of embodiments 44-47, wherein the Tie-2 activator inhibits HPTP-β.

Embodiment 49. The method of any one of embodiments 44-48, wherein the Tie-2 activator is a phosphate mimetic.

Embodiment 50. The method of any one of embodiments 44-49, wherein the Tie-2 activator is a compound of the formula:

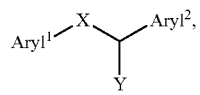

wherein:
$Aryl^1$ is an aryl group which is substituted or unsubstituted; $Aryl^2$ is an aryl group which is substituted or unsubstituted; X is alkylene, alkenylene, alkynylene, an ether linkage, an amine linkage, an amide linkage, an ester linkage, a thioether linkage, a carbamate linkage, a carbonate linkage, a sulfone linkage, any of which is substituted or unsubstituted, or a chemical bond; and Y is H, aryl, heteroaryl, NH(aryl), NH(heteroaryl), $NHSO_2R^g$, or $NHCOR^g$, any of which is substituted or unsubstituted, or

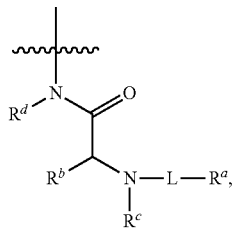

wherein:
- $L^2$ is alkylene, alkenylene, or alkynylene, any of which is substituted or unsubstituted, or together with the nitrogen atom to which $L^2$ is bound forms an amide linkage, a carbamate linkage, or a sulfonamide linkage, or a chemical bond, or together with any of $R^a$, $R^b$, $R^c$, and $R^d$ forms a ring that is substituted or unsubstituted;
- $R^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of $L^2$, $R^b$, $R^c$, and $R^d$ forms a ring that is substituted or unsubstituted;
- $R^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of $L^2$, $R^a$, $R^c$, and $R^d$ forms a ring that is substituted or unsubstituted;
- $R^c$ is H or alkyl which is substituted or unsubstituted, or together with any of $L^2$, $R^a$, $R^b$, and $R^d$ forms a ring that is substituted or unsubstituted;
- $R^d$ is H or alkyl which is substituted or unsubstituted, or together with any of $L^2$, $R^a$, $R^b$, and $R^c$ forms a ring that is substituted or unsubstituted; and
- $R^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

Embodiment 51. The method of embodiment 50, wherein:
Aryl$^1$ is substituted or unsubstituted phenyl;
Aryl$^2$ is substituted or unsubstituted heteroaryl; and
X is alkylene.

Embodiment 52. The method of any one of embodiments 50-51, wherein:
Aryl$^1$ is substituted phenyl;
Aryl$^2$ is substituted heteroaryl; and
X is methylene.

Embodiment 53. The method of embodiment 44, wherein the compound that activates Tie-2 is a compound of the formula:

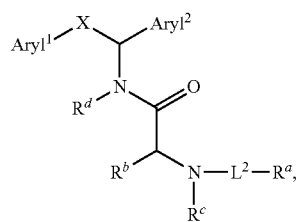

wherein
- Aryl$^1$ is para-substituted phenyl;
- Aryl$^2$ is substituted heteroaryl;
- X is methylene;
- $L^2$ is alkylene, alkenylene, or alkynylene, any of which is substituted or unsubstituted, or together with the nitrogen atom to which $L^2$ is bound forms an amide linkage, a carbamate linkage, or a sulfonamide linkage, or a chemical bond;
- $R^a$ is H, alkyl, alkenyl, alkynyl, aryl, arylalkyl, heterocyclyl, heterocyclylalkyl, heteroaryl, or heteroarylalkyl, any of which is substituted or unsubstituted;
- $R^b$ is H, alkyl, alkenyl, alkynyl, aryl, arylalkyl, heterocyclyl, heterocyclylalkyl, heteroaryl, or heteroarylalkyl, any of which is substituted or unsubstituted;
- $R^c$ is H or alkyl which is substituted or unsubstituted; and
- $R^d$ is H or alkyl which is substituted or unsubstituted.

Embodiment 54. The method of embodiment 51, wherein:
Aryl$^1$ is para-substituted phenyl;
Aryl$^2$ is a substituted thiazole moiety;
X is methylene;
$L^2$ together with the nitrogen atom to which $L^2$ is bound forms a carbamate linkage;
$R^a$ is alkyl, which is substituted or unsubstituted;
$R^b$ is arylalkyl, which is substituted or unsubstituted;
$R^c$ is H; and
$R^d$ is H.

Embodiment 55. The method of any one of embodiments 50-54, wherein Aryl 2 is:

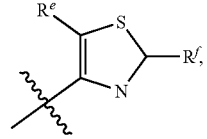

wherein:
- $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and
- $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment 56. The method of embodiment 55, wherein:
$R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and
$R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment 57. The method of any one of embodiments 55-56, wherein:
$R^e$ is H, OH, F, Cl, Br, I, alkyl, or an alkoxy group, any of which is substituted or unsubstituted; and
$R^f$ is alkyl, aryl, heterocyclyl, or heteroaryl, any of which is substituted or unsubstituted.

Embodiment 58. The method of any one of embodiments 55-57, wherein:
Aryl$^1$ is 4-phenylsulfamic acid;
$R^a$ is alkyl, which is substituted or unsubstituted;
$R^b$ is arylalkyl, which is substituted or unsubstituted;
$R^e$ is H; and
$R^f$ is heteroaryl.

Embodiment 59. The method of any one of embodiments 44-58, wherein the compound or Tie-2 activator is:

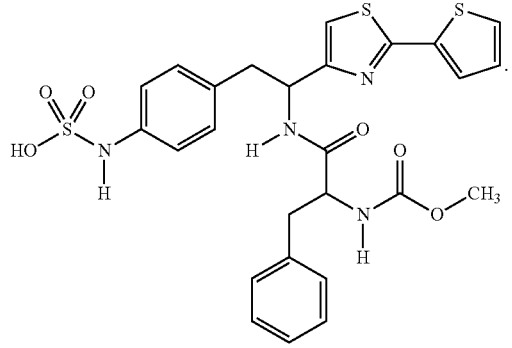 [SMILES: COC(=O)NC(Cc1ccccc1)C(=O)NC(Cc1ccc(NS(=O)(=O)O)cc1)c1csc(-c2cccs2)n1]

Embodiment 60. The method of any one of embodiments 44-58, wherein the compound or Tie-2 activator is:

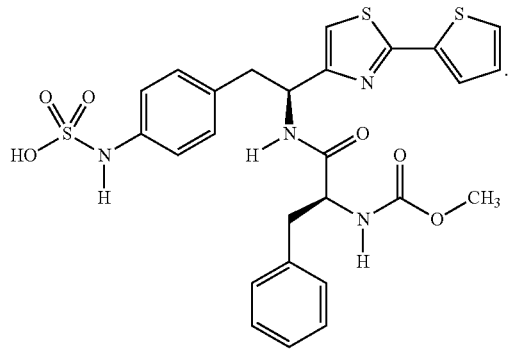 [SMILES: COC(=O)N[C@@H](Cc1ccccc1)C(=O)N[C@@H](Cc1ccc(NS(=O)(=O)O)cc1)c1csc(-c2cccs2)n1]

Embodiment 61. The method of any one of embodiments 55-57, wherein:
Aryl$^1$ is 4-phenylsulfamic acid;
$R^a$ is alkyl, which is substituted or unsubstituted;
$R^b$ is arylalkyl, which is substituted or unsubstituted;
$R^e$ is H; and
$R^f$ is alkyl.

Embodiment 62. The method of any one of embodiments 44-57 and 61, wherein the compound or Tie-2 activator is:

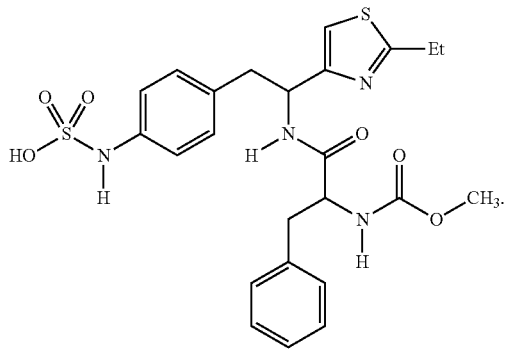 [SMILES: CCc1nc(C(Cc2ccc(NS(=O)(=O)O)cc2)NC(=O)C(Cc2ccccc2)NC(=O)OC)cs1]

Embodiment 63. The method of any one of embodiments 44-57 and 61, wherein the compound or Tie-2 activator is:

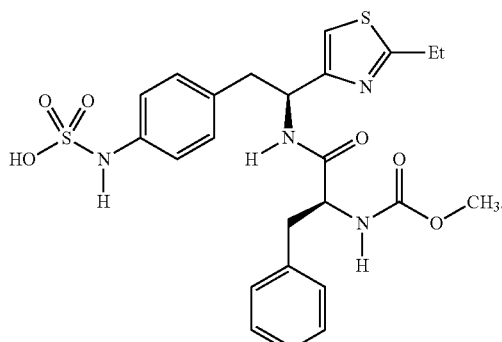

Embodiment 64. The method of any one of embodiments 50-54, wherein Aryl 2 is:

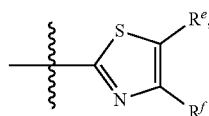

wherein:
$R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment 65. The method of embodiment 64, wherein:
R$^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and
R$^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment 66. The method of any one of embodiments 64-65, wherein:
R$^e$ is H, OH, F, Cl, Br, I, alkyl, or an alkoxy group, any of which is substituted or unsubstituted; and
R$^f$ is alkyl, aryl, heterocyclyl, or heteroaryl, any of which is substituted or unsubstituted.

Embodiment 67. The method of embodiment 64, wherein:
Aryl$^1$ is 4-phenylsulfamic acid;
R$^a$ is alkyl, which is substituted or unsubstituted;
R$^b$ is arylalkyl, which is substituted or unsubstituted;
R$^e$ is H; and
R$^f$ is heteroaryl.

Embodiment 68. The method of any one of embodiments 44-50 and 64-67, wherein the compound or Tie-2 activator is:

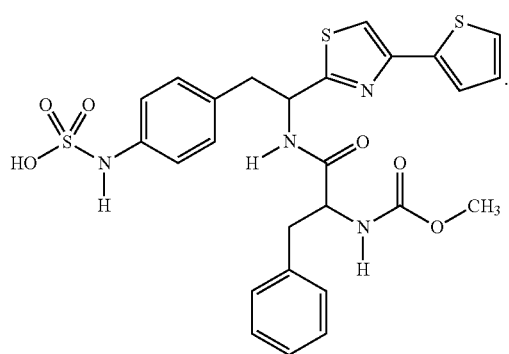 [SMILES: COC(=O)NC(Cc1ccccc1)C(=O)NC(Cc1ccc(NS(=O)(=O)O)cc1)c1nc(-c2cccs2)cs1]

Embodiment 69. The method of any one of embodiments 44-50 and 64-67, wherein the compound or Tie-2 activator is:

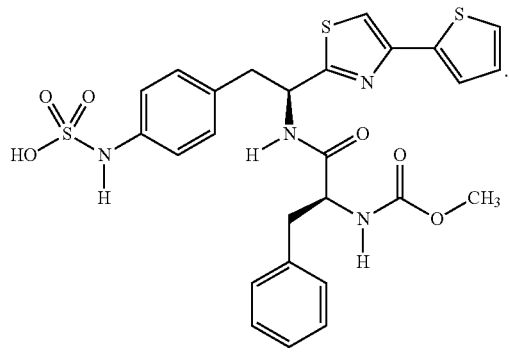 [SMILES: COC(=O)N[C@@H](Cc1ccccc1)C(=O)N[C@@H](Cc1ccc(NS(=O)(=O)O)cc1)c1nc(-c2cccs2)cs1]

Embodiment 70. The method of any one of embodiments 44-69, wherein the therapeutically-effective amount is from about 1 mg to about 100 mg.

Embodiment 71. The method of any one of embodiments 44-70, wherein the therapeutically-effective amount is from about 0.5 mg to about 30 mg.

Embodiment 72. The method of any one of embodiments 44-71, wherein the therapeutically-effective amount is about 15 mg.

Embodiment 73. The method of any one of embodiments 44-71, wherein the therapeutically-effective amount is about 22.5 mg.

Embodiment 74. The method of any one of embodiments 44-71, wherein the therapeutically-effective amount is about 30 mg.

Embodiment 75. The method of any one of embodiments 44-74, wherein the administration is to an eye of the subject.

Embodiment 76. The method of any one of embodiments 44-75, wherein the administration is intravitreal.

Embodiment 77. The method of embodiment 44-74, wherein the administration is subcutaneous.

Embodiment 78. The method of any one of any one of embodiments 44-75, wherein the administration is topical.

Embodiment 79. The method of any one of embodiments 44-75, wherein the administration is topical to an eye of the subject.

Embodiment 80. The method of any one of embodiments 44-75, 78, or 79, wherein the Tie-2 activator, or a pharmaceutically-acceptable salt thereof, is formulated as a drop.

Embodiment 81. The method of any one of embodiments 44-75, and 78-80 wherein the Tie-2 activator, or a pharmaceutically-acceptable salt thereof, is formulated as a drop, wherein the drop is administered to an eye of the subject.

Embodiment 82. The method of any one of embodiments 44-81, wherein the subject is a human.

Embodiment 83. The method of any one of embodiments 44-82, wherein the intraocular pressure is reduced by at least about 2 mmHg.

Embodiment 84. The method of any one of embodiments 44-83, wherein the intraocular pressure is ocular hypertension.

What is claimed is:

1. A method for treating glaucoma in a subject in need thereof, the method comprising administering to the subject a therapeutically-effective amount of a Tie-2 activator, wherein:
   the administration reduces intraocular pressure by about 0.1 mmHg to about 9 mmHg compared to absence of administration;
   the subject expresses Ang-1 and Ang-2;
   the subject is human; and
   the Tie-2 activator is a compound of the formula:

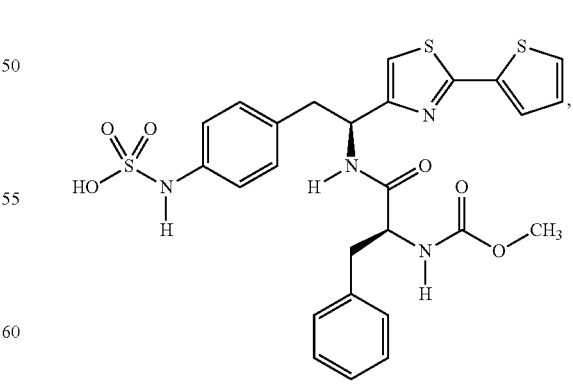

or a pharmaceutically-acceptable salt, tautomer, or zwitterion thereof.

2. The method of claim 1, wherein the Tie-2 activator binds a phosphatase.

3. The method of claim 1, wherein the Tie-2 activator inhibits a phosphatase.

4. The method of claim 1, wherein the Tie-2 activator binds HPTP-B.

5. The method of claim 1, wherein the Tie-2 activator inhibits HPTP-B.

6. The method of claim 1, wherein the Tie-2 activator is a phosphate mimetic.

7. The method of claim 1, wherein the therapeutically-effective amount is from about 1 mg to about 100 mg.

8. The method of claim 7, wherein the therapeutically-effective amount is from about 0.5 mg to about 30 mg.

9. The method of claim 8, wherein the therapeutically-effective amount is about 15 mg.

10. The method of claim 8, wherein the therapeutically-effective amount is about 22.5 mg.

11. The method of claim 1, wherein the therapeutically-effective amount is about 30 mg.

12. The method of claim 1, wherein the administration is to an eye of the subject.

13. The method of claim 1, wherein the administration is intravitreal.

14. The method of claim 1, wherein the administration is subcutaneous.

15. The method of claim 1, wherein the administration is topical.

16. The method of claim 1, wherein the administration is topical to an eye of the subject.

17. The method of claim 1, wherein the Tie-2 activator, or a pharmaceutically-acceptable salt thereof, is formulated as a drop.

18. The method of claim 1, wherein the Tie-2 activator, or a pharmaceutically-acceptable salt thereof, is formulated as a drop, wherein the drop is administered to an eye of the subject.

19. The method of claim 1, wherein the intraocular pressure is reduced by at least about 2 mmHg.

20. The method of claim 1, wherein the intraocular pressure is ocular hypertension.

* * * * *